United States Patent
Moon et al.

(10) Patent No.: US 11,472,887 B2
(45) Date of Patent: Oct. 18, 2022

(54) ANTIBODY BINDING SPECIFICALLY TO MUC1 AND USE THEREOF

(71) Applicant: PEPTRON, INC., Daejeon (KR)

(72) Inventors: Kyung Duk Moon, Daejeon (KR); Ho Il Choi, Daejeon (KR)

(73) Assignee: PEPTRON, INC., Daejeon (KR)

( * ) Notice: Subject to any disclaimer, the term of this patent is extended or adjusted under 35 U.S.C. 154(b) by 89 days.

(21) Appl. No.: 16/495,373

(22) PCT Filed: Mar. 21, 2018

(86) PCT No.: PCT/KR2018/003267
§ 371 (c)(1),
(2) Date: Sep. 18, 2019

(87) PCT Pub. No.: WO2018/174544
PCT Pub. Date: Sep. 27, 2018

(65) Prior Publication Data
US 2020/0024361 A1    Jan. 23, 2020

(30) Foreign Application Priority Data

Mar. 21, 2017 (KR) .................. 10-2017-0035622
Mar. 21, 2018 (KR) .................. 10-2018-0032592

(51) Int. Cl.
C07K 16/30     (2006.01)
A61K 47/65     (2017.01)
A61K 47/68     (2017.01)
C12N 15/62     (2006.01)
G01N 33/574    (2006.01)
C12N 5/16      (2006.01)

(52) U.S. Cl.
CPC .......... C07K 16/3092 (2013.01); A61K 47/65 (2017.08); A61K 47/6851 (2017.08); C12N 15/62 (2013.01); G01N 33/574 (2013.01); C07K 2317/34 (2013.01); C12N 5/16 (2013.01)

(58) Field of Classification Search
CPC ............ C07K 16/3092; C07K 2317/34; A61K 47/65; A61K 47/6851; G01N 33/574
See application file for complete search history.

(56) References Cited

U.S. PATENT DOCUMENTS 7,897,351 B2    3/2011  Wreschner et al.
2007/0105767 A1 5/2007  Kharbanda et al.

FOREIGN PATENT DOCUMENTS

| JP | 2004515472 A | 5/2004 |
| JP | 2005508839 A | 4/2005 |
| JP | 2017505625 A | 7/2017 |
| KR | 20030068536 A | 8/2003 |
| KR | 20130119013 A | 10/2013 |
| KR | 201300119013 A | 10/2013 |
| KR | 20150137015 A | 12/2015 |
| KR | 20160132012 A | 11/2016 |
| WO | 02078598 A2 | 10/2002 |

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Wang et al, PlosOne (2011), vol. 6, Issue 9, e24405. (Year: 2011).*
Gillespie, A.M., et al., "Phase I Open Study of the Effects of Ascending Doses of the Cytotoxic Immunoconjugate CMB-401 (hCTM01-calicheamicin) in Patients With Epithelial Ovarian Cancer", "Annals of Oncology", 2011, pp. 735-741, vol. 11.
Hisatsune, A., et al., "Anti-MUC1 Antibody Inhibits EGF Receptor Signaling in Cancer Cells", "Biochemical and Biophysical Research Communications", 2011, pp. 377-381, vol. 405.

(Continued)

*Primary Examiner* — Jessica H Roark
*Assistant Examiner* — Cheom-Gil Cheong
(74) *Attorney, Agent, or Firm* — Hultquist, PLLC; Steven J. Hultquist

(57) ABSTRACT

The present invention relates to an anti-MUC1 antibody binding specifically to Mucin 1 (MUC1) or an antigen-binding fragment thereof, an antibody-drug conjugate or bispecific antibody comprising the antibody, a pharmaceutical composition for prevention or treatment of cancer, comprising the same antibody, conjugate or bispecific antibody, and a nucleic acid encoding the same antibody, a vector and a host cell, both carrying the same nucleic acid, and a method for preparing an anti-MUC1 antibody or an antigen-binding fragment thereof, using the same vector and host cell. According to the present invention, the antibody shows outstanding affinity and binding force to MUC1 and the antibody-drug conjugate can bind specifically to a MUC1-expressing cell to specifically or selectively transfer the drug with efficacy. Therefore, the anti-MUC1 antibody and the antibody-drug conjugate according to the present invention can be usefully applied to the treatment of a MUC1-related disease, for example, cancer.

6 Claims, 35 Drawing Sheets
(32 of 35 Drawing Sheet(s) Filed in Color)
Specification includes a Sequence Listing.

(56) References Cited

OTHER PUBLICATIONS

Prinssen, H.J., et al., "Biodistribution of 111 In-Labelled Engineered Human Antibody CTM01 (hCTM01) in Ovarian Cancer Patients: Influence of Prior Administration of Unlabelled hCTM01", "Cancer Immunol Immunother", 1998, pp. 39-46, vol. 47.

Yang, C., et al., "MUC1 and Cancer Immunotherapy", "Immunology", 2018, pp. 225-240, vol. 1.

Yokoyama, A., et al., "Prognostic Value of Circulating KL-6 in Idiopathic Pulmonary Fibrosis", "Respirology", 2006, pp. 164-168, vol. 11.

\* cited by examiner

Capan-2/PBS

Capan-2/Anti-hMUC1 Ab

ANTIBODY BINDING SPECIFICALLY TO MUC1 AND USE THEREOF

CROSS-REFERENCE TO RELATED APPLICATIONS

This application is a U.S. national phase under the provisions of 35 U.S.C. § 371 of International Patent Application No. PCT/KR18/03267 filed Mar. 21, 2018, which in turn claims priority of Korean Patent Application No. 10-2017-0035622 filed Mar. 21, 2017 and priority of Korean Patent Application No. 10-2018-0032592 filed Mar. 21, 2018. The disclosures of International Patent Application No. PCT/KR18/03267, Korean Patent Application No. 10-2017-0035622, and Korean Patent Application No. 10-2018-0032592 are hereby incorporated herein by reference in their respective entireties, for all purposes.

TECHNICAL FIELD

The present invention relates to an anti-MUC1 antibody binding specifically to Mucin1 (MUC1) and the use thereof, and more particularly to an anti-MUC1 antibody or an antigen-binding fragment thereof, an antibody-drug conjugate or bispecific antibody comprising the antibody or an antigen-binding fragment thereof, a pharmaceutical composition for the prevention or treatment of cancer comprising the same, a nucleic acid encoding the antibody or an antigen-binding fragment thereof, a vector and a host cell comprising the nucleic acid, and a method for preparing an anti-MUC1 antibody or an antigen-binding fragment thereof using the same.

BACKGROUND ART

Mucin 1 (MUC1) is a transmembrane glycoprotein including a number of glycosylated extracellular domains. MUC1 has a length of 200 to 500 nm on the cell surface and is located in the apical membrane of normal epithelial cells. MUC1 is expressed in linear or luminal epithelial cells of numerous organs such as the breasts, stomach, esophagus, pancreas, urethra, lungs, kidneys and gallbladder. In normal tissues, negatively charged carbohydrates of MUC1 form physical barriers for protecting the basal epithelium from dehydration, pH changes, pollen and microorganisms.

The MUC1 gene encodes a single transcript. After translation, MUC1 is autocleaved in GSVVV motifs located in the SEA domain (sea urchin sperm protein enterokinase and agrin domain). They consist of two peptide fragments, i.e., the N-terminal subunit (MUC1-N) and the C-terminal subunit (MUC1-C).

The MUC1-N terminal subunit has a variable number of tandem repeats and consists of PTS (proline/threonine/serine-rich) domains and SEA domains. The MUC1-C terminal subunit consists of 58 amino acid extracellular domains (ECD), 28 transmembrane domains (TMD) and 72 amino acid cytoplasmic domains (CD). MUC1 causes extensively O-linked glycosylation in the extracellular domain. Depending on the degree of N-glycosylation pattern, the MUC1-C is 23 to 25 kDa in size and is 17 kDa when N-glycosylation is deficient. Once MUC1 is first produced, a portion binding to cells and a portion to be released to the outside of the cells are bound through a noncovalent interaction. In this case, cleavage is caused by an enzyme called "sheddase". The MUC1 complex is isolated by stimulation of cytokines such as IFN-γ and TNF-α. MUC1-N is released by enzymes including TNF-alpha-converting enzyme (TACE) and matrix metallo-protease (MMP). These enzymes cleave the ECD of MUC1-C into two fragments. As the cancer progresses, the extracellular fragment is isolated from cancer cells and floats in the blood of the body, whereas the cell-bound fragment continuously remains bound to the cancer cells. MUC1 is important for the growth of cancer cells because it plays a crucial role in cancer cell proliferation by sending a continuous cell proliferation signal through binding to cell membrane proteins that are associated with cancer cell proliferation and are present in other cancer cells. In addition, this fragment shares the same fate as cancer cells until the cancer cells are grown and eliminated, thus acting as a good target for cancer detection and serving as a critical biomarker for removing cancer. In addition, unlike other parts of MUC1, this fragment was known to be the only part that is not glycosylated, and was considered to be a distinct part that distinguishes MUC1 of cancer cells from MUC1 of normal cells. Accordingly, the present inventors have developed an antibody of the present invention based on the opinion that this fragment, which binds to MUC1 cells and shares the fate of cancer and can distinguish MUC1 of normal cells from MUC1 of cancer cells, is capable of serving as an optimal antigen to the antibody.

Meanwhile, an antibody-drug conjugate (ADC) is obtained by binding a cytotoxic drug to an antibody via a linker. Since a monoclonal antibody has target-specific properties, the drug in the antibody-drug conjugate can be delivered to a tumor expressing an antigen/target that is recognized by a monoclonal antibody having selective targeting ability. It is ideal that the antibody-drug conjugate, which takes a prodrug form in the blood after administration, should be non-toxic, and that, when the antibody binds to the target tumor antigen and is then internalized into the cancer cell, the drug is released in an active form and kills the cancer cell.

The most important key point to prepare the antibody-drug conjugates is to determine the target/antigen to which the antibody binds. In particular, the target/antigen, to which the antibody binds, has been considered to be a cell surface protein which is predominantly expressed in tumor cells and ideally is expressed (overexpressed) specifically to cancer cells.

Under these technical backgrounds, the present inventors have developed an antibody specifically binding to cancer cell-MUC1 that recognizes a portion different from MUC1 expressed in normal cells, and have found that an anti-MUC1-antibody binding to "a portion bound to a cell" that binds to cancer cells and thus shares the fate of the cancer cells, based on the characteristics of ADC in order to maximize ADC efficacy, and an antibody-drug conjugate including the same are capable of specifically binding to MUC1-expressing cells and thus treating diseases caused by MUC1 expression. Based on this finding, the present invention has been completed.

The above information disclosed in this Background section is provided only for better understanding of the background of the present invention and therefore it may not contain information that forms the prior art that is already known to those skilled in the field to which the present invention pertains.

DISCLOSURE

Technical Problem

It is an object of the present invention to provide an antibody or an antigen-binding fragment thereof specifically binding to "a portion bound to a cell" of MUC1, an antibody-drug conjugate in which a drug conjugated with the antibody or an antigen-binding fragment thereof, and a bispecific antibody comprising the antibody or an antigen-binding fragment thereof.

It is another object of the present invention to provide a hybridoma (KCLRFBP 00395) for producing the anti-MUC1 antibody.

It is another object of the present invention to provide a composition for preventing or treating cancer comprising the anti-MUC1 antibody or an antigen-binding fragment thereof, the antibody-drug conjugate or the bispecific antibody, and a method for treating cancer using the same.

It is another object of the present invention to provide a composition for diagnosing cancer comprising the anti-MUC1 antibody or an antigen-binding fragment thereof and a method for diagnosing cancer using the same.

It is another object of the present invention to provide an immunogenic composition comprising a complex in which a MUC1-C terminal region, a SEA domain of MUC1 or a C-terminal extracellular domain of MUC1, and CpG-DNA encapsulated in a liposome.

It is another object of the present invention to provide a method for producing an anti-MUC1 monoclonal antibody comprising inoculating a mouse with the immunogenic composition.

It is yet another object of the present invention to provide a nucleic acid encoding the anti-MUC1 antibody or an antigen-binding fragment thereof, a vector and a host cell comprising the nucleic acid, and a method for producing an anti-MUC1 antibody or an antigen-binding fragment thereof using the same.

Technical Solution

To achieve the above object, the present invention provides an anti-MUC1 antibody or an antigen-binding fragment thereof recognizing a polypeptide comprising at least five consecutive amino acids within a C-terminal extracellular domain of MUC1.

Preferably, the anti-MUC1 antibody or antigen-binding fragment thereof comprises six complementarity determining regions (CDRs), wherein the antibody or antigen-binding fragment thereof includes at least one sequence selected from the group consisting of: heavy-chain CDR1 of SEQ ID NO: 1 (GYTFTSYWMH); heavy-chain CDR2 of SEQ ID NO: 2 (YINPGTGYIEYNQKFKD); heavy-chain CDR3 of SEQ ID NO: 3 (STAPFDY); light-chain CDR1 of SEQ ID NO: 4 (KASQDIKSYLS); light-chain CDR2 of SEQ ID NO: 5 (YATRLAD); and light-chain CDR3 of SEQ ID NO: 6 (LQYDESPYT).

The present invention also provides a hybridoma (KCLRFBP 00395) for producing the anti-MUC1 antibody.

The present invention also provides an antibody-drug conjugate or a bispecific antibody comprising the anti-MUC1 antibody or an antigen-binding fragment thereof.

The present invention also provides a pharmaceutical composition for preventing or treating cancer comprising the anti-MUC1 antibody or an antigen-binding fragment thereof, the antibody-drug conjugate or the bispecific antibody, and a method for treating cancer using the same.

The present invention also provides a use of the anti-MUC1 antibody or an antigen-binding fragment thereof for preventing or treating cancer.

The present invention also provides a use of the anti-MUC1 antibody or an antigen-binding fragment thereof for preparing a preventive or therapeutic agent for cancer.

The present invention also provides a composition for diagnosing cancer comprising the anti-MUC1 antibody or an antigen-binding fragment thereof and a method for diagnosing cancer using the same.

The present invention also provides an immunogenic composition comprising (1) a C-terminal region of MUC1, a SEA domain of MUC1 or a C-terminal extracellular domain of MUC1, and (2) CpG-DNA encapsulated in the liposome, and a method for producing an anti-MUC1 monoclonal antibody comprising inoculating a mouse with the immunogenic composition.

The present invention also provides a nucleic acid encoding the anti-MUC1 antibody or an antigen-binding fragment thereof, a vector and a host cell comprising the nucleic acid, and a method for producing an anti-MUC1 antibody or an antigen-binding fragment thereof using the same.

DESCRIPTION OF DRAWINGS

The patent or application file contains at least one drawing executed in color. Copies of this patent or patent application publication with color drawing(s) will be provided by the Office upon request and payment of the necessary fee.

FIG. 1b shows the result of screening using HAT medium and FIG. 1c shows the result of screening using HT medium.

DETAILED DESCRIPTION AND EXEMPLARY EMBODIMENTS

Figure 1A:
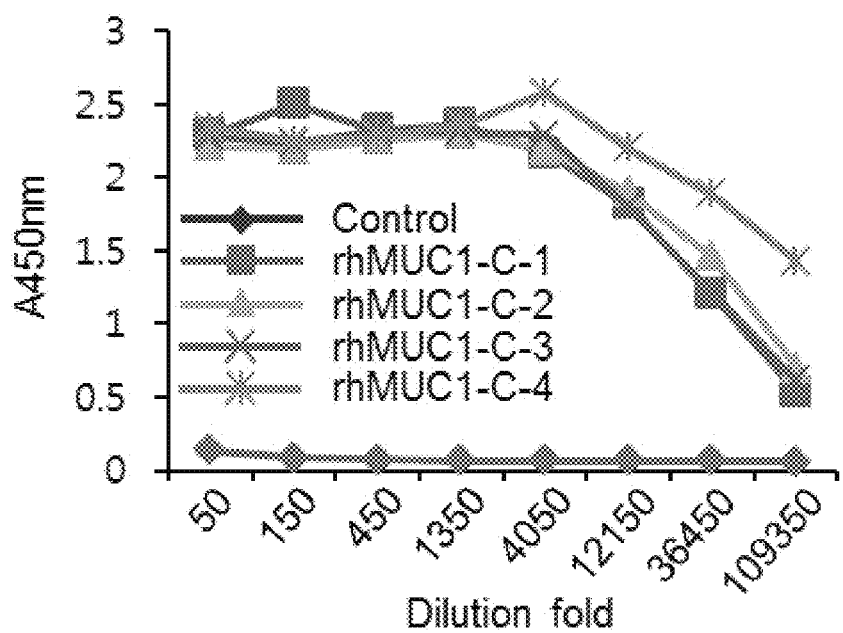
FIG. 1a is a graph showing the total amount of IgG in mice immunized with rhMUC1-C protein.

Unless defined otherwise, all technical and scientific terms used herein have the same meanings as appreciated by those skilled in the field to which the present invention pertains. In general, the nomenclature used herein is well-known in the art and is ordinarily used.

MUC1 (Mucin 1) is generally expressed on one side (apical membrane) of the normal epithelium and protects the basal epithelium from drying, pH changes, contamination and microorganisms. However, MUC1 is abnormally expressed at a high level in various human carcinomas, is involved in reduction of the degree of glycosylation, is evenly expressed over the entire surface of cells and is involved in promoting proliferation, invasion, metastasis and angiogenesis of cancer cells. MUC1 is therefore a target for cancer-specific therapies.

MUC1 includes an N-terminal subunit (MUC1-N) and a C-terminal subunit (MUC1-C), wherein MUC1-N and MUC1-C are formed by self-cleavage in the cleavage site within the SEA domain (sea urchin sperm protein enterokinase and agrin domain). The SEA domain contributes to the formation of stable heterodimeric complexes. When MUC1 cleavage occurs, extracellular MUC1-N (the N-terminal subunit of MUC1) can be released to isolate a number of anti-MUC1-SEA antibodies. Most anti-MUC1-SEA antibodies known to date are known to target the MUC1-N repeating sequence domains (Prinssen et al. 1998; Gillespie et al. 2000). Since MUC1-N is not found directly on the cell surface but is observed during peripheral circulation, there is a limitation in that only limited circulating anti-MUC1-N antibodies can be used in MUC1-positive tumor cells. Also, it is difficult to select the epitope of MUC1-C (the C-terminal subunit of MUC1). The reason for this is that, in most cases, the MUC1-C domain is a transmembrane or located in the cytoplasm. In order to overcome this problem, the present invention provides a novel antibody specifically binding to MUC1 that targets the MUC1-C terminal region (extracellular domain) remaining on the cell surface after MUC1 cleavage.

In one aspect, the present invention relates to an anti-MUC1 antibody binding specifically to MUC1, or an antigen-binding fragment thereof, more particularly, to an anti-MUC1 antibody recognizing a polypeptide comprising at least five consecutive amino acids within the C-terminal extracellular domain of MUC1, or an antigen-binding fragment thereof.

Particularly, in the present invention, an antigen expressing a total of 192 amino acids from the amino acid at position 961 to the amino acid at position 1152 (including the SEA domain) among 1134 amino acids of human Mucin1 (CD227) whole protein is used, based on the technique of "immunostimulatory compositions comprising liposome-encapsulated oligonucleotide and epitopes" disclosed in the patent PCT/KR2010/003879. Mucin1 has about 100-fold higher expression in a variety of human adenocarcinoma cancer cells (Immunology, 2018, 225-240). Specifically, Mucin1 is synthesized in cells and then cleaved at the SEA domain into two subunits, i.e., a cell-bound portion including the SEA domain and the remaining portion, which are noncovalently bonded. In normal cells, MUC1 is heavily glycosylated, but this part is predominant in the truncated portion and is not glycosylated in the cell-bound portion. In the present invention, based on this fact, 190 amino acids binding to the cells even after cleavage are used as antigens to express in E. coli that has not undergone glycosylation.

Since the antibody according to the present invention is produced based on an antigen expressed in E. coli, it recognizes an antigen that is not glycosylated. In the present invention, an antibody was developed using the mouse hybridoma technique, and interestingly, the developed antibody was found to recognize the tertiary structure, rather than the primary structure of the amino acid sequence.

In one embodiment of the present invention, it was found that when FACS was performed using the T47D and ZR75-1 breast cancer cell lines, MUC-1 was specifically recognized, but the cell lysate obtained by cell lysis was not recognized by Western blotting performed to observe the primary structure. The antigen was detected upon immunoprecipitation using the cell lysate and the antibody according to the present invention, followed by Western blotting, in order to verify the recognition of the tertiary structure, which indicates that the antibody according to the present invention specifically recognizes the tertiary structure.

In the present invention, the C-terminal extracellular domain of MUC1 may have the amino acid sequence of SEQ ID NO: 10 (SVV VQLTLAFREG TINVHDVETQ FNQYK-TEAAS RYNLTISDVS VSDVPFPFSA QS).

The term "antibody" as used herein refers generally to a substance produced by the stimulation of an antigen in the immune system, and the kind thereof is not particularly limited. The antibody means an immunoglobulin molecule that immunologically reacts with a specific antigen, and is a protein molecule acting as a receptor specifically recognizing an antigen, and includes all of a polyclonal antibody, a monoclonal antibody, a whole antibody and an antibody fragment. The antibody may be non-naturally produced, for example, recombinantly or synthetically produced. The antibody may be an animal antibody (e.g., a mouse antibody), a chimeric antibody, a humanized antibody or a human antibody. The antibody may be a monoclonal antibody. The antibody may also be understood to include an antigen-binding fragment of an antibody having antigen-binding ability, unless otherwise specified.

In the present specification, the term "complementarity determining region (CDR)" refers to a site that imparts binding specificity to an antigen among variable regions of the antibody. The antigen-binding fragment of the antibody described above may be an antibody fragment including at least one of the complementarity determining regions.

In the present invention, the anti-MUC1 antibody may be produced from the hybridoma hMUC1-1H7 (KCLRF-BP-00395). In addition, the anti-MUC1 antibody or antigen-binding fragment thereof has complementarity determining regions (CDR-H1, CDR-H2, CDR-H3, CDR-L1, CDR-L2 and CDR-L3), or a heavy-chain variable region and a light-chain variable region of the antibody produced from the hybridoma hMUC1-1H7 (KCLRF-BP-00395).

In one aspect, an anti-MUC1 antibody or antigen-binding fragment thereof according to the present invention includes six complementarity determining regions (CDRs). The antibody or antigen-binding fragment thereof includes at least one selected from the group consisting of: heavy-chain CDR1 of SEQ ID NO: 1 (GYTFTSYWMH); heavy-chain CDR2 of SEQ ID NO: 2 (YINPGTGYIEYNQKFKD); heavy-chain CDR3 of SEQ ID NO: 3 (STAPFDY); light-chain CDR1 of SEQ ID NO: 4 (KASQDIKSYLS); light-chain CDR2 of SEQ ID NO: 5 (YATRLAD); and light-chain CDR3 of SEQ ID NO: 6 (LQYDESPYT).

In the present invention, the antibody or antigen-binding fragment thereof may include: heavy-chain CDR1 of SEQ ID NO: 1; heavy-chain CDR2 of SEQ ID NO: 2; heavy-chain CDR3 of SEQ ID NO: 3; light-chain CDR1 of SEQ ID NO: 4; light-chain CDR2 of SEQ ID NO: 5; and light-chain CDR3 of SEQ ID NO: 6.

In the present invention, the antibody or antigen-binding fragment thereof may be characterized in that it includes a heavy-chain variable region of SEQ ID NO: 22 or 24, and a light-chain variable region of SEQ ID NO: 23 or 25. More specifically, the antibody or an antigen-binding fragment thereof includes a heavy-chain variable region of SEQ ID NO: 22 and a light-chain variable region of SEQ ID NO: 23; or a heavy-chain variable region of SEQ ID NO: 24 and a light-chain variable region of SEQ ID NO: 25.

In the present invention, the anti-MUC1 antibody or an antigen-binding fragment thereof has an inhibitory effect against MUC1.

The MUC1 gene encodes one transcript, and after translation, the MUC1 protein is autocleaved in "G" of the GSVVV motif located within the SEA domain. In the present invention, the MUC1 protein may be a human MUC1 protein, and for example may have the amino acid sequence of GenBank Accession No. P15941 (SEQ ID NO: 7), or a sequence homology of at least 80%, at least 85%, at least 90%, at least 95%, at least 96%, at least 97%, at least 98%, or at least 99% therewith. The extracellular domain of the MUC1 protein may be an extracellular domain of a human MUC1 protein, for example, a protein fragment (SEQ ID NO: 8) including 192 amino acids in total from the amino acid at position 961 to the amino acid at position 1152 in the amino acid sequence of GenBank Accession No. P15941 (SEQ ID NO: 7). The extracellular domain of the MUC1 protein includes a SEA domain. In one example, the SEA domain is a protein fragment (SEQ ID NO: 9) including 119 amino acids in total from the amino acid at position 1034 to the amino acid at position 1152 in the amino acid sequence of GenBank Accession No. P15941 (SEQ ID NO: 7). The "G" of the GSVVV motif present in the SEA domain is the cleavage site, and when cleavage occurs at this site, the site after the "G" (in the C-terminal direction) is the C-terminal extracellular domain (also referred to as "MUC1-C terminal (site) extracellular domain" or "MUC1-C subunit") (SEQ ID NO: 10) (Table 1).

TABLE 1

| MUC1 protein site | Description | Sequence |
|---|---|---|
| Whole amino acid sequence of MUC1 protein | Whole amino acid sequence of P15941 | MTPGTQSPFF LLLLLTVLTV VTGSGHASST PGGEKETSAT QRSSVPSSTE KNAVSMTSSV LSSHSPGSGS STTQGQDVTL APATEPASGS AATWGQDVTS VPVTRPALGS TTPPAHDVTS APDNKPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDNRPALGS TAPPVHNVTS ASGSASGSAS TLVHNGTSAR ATTTPASKST PFSIPSHHSD TPTTLASHST KTDASSTHHS SVPPLTSSNH STSPQLSTGV SFFFLSFHIS NLQFNSSLED PSTDYYQELQ RDISEMFLQI YKQGGFLGLS NIKFRPGSVV VQLTLAFREG TINVHDVETQ FNQYKTEAAS RYNLTISDVS VSDVPFPFSA QSGAGVPGWG IALLVLVCVL VALAIVYLIA LAVCQCRRKN YGQLDIFPAR DTYHPMSEYP TYHTHGRYVP PSSTDRSPYE KVSAGNGGSS LSYTNPAVAA TSANL (SEQ ID NO: 7) |
| Extracellular domain of MUC1 protein (C terminal direction) | Including 192 amino acids from 961st to 1152nd amino acid in P15941 | ASGSASGSAS TLVHNGTSAR ATTTPASKST PFSIPSHHSD TPTTLASHST KTDASSTHHS SVPPLTSSNH STS<u>PQLSTGV SFFFLSFHIS NLQFNSSLED PSTDYYQELQ RDISEMFLQI YKQGGFLGLS NIKFRPGSVV VQLTLAFREG TINVHDVETQ FNQYKTEAAS RYNLTISDVS VSDVPFPFSA QS</u> (SEQ ID NO: 8; underlined: SEA domain; "G": cleavage site) |
| SEA domain of MUC1 protein | Including 119 amino acids from 1034st to 1152nd amino acid in P15941 | PQLSTGV SFFFLSFHIS NLQFNSSLED PSTDYYQELQ RDISEMFLQI YKQGGFLGLS NIKFRPGSVV VQLTLAFREG TINVHDVETQ <u>FNQYKTEAAS RYNLTISDVS VSDVPFPFSA QS</u> (SEQ ID NO: 9; underlined: C-terminal extracellular domain) |
| Extracellular domain of MUC1-C terminal site | C-terminal subunit produced by cleavage in SEA domain of MUC1 protein | SVV VQLTLAFREG TINVHDVETQ FNQYKTEAAS RYNLTISDVS VSDVPFPFSA (SEQ ID NO: 10) |

In the present invention, the anti-MUC1 antibody or an antigen-binding fragment thereof recognizes or specifically binds to a polypeptide (epitope) including at least 5, at least 7, at least 10, at least 12, or preferably at least 15 amino acids within a MUC1 protein (e.g., SEQ ID NO: 7), specifically, the C-terminal extracellular domain (e.g., SEQ ID NO: 10) of the MUC1 protein. The anti-MUC1 antibody or an antigen-binding fragment thereof recognizes and/or specifically binds to the extracellular domain of the MUC1 protein (e.g., SEQ ID NO: 8), the SEA domain of the MUC1 protein (e.g., SEQ ID NO: 9) or the C-terminal extracellular domain of the MUC1 protein (e.g., SEQ ID NO: 10).

As used herein, the term "MUC1-specific antibody" or "antibody specifically binding to MUC1" means an antibody that binds to MUC1 to cause inhibition of the biological activity of MUC1, and is used interchangeably with "anti-MUC1 antibody".

As used herein, the term "anti-MUC1 antibody" refers to an animal antibody (e.g., a mouse antibody), a chimeric antibody (e.g., a mouse-human chimeric antibody) or a humanized antibody, and may be a monoclonal antibody or a polyclonal antibody, for example, a monoclonal antibody. The term "anti-MUC1 antibody" encompasses both a polyclonal antibody and a monoclonal antibody, and is preferably a monoclonal antibody, and may have a whole antibody form. The whole antibody has two full-length light chains and two full-length heavy chains, and includes constant regions, wherein each light chain is linked to the corresponding heavy chain by a disulfide bond.

The whole antibody of the anti-MUC1 antibody according to the present invention includes IgA, IgD, IgE, IgM and IgG forms, and IgG includes subtypes IgG1, IgG2, IgG3 and IgG4.

The whole (complete) IgG antibody has a structure having two full-length light chains and two full-length heavy chains, wherein each light chain is linked to the corresponding heavy chain by a disulfide bond. The constant region of the antibody is divided into a heavy-chain constant region and a light-chain constant region. The heavy-chain constant region has gamma (γ), mu (μ), alpha (α), delta (δ) and epsilon (ε) types and is subclassified into gamma 1 (γ1), gamma 2 (γ2), gamma 3 (γ3), gamma 4 (γ4), alpha 1 (α1) and alpha 2 (α2). The light-chain constant region has kappa (κ) and lambda (λ) types.

As used herein, the term "heavy chain" encompasses a full-length heavy chain, which includes a variable region domain ($V_H$) containing an amino acid sequence having a sufficient variable region sequence for imparting specificity to an antigen, three constant regions ($C_{H1}$, $C_{H2}$ and $C_{H3}$) and a hinge, and a fragment thereof. Also, as used herein, the term "light chain" encompasses a full-length light chain, which includes a variable region domain ($V_L$) containing an amino acid sequence having a sufficient variable region sequence for imparting specificity to an antigen, a constant region CL and a fragment thereof.

As used herein, the term "complementarity determining region (CDR)" refers to an amino acid sequence of the hypervariable region of heavy chains and light chains of immunoglobulin. The heavy chains and light chains may each have three CDR regions (CDRH1, CDRH2, CDRH3, and CDRL1, CDRL2, CDRL3). The CDRs may provide the major contact residues for binding of the antibody to the antigen or epitope.

Meanwhile, the term "specifically binding" or "specifically recognizing" has the same meaning as that commonly known to those skilled in the art, which means that an antigen and an antibody immunologically react with each other through specific interaction.

The term "antigen-binding fragment" of the anti-MUC1 antibody according to the present invention refers to a fragment that has the ability to bind to an antigen of an anti-MUC1 antibody, that is, MUC1, and includes Fab, Fab', F(ab')$_2$, scFv, (scFv)$_2$, scFv-Fc, Fv and the like. Herein, the term "antigen-binding fragment" has the same meaning as the term "antibody fragment" and is used interchangeably therewith. The antigen-binding fragment may be, for example, scFv, (scFv)$_2$, Fab, Fab' or F(ab')$_2$, but is not limited thereto. Among the antigen-binding fragments, Fab includes a variable region of each of the heavy chain and the light chain, a constant region of the light chain and the first constant region ($C_{H1}$) of the heavy chain, and has one antigen-binding site. Fab' is different from Fab in that it further includes a hinge region having at least one cysteine residue at the C-terminus of the $C_{H1}$ domain of the heavy chain. The F(ab')$_2$ antibody is formed by a disulfide bond between cysteine residues in a hinge region. Fv is the minimal antibody fragment having only a heavy-chain variable region and a light-chain variable region, and recombination technology for producing Fv fragments is well-known in the art. Two-chain Fv has a structure in which a light-chain variable region is linked to a heavy-chain variable region via a non-covalent bond and single-chain Fv has a structure in which a heavy-chain variable region and a light-chain variable region are linked by covalent bond via a peptide linker, or are directly linked at the C-terminal, to form a dimer-like structure, like the two-chain Fv. The antigen-binding fragment may be obtained using a protease (e.g., Fab can be obtained by restriction-cleaving the whole antibody with papain, and the F(ab')$_2$ fragment can be obtained by restriction-cleaving the whole antibody with pepsin), and may be prepared by genetic recombination techniques.

As herein used, the term "hinge region" refers to a region which is included in the heavy chain of an antibody, is interposed between CH1 and CH2 domains, and functions to impart flexibility to the antigen-binding site in the antibody.

The anti-MUC1 antibody may be a monoclonal antibody. The monoclonal antibody can be prepared in accordance with a method well-known in the art, for example, by a phage display technique. Alternatively, the monoclonal antibody may be derived from mice through a conventional method using the anti-MUC1 antibody.

Meanwhile, individual monoclonal antibodies can be screened based on the binding ability with MUC1 using a typical ELISA (enzyme-linked immunosorbent assay) format. The inhibitory activity can be tested through functional analysis such as competitive ELISA for testing the molecular interaction on bound substances, and functional analysis such as cell-based assays. The affinity (Kd value) to MUC1 of selected monoclonal antibody members based on strong inhibitory activity is tested.

At least one of CDR1 to CDR3 of light and heavy chains contained in the anti-MUC1 antibody or antigen-binding fragment thereof according to the present invention, as well as peptides and aptamers having substantially the same binding ability and specificity for the MUC1 antigen, fall within the scope of the anti-MUC1 antibody or antigen-binding fragment thereof according to the present invention.

In another aspect, the present invention relates to a hybridoma producing the anti-MUC1 antibody. In the present invention, the hybridoma is deposited under the accession number KCLRF-BP-00395.

The present invention provides an anti-MUC1 antibody produced by the hybridoma or an antigen-binding fragment thereof. In another example, the present invention provides an anti-MUC1 antibody or an antigen-binding fragment thereof that includes a heavy-chain complementarity determining region (CDR-H1, CDR-H2, CDR-H3, or a combination thereof) or a light-chain complementarity determining region (CDR-L1, CDR-L2, CDR-L3, or a combination thereof) of the anti-MUC1 antibody produced by the hybridoma, or a combination thereof; or a heavy-chain variable region or a light-chain variable region of the anti-MUC1 antibody produced by the hybridoma or a combination thereof. In this case, the complementarity determining region may be determined by any conventional method, for example, through IMGT definition (www.imgt.org/IMGT_vquest/share/textes/), or Kabat definition (www.bioinf.org.uk/abs/), but is not limited thereto.

In the present invention, the anti-MUC1 antibody or antigen-binding fragment thereof specifically recognizes the C-terminal extracellular domain of MUC1, so that the MUC1-C terminal extracellular domain is expressed at a higher level than in normal cells, and the anti-MUC1 antibody or antigen-binding fragment thereof specifically acts on less glycosylated cancer or tumor cells and can recognize/bind MUC1 protein expressed on the whole surface as well as on one side of the cell. In addition, the anti-MUC1 antibody or antigen-binding fragment thereof not only binds to the MUC1 protein, particularly the MUC1-C terminal extracellular domain, but also internalizes the MUC1 protein into cells (see Example 9-8, Example 18), thereby effectively inhibiting MUC1-mediated pathways and maximizing pharmacological effects. In addition, the internalization property of the anti-MUC1 antibody or antigen-binding fragment thereof has the advantage of effectively delivering the conjugated drug into cells upon application as an antibody-drug conjugate (ADC).

In another aspect, the present invention relates to a chimeric antigen receptor (CAR)-T cell therapeutic agent and/or a chimeric antigen receptor (CAR)-natural killer cell (NK) comprising the anti-MUC1 antibody or an antigen-binding fragment thereof according to the present invention. The form of the anti-MUC1 antibody or antigen-binding fragment thereof contained in CAR-T or CAR-NK is preferably scFv, but the present invention is not limited thereto.

In another aspect, the present invention relates to an antibody-drug conjugate (ADC) in which a drug is conjugated to the anti-MUC1 antibody or antigen-binding fragment thereof.

In one embodiment of the invention, the drug of the antibody-drug conjugate is monomethyl auristatin E (MMAE). After binding to a MUC1-expressing cell, the antibody-drug conjugate is internalized into a MUC1-expressing tumor cell, and MMAE is selectively released into the target MUC1 cell through proteolytic cleavage. When the released MMAE binds to tubulin, it cleaves the intracellular microtubule network, induces cell cycle arrest, and results in microtubule cleavage, accompanied by cell death (apoptosis).

With regard to the antibody-drug conjugate (ADC), the anticancer drug should be stably bound to the antigen until the anti-cancer drug is delivered to the target cancer cell. The drug delivered to the target should be released from the antibody and induce the death of the target cell. For this purpose, the drug should be stably bound to the antibody, and at the same time, should exhibit sufficient cytotoxicity to induce the death of the target cell when released in the target cell.

In the present invention, the anti-MUC1 antibody or an antigen-binding fragment thereof and a cytotoxic substance including a drug such as an anti-cancer agent are bound to each other (for example, via a covalent bond, a peptide bond or the like) and thus can be used as a conjugate or a fusion protein (when a cytotoxic substance and/or labeling substance (marker) is protein). The cytotoxic substance may be any substance which is toxic to cancer cells, particularly solid cancer cells, and may be at least one selected from the group consisting of radioisotopes, cytotoxic compounds (small molecules), cytotoxic proteins, and anticancer drugs, but the present invention is not limited thereto. The cytotoxic protein is selected from the group consisting of ricin, saporin, gelonin, momordin, debouganin, diphtheria toxin, *pseudomonas* toxin, and the like, but the present invention is not limited thereto. The radioisotope may be at least one selected from the group consisting of 131I, 188Rh and 90Y, but the present invention is not limited thereto. The cytotoxic compound may be selected from the group consisting of duocarmycin, monomethyl auristatin E (MMAE), monomethyl auristatin F (MMAF), N2'-diacetyl-N2'-(3-mercapto-1-oxopropyl)maytansine (DM1), PBD (pyrrolobenzodiazepine) dimer, and the like, but is not limited thereto.

In the present invention, the antibody-drug conjugate may be obtained according to a method well-known in the art.

In the present invention, the antibody-drug conjugate may be characterized in that the antibody or antigen-binding fragment thereof is bound to the drug via a linker.

In the present invention, the linker may be a cleavable linker or a non-cleavable linker.

The linker is a site for linking the anti-MUC1 antibody to the drug. For example, the linker allows the drug to be released in a cleavable form under an intracellular condition, that is, through cleavage of the linker from the antibody in an intracellular environment.

The linker may be a peptide linker that can be cleaved by a cleavage agent present in an intracellular environment, for example, in the lysosome or endosome, and can be cleaved by intracellular peptidases or proteases, such as lysosome or endosome proteases. Generally, a peptide linker has at least two amino acid lengths. The cleavage agent may include cathepsin B, cathepsin D and plasmin, which hydrolyze the peptide to release the drug into the target cell. The peptide linker can be cleaved by a thiol-dependent protease cathepsin-B, which is highly expressed in cancer tissues, and may, for example, be a Phe-Leu or Gly-Phe-Leu-Gly linker. In addition, the peptide linker may, for example, be a Val-Cit linker or a Phe-Lys linker, which can be cleaved by an intracellular protease.

In the present invention, the cleavable linker is sensitive to pH and may be sensitive to hydrolysis at a certain pH value. Generally, the pH-sensitive linker is a linker that can be hydrolyzed under acidic conditions. Examples of acid-instable linkers that can be hydrolyzed in lysosomes may include hydrazone, semicarbazone, thiosemicarbazone, cis-aconitic amide, orthoester, acetal, ketal, and the like.

The linker may be cleaved under reducing conditions and may, for example, be a disulfide linker. A variety of disulfide bonds can be formed using N-succinimidyl-S-acetylthioacetate (SATA), N-succinimidyl-3-(2-pyridyldithio) propionate (SPDP), N-succinimidyl-3-(2-pyridyldithio)butyrate (SPDB) and N-succinimidyl-oxycarbonyl-alpha-methyl-alpha-(2-pyridyl-dithio)toluene (SMPT).

In the present invention, the drug and/or drug-linker may be randomly conjugated through the lysine of the antibody, or may be conjugated through cysteine that is exposed when the disulfide bond chain is reduced. In some cases, the linker-drug can be conjugated through cysteine present in a genetically engineered tag, e.g., a peptide or protein. The genetically engineered tag, e.g., peptide or protein, may include an amino acid motif that can be recognized, for example, by an isoprenoid transferase. The peptide or protein has a deletion at the carboxyl terminus of the peptide or protein or an addition at the carboxyl (C) terminus of the peptide or protein through a covalent bond of the spacer unit. The peptide or protein may be directly covalently bonded to an amino acid motif or may be linked to the amino acid motif through a covalent bond to the spacer unit. The amino acid spacer unit includes 1 to 20 amino acids and is preferably a glycine unit among them.

The linker may include a beta-glucuronide linker that is present in multiple copies in the lysosome, or is hydrolyzed by beta-glucuronidase that is overexpressed in some tumor cells. Unlike the peptide linker, this linker has an advantage of increasing the solubility of the antibody-drug composite when bound to a drug having high hydrophobicity due to the high hydrophilicity thereof.

In this regard, in the present invention, a beta-glucuronide linker disclosed in Korean Patent Publication No. 2015-0137015, for example, a beta-glucuronide linker including a self-immolative group, may be used.

In addition, the linker can be, for example, a non-cleavable linker, and the drug may be capable of being released merely through a single step of hydrolyzing the antibody to produce, for example, an amino-acid-linker-drug composite. This type of linker can be a thioether group or a maleimidocaproyl group, and can maintain stability in the blood.

In the present invention, the drug may be a chemotherapeutic agent, toxin, microRNA (miRNA), siRNA, shRNA or a radioactive isotope. The drug, as an agent having a pharmacological effect, may be conjugated to an antibody.

The chemotherapeutic agent may be a cytotoxic agent or an immunosuppressive agent. Specifically, the chemotherapeutic agent may include a microtubulin inhibitor, amitotic inhibitor, a topoisomerase inhibitor, or a chemotherapeutic agent capable of functioning as a DNA intercalator. The chemotherapeutic agent may also include an immunomodulatory compound, an anticancer agent, an antiviral agent, an antibacterial agent, an antifungal agent, an anthelmintic or a combination thereof.

For example, the drug may include at least one selected from the group consisting of maytansinoid, auristatin, aminopterin, actinomycin, bleomycin, thalidomide, camptothecin, N8-acetylspermidine, 1-(2 chloroethyl)-1,2-dimethyl sulfonyl hydrazide, esperamycin, etoposide, 6-mercaptopurine, dolastatin, trichothecene, calicheamicin, taxol, taxane, paclitaxel, docetaxel, methotrexate, vincristine, vinblastine, doxorubicin, melphalan, mitomycin A, mitomycin C, chlorambucil, duocarmycin, L-asparaginase, mercaptopurine, thioguanine, hydroxyurea, cytarabine, cyclophosphamide, ifosfamide, nitrosourea, cisplatin, carboplatin, mitomycin, dacarbazine, procarbazine, topotecan, nitrogen mustard, cytoxan, etoposide, 5-fluorouracil, bischloroethylnitrosourea (CNU), irinotecan, camptothecin, bleomycin, idarubicin, daunorubicin, dactinomycin, plicamycin, mitoxantrone, asparaginase, vinorelbine, chlorambucil, melphalan, carmustine, lomustine, busulfan, treosulfan, dacarbazine, etoposide, teniposide, topotecan, 9-aminocamptothecin, crisnatol, trimetrexate, mycophenolic acid, tiazofurin, ribavirin, 5-ethynyl-1-beta-Dribofuranosylimidazole-4-carboxamide (EICAR), hydroxyurea, deferoxamine, floxuridine, doxifluridine, raltitrexed, cytarabine (ara C), cytosine arabinoside, fludarabine, tamoxifen, raloxifene, megestrol, goserelin, leuprolide acetate, flutamide, bicalutamide, EB1089, CB1093, KH1060, verteporfin, phthalocyanine, photosensitizer Pe4, demethoxy-hypocrellin A, interferon-α, interferon-γ, tumor necrosis factor, gemcitabine, Velcade, revamid, Thalomid, lovastatin, 1-methyl-4-phenylpyridiniumion, staurosporine, actinomycin D, dactinomycin, bleomycin A2, bleomycin B2, peplomycin, epirubicin, pirarubicin, zorubicin, mitoxantrone, verapamil and thapsigargin, nucleases and toxins derived from bacteria or plants and animals, but the present invention is not limited thereto.

In the present invention, the drug may have a nucleophile group selected from the group consisting of amine, thiol, hydroxyl, hydrazide, oxime, hydrazine, thiosemicarbazone, hydrazine carboxylate and aryl hydrazide groups, which can react with an electrophilic group on the linker and the linker reagent to form a covalent bond.

In another aspect, the present invention relates to a bispecific antibody comprising the anti-MUC1 antibody or an antigen-binding fragment thereof.

The bispecific antibody refers to an antibody in which, among two arms of the antibody, one arm includes the anti-MUC1 antibody or an antigen-binding fragment thereof according to the present invention, and the other includes an antibody or an antigen-binding fragment thereof that is specifically binds to an antigen, other than the MUC1, preferably a cancer-associated antigen or an immune checkpoint protein antigen, or an immune-effector cell-associated antigen.

The antigen bound to the antibody other than the anti-MUC1 antibody included in the bispecific antibody according to the present invention is preferably selected from the cancer-associated antigens or immune checkpoint protein antigens including Her2, EGFR, VEGF, VEGF-R, CD-20, MUC16, CD30, CD33, CD52, PD-1, PD-L1, CTLA4, BTLA4, EphB2, E-selectin, EpCam, CEA, PSMA, PSA, ERB3, c-MET, and the like, and is preferably selected from the immune-effector cell-associated antigens including TCR/CD3, CD16(FcγRIIIa) CD44, CD56, CD69, CD64 (FcγRI), CD89, CD11b/CD18(CR3) and the like, but the present invention is not limited thereto.

In another aspect, the present invention relates to a pharmaceutical composition for preventing and/or treating MUC1-associated disease comprising the anti-MUC1 antibody or an antigen-binding fragment thereof, the antibody-drug conjugate or the bispecific antibody.

The MUC1-associated disease may be a disease associated with expression or overexpression of MUC1, expression on all surfaces of cells of MUC1, and/or reduction of glycosylation of MUC1 protein compared to normal cells, for example, cancer. The normal cells may be non-tumor cells. Accordingly, the MUC1-associated disease is preferably a cancer or tumor, but the disease is not limited thereto.

The term "cancer" or "tumor" typically refers to or means the physiological condition of a mammal characterized by uncontrolled cell growth/proliferation.

The cancer or carcinoma that can be treated with the composition of the present invention is not particularly limited, and includes both solid cancer and blood cancer. Examples of such kinds of cancer include, but are not limited to, skin cancer such as melanoma, liver cancer, hepatocellular carcinoma, stomach cancer, breast cancer, lung cancer, ovarian cancer, bronchial cancer, nasopharyngeal cancer, laryngeal cancer, pancreatic cancer, bladder cancer, colorectal cancer, colon cancer, cervical cancer, brain cancer, prostate cancer, bone cancer, thyroid cancer, pituitary cancer, kidney cancer, esophageal cancer, biliary cancer, testicular cancer, rectal cancer, head and neck cancer, cervical cancer, ureteral cancer, osteosarcoma, neuroblastoma, fibrosarcoma, rhabdomyosarcoma, astrocytoma, and glioma.

More preferably, the cancer is characterized in that MUC1 protein is expressed, and may be breast cancer, pancreatic cancer, prostate cancer, lung cancer, thyroid cancer, stomach cancer, ovarian cancer, colorectal cancer, liver cancer, gallbladder cancer, kidney cancer, cervical cancer, or bladder cancer, but is not limited thereto. The cancer may be a primary cancer or a metastatic cancer.

The MUC1-associated disease may be non-alcoholic steatohepatitis (NASH) or TGF-β-mediated immune disease, but is not limited thereto.

In one embodiment of the present invention, in the pharmaceutical composition, method and use for preventing and/or treating cancer, the anti-MUC1 antibody or an antigen-binding fragment thereof may be provided as a single active ingredient, may be administered in conjunction with a cytotoxic substance such as an anti-cancer agent, or may be provided in the form of an antibody-drug conjugate (ADC) conjugated with a cytotoxic substance such as an anti-cancer agent.

In addition, the anti-MUC1 antibody or antigen-binding fragment thereof according to the present invention and the pharmaceutical composition comprising the anti-MUC1 antibody can be used in combination with a conventional therapeutic agent. That is, the anti-MUC1 antibody or antigen-binding fragment thereof according to the present invention and the pharmaceutical composition comprising the same can be used simultaneously or sequentially with a conventional therapeutic agent such as an anti-cancer agent.

In another aspect, the present invention relates to a method for preventing and/or treating MUC1-associated disease comprising administering a therapeutically effective amount of the anti-MUC1 antibody or antigen-binding fragment thereof or the antibody-drug conjugate to a patient in need of prevention or treatment of MUC1-associated disease. The method for preventing and/or treating MUC1-associated disease may further include examining the patient in need of prevention or treatment of MUC1-associated disease before the administration.

The use of an antibody conjugate for local delivery of the drug in the composition allows the drug to be delivered to cells expressing the antigen targeted with the anti-MUC1 antibody.

The pharmaceutical composition may further contain a pharmaceutically acceptable carrier. The pharmaceutically acceptable carrier may be one that is commonly used for the preparation of drugs and may include at least one selected from the group consisting of lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil, and the like, but the present invention is not limited thereto. Also, the pharmaceutical composition may further contain at least one selected from the group consisting of a diluent, an excipient, a lubricant, a wetting agent, a sweetening agent, a flavoring agent, an emulsifying agent, a suspending agent and a preservative, which are commonly used for the preparation of pharmaceutical compositions.

The pharmaceutical composition may be administered orally or parenterally. For parenteral administration, the pharmaceutical composition may be administered through intravenous injection, subcutaneous injection, intramuscular injection, intraperitoneal injection, intradermal administration, intranasal administration, intrapulmonary administration, intrarectal administration, or topical administration to lesion sites or the like. Upon oral administration, proteins or peptides are digested, so that an oral composition may be coated with an active drug or formulated so as to protect the same from degradation in the stomach. In addition, the composition may be administered using any device capable of delivering the active substance to target cells.

The content or dose of the anti-MUC1 antibody or antigen-binding fragment thereof in the pharmaceutical composition may vary depending on factors such as the formulation method, administration method, and age, body weight, gender, pathological conditions, diet, administration time, administration interval, administration route, excretion rate and responsiveness of the patient. For example, the daily dose of the anti-MUC1 antibody or an antigen-binding fragment thereof may be within the range of 0.001 to 1,000 mg/kg, specifically 0.01 to 100 mg/kg, and more specifically 0.1 to 50 mg/kg, even more specifically 0.1 to 20 mg/kg, but the present invention is not limited thereto. The daily dose may be prepared by formulation into a single dosage form with a unit dose, formulation in an appropriate dose, or packaging in a multi-dose container.

The pharmaceutical composition may be in the form of a solution, a suspension, a syrup or an emulsion in an oil or aqueous medium, or may be formulated in the form of an extract, a powder, a granule, a tablet or a capsule. The pharmaceutical composition may further contain a dispersant or a stabilizer.

The patient administered with the pharmaceutical composition may be a mammal including a primate including a human, a monkey or the like, or a rodent including a mouse, a rat or the like.

In the present specification, the treatment of cancer may mean all anti-cancer activities to prevent, ameliorate or relieve aggravation of the symptoms of cancer, or to partially or entirely eliminate cancer, such as inhibition of proliferation of cancer cells, death of cancer cells, or inhibition of cancer cell metastasis.

In another aspect, the present invention relates to the use of the anti-MUC1 antibody or an antigen-binding fragment thereof for preventing or treating cancer.

In another aspect, the present invention relates to the use of the anti-MUC1 antibody or an antigen-binding fragment thereof for preparing a preventive or therapeutic agent for cancer.

The anti-MUC1 antibody or antigen-binding fragment thereof specifically binds to MUC1 protein, particularly to the MUC1-C-terminal extracellular domain, and thus can be used to detect or identify the MUC1 protein or MUC1-C-terminal extracellular domain. Thus, in another aspect, the present invention relates to a composition for detecting a MUC1 protein, such as a MUC1-C-terminal extracellular domain, comprising the anti-MUC1 antibody or antigen-binding fragment thereof, and a method for detecting MUC1 comprising treating a biological sample with the anti-MUC1 antibody or an antigen-binding fragment thereof.

The detection method may further include identifying whether or not an antigen-antibody reaction occurs, after the treatment. In the detection method, when the antigen-antibody reaction is detected, MUC1, e.g., a MUC1-C-terminal extracellular domain, may be determined to be present in the biological sample. Thus, the detection method may further include determining that MUC1 is present in the biological sample when an antigen-antibody reaction is detected, after the identification. The biological sample may be selected from the group consisting of cells, tissues, body fluids, cultures thereof and the like, obtained (isolated) from a mammal such as a human (such as a cancer patient).

The expression of MUC1 protein, such as C-terminal region of MUC1 protein (or the SEA domain or MUC1-C-terminal extracellular domain of the MUC1 protein) is associated with several diseases, such as cancer. Thus, in another aspect, the present invention relates to a composition for detecting or diagnosing MUC1 protein-associated disease, such as cancer, comprising the anti-MUC1 antibody or antigen-binding fragment thereof, and a method for detecting or diagnosing cancer, or a method for providing information for detecting or diagnosing cancer comprising administering the anti-MUC1 antibody or antigen-binding fragment thereof to a biological sample isolated from a subject.

The detection or diagnosis method may further include identifying whether or not an antigen-antibody reaction occurs, after the treatment. In the method, when an antigen-antibody reaction is detected, a MUC1-associated disease, such as cancer, may be determined to be present in the biological sample or the patient from which the biological sample is derived. Thus, the method may further include determining that the biological sample or the patient from which the biological sample is derived is a patient having a MUC1-associated disease, such as cancer, when an antigen-antibody reaction is detected, after the identification. The biological sample may be selected from the group consisting of cells, tissues, body fluids, cultures thereof and the like, obtained (isolated) from a mammal such as a human (such as a cancer patient).

The identifying whether or not the antigen-antibody reaction occurs can be carried out through various methods known in the art, for example, a conventional enzyme reaction, fluorescence, luminescence and/or radiation detection, specifically, by a method selected from the group consisting of immunochromatography, immunohistochemistry, enzyme-linked immunosorbent assay (ELISA), radioimmunoassay (RIA), enzyme immunoassay (EIA), fluorescence immunoassay (FIA), luminescence immunoassay (LIA), Western blotting, microarray, immunoprecipitation assay, and the like, but the present invention is not limited thereto.

In this case, the anti-MUC1 antibody or antigen-binding fragment thereof may further include a marker. The marker may be at least one selected from the group consisting of radioactive isotopes, fluorescent substances, chromogen and dyeing substances. The marker may be bound (linked) to the antibody or antigen-binding fragment by a conventional method (for example, a chemical bond such as a covalent bond, coordination bond or ionic bond). The binding of the antibody (or antigen-binding fragment) to the marker may be in accordance with techniques well-known in the art.

In one embodiment of the present invention, the monoclonal antibody to MUC1 is produced by cloning the C-terminal region of MUC1 from a breast cancer cell line and expressing the same in Rosetta competent cells. The C-terminal region of MUC1 was formulated with CpG-DNA (e.g., MB-ODN 4531 (O)), encapsulated in a DOPE:CHEMS complex, and then used for mouse immunization. The production of MUC1-specific monoclonal antibodies was significantly increased when mice were immunized with the [C-terminal region of MUC1]-[MB-ODN 4531 (O)]-[DOPE:CHEMS] complex. The anti-hMUC1-SEA monoclonal antibody was also obtained by fusing spleen cells obtained from mice immunized with the [hMUC1-SEA]-[MB-ODN 4531(O)]-[DOPE:CHEMS] complex with SP2/0 cells.

Thus, in another aspect, the present invention relates to an immunogenic composition comprising the C-terminal region of MUC1, the SEA domain of MUC1, or the C-terminal extracellular domain of MUC1. Another embodiment provides an immunogenic composition comprising a complex comprising (1) a C-terminal region of MUC1, a SEA domain of MUC1, or a C-terminal extracellular domain of MUC1 and (2) CpG-DNA encapsulated within the liposome. The immunogenic composition means a composition that has the ability to produce an antibody by inducing an immune response when injected (inoculated) into a living organism.

In the present invention, the liposome may be a cationic liposome, for example, a mixture of dioleoyl phosphatidylethanolamine (DOPE) and cholesteryl hemisuccinate (CHEMS) at a molar ratio of 1:0.5 to 1:2, more specifically 1:0.67 to 1:1.5 (DOPE:CHEMS), for example, a molar ratio of about 1:1, or may be a product (such as a solvent-free lipid film) obtained therefrom, but is not limited thereto.

In the present invention, the CpG-DNA refers to oligodeoxynucleotide (ODN) containing a total of 10 to 20 nucleotides including one or more, for example, one to three, CpG motifs. In one embodiment of the present invention, the CpG-DNA may include, but is not limited to, a nucleic acid sequence of "AGCAG<u>CG</u>TT<u>CG</u>TGT<u>CG</u>GCCT" (SEQ ID NO: 11).

The liposome and the oligodeoxynucleotide can function as an adjuvant. The adjuvant helps to recognize an antigen more easily along with the immune system and improves the immune response. Bacterial DNA containing synthetic oligodeoxynucleotides (ODN) and unmethylated CpG dinucleotides flanked by specific base sequences have important immunomodulatory effects on B lymphocytes, natural killer cells, macrophages and dendritic cells.

It has been shown that cationic liposomes (e.g., lipofectamine, and phosphatidyl-beta-oleoyl-gamma-palmitoyl ethanolamine (DOPE):cholesterol hemisuccinate (CHEMS)) increase antibody production, antibody delivery and CTL response. Therefore, the CpG-DNA (lipoplex(O)) encapsulated in the DOPE:CHEMS (1:1 ratio) complex can promote an effective immune response in human and mouse cells.

In another aspect, the present invention relates to a method for producing an anti-MUC1-SEA monoclonal antibody comprising inoculating a mammal, for example, a mouse, with a C-terminal region of MUC1, an SEA domain of MUC1, or a C-terminal extracellular domain of MUC1, or a complex comprising (1) a C-terminal region of MUC1, a SEA domain of MUC1, or a C-terminal extracellular domain of MUC1 and (2) CpG-DNA encapsulated within the liposome. The method for producing an anti-MUC1-SEA monoclonal antibody may further include isolating and purifying the antibody from the serum of the mouse by a conventional method after the inoculation.

In another aspect, the present invention relates to a nucleic acid encoding the anti-MUC1 antibody according to the invention. As used herein, the nucleic acid may be present in a cell or a cell lysate, or may be present in a partially purified form or in a substantially pure form. The nucleic acid may be "isolated" or "become substantially pure" when purified from other cellular components or other contaminants, for example, from nucleic acids or proteins of other cells, by standard techniques including, for example, alkaline/SDS treatment, CsCl banding, column chromatography, agarose gel electrophoresis and other techniques well known in the art. The nucleic acid of the present invention may be, for example, DNA or RNA, and may or may not include an intron sequence.

In the present invention, the nucleic acid encoding the anti-MUC1 antibody may include at least one sequence selected from the group consisting of SEQ ID NO: 34 to SEQ ID NO: 45. Specifically, the polynucleotide sequence encoding the heavy chain of the antibody according to the present invention is represented by SEQ ID NOS: 34 to 39 and/or the polynucleotide sequence encoding the light chain of the antibody according to the present invention is represented by SEQ ID NOS: 40 to 45.

In another aspect, the present invention relates to a recombinant expression vector comprising the nucleic acid.

For expression of the anti-MUC1 antibody or antigen-binding fragment thereof according to the present invention, DNA encoding partial or full-length light or heavy chains may be prepared through standard molecular biology techniques (e.g., PCR amplification or cDNA cloning using hybridoma expressing the desired antibody), and the DNA can be "operably linked" to a transcription and translation control sequence and inserted into an expression vector.

As used herein, the term "operably linked" may mean that the gene encoding the antibody is ligated into the vector such that the transcriptional and translational control sequences within the vector serve the intended function of regulating the transcription and translation of the antibody gene. The expression vector and expression control sequences are selected so as to be compatible with the host cell used for expression. The light-chain gene of the antibody and the heavy-chain gene of the antibody are inserted into separate vectors, or both genes are inserted into the same expression vector. Antibodies are inserted into expression vectors by standard methods (e.g., ligation of complementary restriction enzyme sites on the antibody gene fragment and vector, or blunt-end ligation when no restriction enzyme site is present). In some cases, the recombinant expression vector can encode a signal peptide that facilitates secretion of the antibody chain from the host cell. The antibody-chain gene may be cloned into a vector such that the signal peptide is attached to the amino terminus of the antibody-chain gene in accordance with the frame. The signal peptide may be an immunoglobulin signal peptide or a heterologous signal peptide (i.e., a signal peptide derived from a protein other than immunoglobulin). In addition, the recombinant expression vector has a control sequence that controls the expression of the antibody-chain gene in the host cell. The term "control sequence" may include promoters, enhancers, and other expression control elements (e.g., polyadenylation signals) that control the transcription or translation of the antibody-chain gene. Those skilled in the art will appreciate that the design of the expression vector can be varied by selecting different control sequences depending on factors such as selection of the host cell to be transformed and the level of expression of the protein.

In another aspect, the present invention relates to a host cell comprising the nucleic acid or the vector. The host cell according to the present invention is preferably selected from the group consisting of animal cells, plant cells, yeast, *Escherichia coli* and insect cells, but is not limited thereto.

More specifically, the host cell according to the present invention may be a prokaryotic cell, such as *Escherichia coli, Bacillus subtilis, Streptomyces* sp., *Pseudomonas* sp., *Proteus mirabilis*, or *Staphylococcus* sp. The host cell may be a eukaryotic cell selected from fungi such as *Aspergillus* sp., yeast such as *Pichia pastoris, Saccharomyces cerevisiae, Schizosaccharomyces* sp., and *Neurospora crassa*, other lower eukaryotic cells, and cells of higher eukaryotes such as cells from insects.

The host cell may also be derived from plants or mammals. Preferably, useful host cells may include, but are not limited to, monkey kidney cells (COST), NSO cells, SP2/0, Chinese hamster ovary (CHO) cells, W138, baby hamster kidney (BHK) cells, MDCK, myeloma cell lines, HuT 78 cells, HEK293 cells and the like. Particularly preferably, useful host cells are CHO cells.

The nucleic acid or the vector is transfected into a host cell. "Transfection" may be carried out using various techniques commonly used to introduce foreign nucleic acids (DNA or RNA) into prokaryotic or eukaryotic host cells, for example, electrophoresis, calcium phosphate precipitation, DEAE-dextran transfection or lipofection. Various expression host/vector combinations may be used to express the anti-glypicans 3 antibody according to the present invention. Suitable expression vectors for eukaryotic hosts include, for example, but are not limited to, expression control sequences derived from SV40, cow papillomavirus, adenovirus, adeno-associated virus, cytomegalovirus and retrovirus. Expression vectors that can be used for bacterial hosts include bacterial plasmids obtained from *Escherichia coli* (*E. coli*), such as pET, pRSET, pBluescript, pGEX2T, pUC vectors, col E1, pCR1, pBR322, pMB9 and derivatives thereof, plasmids having a wide host range such as RP4, phage DNA that can be exemplified by a wide variety of phage lambda derivatives such as λgt10, λgt11 and NM989, and other DNA phages such as M13 and filamentous single-stranded DNA phages. Expression vectors useful for yeast cells include 2p plasmids and derivatives thereof. The vector useful for insect cells is pVL 941.

In another aspect, the present invention relates to a method for producing the anti-MUC1 antibody or an antigen-binding fragment thereof according to the present invention, comprising culturing a host cell to express the anti-MUC1 antibody or an antigen-binding fragment thereof according to the present invention.

When a recombinant expression vector capable of expressing the anti-MUC1 antibody or antigen-binding fragment thereof is introduced into a mammalian host cell, the antibody can be produced by culturing the host cell for a period of time sufficient to allow expression of the antibody in the host cell, more preferably, culturing the host cells for a period of time sufficient to allow the antibody to be secreted into the culture medium.

In some cases, the expressed antibody may be separated from the host cell and purified to homogeneity. The separation or purification of the antibody can be carried out using separation and purification methods used for conventional proteins, for example, chromatography. Such chromatography may include, for example, affinity chromatography involving a protein A column or a protein G column, ion exchange chromatography, or hydrophobic chromatography. The antibody can be separated and purified by performing chromatography in combination with filtration, ultrafiltration, salting out, dialysis and the like.

Hereinafter, the present invention will be described in more detail with reference to the following examples. However, it will be obvious to those skilled in the art that the following examples are provided only for illustration of the present invention and should not be construed as limiting the scope of the present invention.

Example 1: Production of Recombinant hMUC1-C Protein

Human cDNA encoding the MUC1-C terminus (hereinafter referred to as "hMUC1-C protein"; a protein including 192 amino acids from position 961 to position 1152 of P15941, of which 1034-1152 aa is the MUC-SEA domain) was obtained from MCF7 cells and were then amplified by RT-PCR using the following primer sets:

Sense primer: hMUC1 C-Nco I-S3 5'-CC ATG GCC TCA GGC TCT GCA TC-3'(SEQ ID NO: 12); and Anti-sense primer: hMUC1 C-Xho I-AS4 5'-CTC GAG AGA CTG GGC AGA GAA AGG AAA T-3'(SEQ ID NO: 13).

The obtained hMUC1-C terminal protein-encoding sequence was identified by DNA sequencing, and the result showed that the sequence is the same as the nucleotide sequence including 576 nucleotides from the nucleotide at position 2954 to the nucleotide at position 3529 of GenBank Accession No. J05582.1 (SEQ ID NO: 26).

Example 2: Expression and Purification of Recombinant hMUC1-C(rhMUC1-C) Protein

The amplified cDNA fragment was cloned into an expression vector pET-22b (Novagen, Darmstadt, Germany) containing a C-terminal His-tag. The obtained plasmids were transformed into competent cells of *Escherichia coli* Rosetta™ (Invitrogen, Carlsbad, Calif.), and were induced at 37° C. using 1 mM isopropyl-D-1-thioglucopyranoside (IPTG, Sigma-Aldrich, Saint Louis, Mo.) for 8 hours. The obtained cells were dissolved by sonication in ice-phase lysis buffer (50 mM Tris-HCl, 100 mM NaCl, 5 mM EDTA, 0.5% Triton X 100, 1 g/ml lysozyme, proteinase inhibitor cocktail). After centrifugation, the inclusion body fraction was mixed with buffer B (100 mM NaH$_2$PO$_4$, 10 mM Tris-HCl, 8 M urea, pH 8.0) and purified using a Ni-NTA agarose (Qiagen, Valencia, CA.) system. The resulting mixture was loaded onto a Ni-NTA column and washed with wash buffer C (100 mM NaH$_2$PO$_4$, 10 mM Tris-HCl, 8 M urea, pH 6.3). The bound proteins were eluted with elution buffer (100 mM NaH$_2$PO$_4$, 10 mM Tris-HCl, 8 M urea, pH 4.5) and analyzed by SDS-PAGE and Western blotting. Western blotting was performed using an anti-His-tag antibody (Santa Cruz).

Example 3: Preparation of Lipoplex (O) Complex

MB-ODN 4531 includes 20 bases containing three CpG motifs (underlined) (AGCAG<u>CG</u>TT<u>CG</u>TGT<u>CG</u>GCCT: SEQ ID NO: 11). The CpG ODN (oligodeoxynucleotide) (hereinafter referred to as "CpG-DNA 4531 (O)") was purchased from Samchully Pharm (Korea, Seoul) and Geno-Tech (Daejeon, Korea). Phosphatidyl-beta-oleoyl-gamma-palmitoyl ethanolamine (DOPE) and cholesterol hemisuccinate (CHEMS) were mixed in ethanol at a molar ratio of 1:1 and then evaporated with a nitrogen gas to obtain a solvent-free lipid film. The solvent-free lipid film was resuspended in the same volume of a mixture containing 50 µg of aqueous CpG-DNA 4531 (O) and 50 µg of rhMUC1-C protein (Example 2) and vigorously stirred at room temperature for 30 minutes to produce CpG-DNA 4531 (O) and rhMUC1-C proteins co-encapsulated in the DOPE and CHEMS complex. "Lipoplex (O) complex" refers to CpG-DNA 4531 (O) encapsulated in the DOPE and CHEMS complex. After adjusting the pH to 7.0, the rhMUC1-C protein and the lipoplex (O) complex were sonicated for 30 seconds with an ultrasonic generator, and the resulting solution was filtered through a 0.22 µm filter and freeze-thawed three times with liquid nitrogen, and was then used in the following experiment.

Example 4: Preparation of Animals

Four-week-old female BALB/c mice (OrientBio, Inc., Seoul, Korea) and BALB/cAnNCri-nu/nu mice (four-week-old) were purchased from Nara Biotech, Inc (Seoul, Korea). The mice were maintained at 20 to 25° C. and at a humidity of 32 to 37% under aseptic conditions with no specific pathogen. All animal experiment procedures were approved by the Institutional Animal Care and Use Committee of Hallym University and conducted in accordance with the Guide for the Care and Use of Laboratory Animals of the National Veterinary Research & Quarantine Service of Korea. The mice were sacrificed through isoflurane inhalation and every effort was made to minimize pain.

Example 5: Immunization of Mice

BALB/c mice were immunized through intraperitoneal injection four times at 10-day intervals with a liposome complex including a complex having 50 µg of rhMUC1-C protein and 50 µg of CpG-DNA 4531 co-encapsulated in phosphatidyl-beta-oleoyl-gamma-palmitoylethanolamine: cholesterol hemisuccinate (DOPE:CHEMS complex).

Example 6: Antigen-Specific Ig ELISA

The total amount of rhMUC1-C-specific IgG was measured by ELISA. A 96-well immunoplate was coated with 10 µg/ml of rhMUC1-C protein (Example 2) and blocked with bovine serum albumin (BSA) in PBS-T (PBS containing 0.1% (v/v) Tween-20). The mouse serum immunized in Example 5, hybridoma cell culture supernatant, or purified antibody was diluted with PBS-T and cultured at room temperature for 2 hours. The plate was washed 3 times with PBS-T and cultured with a goat anti-mouse IgG HRP-conjugated secondary antibody for 1 hour. The plate was developed using TMB substrate solutions A and B (1:1 ratio) (Kirkegaard and Perry Laboratories, Gaithersburg, Md., USA), the absorbance was measured at 450 nm using a Spectra Max 250 microplate reader (Molecular Devices, Sunnyvale, USA), and a colorimetric assay was performed.

Example 7: Preparation and Purification of Anti-hMUC1 Monoclonal Antibody

The spleen cells from mice immunized with rhMUC1-C protein in Example 5 were fused with SP2/0 myeloma cells (ATCC) using polyethylene glycol (PEG, Sigma-Aldrich). The fused cells were cultured and selected as a hypoxanthine-aminopterin-thymidine (HAT, Sigma-Aldrich) medium. The culture supernatant of the selected hybridoma cells was subjected to testing for binding to rhMUC1-C protein through ELISA and hybridoma cells, which were positive for binding, i.e., produced rhMUC1-C protein-specific antibody, were screened. Hybridoma clones were screened according to standard hybridoma technology (Yokoyama et al. 2006). The obtained hybridoma clone (KCLRF-BP-00395; hereinafter, the hybridoma cells or antibodies produced therefrom will be referred to as "hMUC1-1H7") was cultured in hypoxanthine-thymidine (HT) medium. ELISA-positive hybridoma cell populations were subcloned. For monoclonal antibody production, hybridoma cells (hMUC1-1H7 clones) were intraperitoneally injected into the mice at the initial stage and 10 days after intraperitoneal injection. After 10 days, the peritoneal fluid was collected and centrifuged at 3,000 rpm for 30 minutes. The supernatant was purified using an anti-hMUC1 monoclonal antibody binding to the rhMUC1-C protein using Protein-A chromatography (Repligen, Waltham, Mass.).

Example 8: Identification of IgG Isotype of Anti-hMUC1 Monoclonal Antibody

In order to measure the IgG isotype of the anti-hMUC1 monoclonal antibody obtained in Example 7, a 96-well immunoplate (Nalgene Nunc International, Penfield, USA) was coated with 1 µg/ml of hMUC1-C protein and blocked with 0.05% Tween-20 in PBS containing 1% BSA (PBST).

Anti-hMUC1-C monoclonal antibodies were added to the top row of each plate, and a series of 1:4 dilutions in PBST were placed in the next row. The plate was incubated at room temperature for 2 hours and washed with PBST. Then, anti-mouse total IgG, IgG1, IgG2a, IgG3b, IgG3 antibodies conjugated with horseradish peroxidase (HRP: BD Pharmingen) were added to each well (1:500 dilution) and cultured at room temperature for 1 hour. The total amount was analyzed using TMB substrate solutions A and B (1:1 ratio, Kirkegaard and Perry Laboratories, Gaithersburg, Md.) and the absorbance at 450 nm was measured using Spectra Max 250 microplate reader (Molecular Devices, Sunnyvale, Calif., USA).

Example 9: Reactivity Test of Anti-hMUC1-SEA Monoclonal Antibody

Example 9-1: Cell Culture

Human breast cancer cell lines (MCF-7, MDA-MB-231) and pancreatic cancer cell lines (Capan-2, CFPAC-1) were purchased from the American Type Culture Collection (ATCC, Manassas, Va.), and human breast cancer cell lines (T47D, ZR75-1) and pancreatic cancer cell lines (Capan-1, PANC-1) were purchased from the Korean Cell Line Bank (KCLB, Seoul, Korea).

The MCF-7 cells were cultured in Eagle's Minimum Essential Medium supplemented with 0.01 mg/ml of human recombinant insulin; the MDA-MB-231 cells were cultured in Leibovitz's L-15 medium (Thermo Fisher Scientific); and the T47D, ZR75-1 and Capan-1 cells were cultured in RPMI-1640 medium (Thermo Fisher Scientific). The Capan-2 cells were cultured in McMcoy's 5A medium (Thermo Fisher Scientific), the CFPAC-1 cells were cultured in Iscove's modified Dulbecco's medium (IMDM, Thermo Fisher Scientific), and the PANC-1 cells were cultured in Dulbecco's modified Eagle's medium (DMEM, Thermo Fisher Scientific). All media used herein were supplemented with 10% (w/v) fetal bovine serum (FBS, Thermo Fisher Scientific), 100 U/ml of penicillin, and 100 mg/ml of streptomycin. The MCF-7, T47D, ZR75-1, Capan-1, Capan-2, CFPAC-1 and PANC-1 cells were cultured in the presence of 5% $CO_2$ at 37° C. and the MDA-MB-231 cells were cultured in the absence of $CO_2$ at 37° C.

Example 9-2: Preparation of Antibodies for Testing

Commercially available anti-MUC1-CT and anti-MUC1-CT2 antibodies were obtained from Abcam (Cambridge, UK) in order to detect MUC1 from cells through Western blotting and immunoprecipitation. The anti-MUC1-CT and anti-MUC1-CT2 antibodies recognize the cytoplasmic tail region of MUC1. The anti-beta-actin antibody was purchased from Sigma-Aldrich.

Example 9-3: Western Blotting Analysis

The cells were dissolved in a lysis buffer (20 mM Tris-HCl, pH 8.0, 150 mM NaCl, 5 mM EDTA, 100 mM NaF, 2 mM $Na_3Vo_4$, protease inhibitor cocktail, 1% (w/v) NP-40) and centrifuged at 4° C. at 14,000 rpm for 20 minutes. The same amount of protein was separated in a 4-12% Bis-Tris gradient gel (Thermo Fisher Scientific) and transferred to a nitrocellulose membrane blocked with 3% (w/v) BSA in PBS-T at room temperature for 1 hour. The nitrocellulose membrane was incubated overnight at 4° C. with the anti-hMUC1 antibody (hMUC1-1H7; Example 7), the anti-MUC1-CT antibody (Abacam, EPR1023), the anti-MUC1-CT2 antibody (Abcam, ab80952), or the anti-beta-actin antibody (Sigma-Aldrich). Immunoreactive proteins were measured using a secondary antibody conjugated with horseradish peroxidase and an enhanced chemiluminescent reagent (Thermo Fisher Scientific).

Example 9-4: Immunoprecipitation Assay

The cell lysis buffer (20 mM Tris-HCl, pH 8.0, 150 mM NaCl, 5 mM EDTA, 100 mM NaF, 2 mM $Na_3Vo_4$, protease inhibitor cocktail, 1% (w/v) NP-40) was incubated at 4° C. overnight with the anti-hMUC1 antibody. Protein A beads were added to the mixture and cultured at 4° C. for 1 hour. The immunocomplex collected by centrifugation were washed and analyzed by Western blotting. The membrane was cultured with the anti-hMUC1 antibody (hMUC1-1H7), the anti-MUC1-CT antibody (Abacam, EPR1023), the anti-MUC1-CT2 antibody (Abcam, ab80952), or the anti-beta-actin antibody (Sigma-Aldrich).

Example 9-5: Deglycosylation Assay

Cell lysates from T47D cells were extracted with lysis buffer (0.5% (w/v) SDS, 1% (w/v) beta-mercaptoethanol) and boiled at 100° C. for 10 minutes. Then, the sample was cultured with PNGase F (Elpis-Biotech, Daejeon, Korea) at 37° C. for 2 hours and boiled at 100° C. for 10 minutes. The obtained sample was diluted with lysis buffer and immunoprecipitated with the anti-hMUC1 monoclonal antibody. The resulting immune complex was analyzed by Western blotting with the anti-MUC-CT antibody or anti-MUC1-CT2 antibody.

Example 9-6: Confocal Microscopy

The cells were cultured on a glass cover slip coated with poly-L-lysine in a 12-well culture plate. For cell surface staining, the cells were fixed with 4% (w/v) paraformaldehyde, blocked with 3% (w/v) BSA and stained with anti-hMUC1 antibody on ice for 2 hours. For intracellular staining, the cells were fixed with 4% (w/v) paraformaldehyde, permeabilized with 0.1% (w/v) Triton X-100, blocked with 3% (w/v) BSA, and stained at room temperature with anti-hMUC1 antibody for 2 hours. After washing with PBS-T, the obtained cell samples were cultured with Alexa Fluor 488-conjugated secondary antibody (Invitrogen, Eugene, Oreg.) for 1 hour. Cell nuclei were stained with Hoechst 33258. All cell samples were mounted on and observed with a confocal laser-scanning microscope system (CLSM, LSM 710, Carl Zeiss, Jena, Germany).

Example 9-7: Internalization Assay

The anti-hMUC1 monoclonal antibody was labeled with DyLight 488 in accordance with the manufacturer's instructions (Thermo Fisher Scientific). Breast cancer cells and pancreatic cancer cells were treated with DyLight 488-labeled anti-hMUC1 antibody and incubated at 37° C. for an indicated time. Fluorescence signals generated from cells with internalized antibodies were detected with CLSM (LSM 710, Carl Zeiss).

Example 10: Cloning of Variable Regions of Anti-hMUC1 Monoclonal Antibody

The anti-hMUC1 monoclonal antibody (hMUC1-1H7; Example 7) was cultured using a mouse monoclonal antibody isotype typing kit (Dipstick format, Bibco BRL or Roche, Mannheim, Germany). Total RNA was extracted from the hybridoma cells using an RNeasy Mini Kit (Qiagen) to produce cDNA. In order to clone the heavy-chain variable region and the light-chain variable region ($V_H$ and $V_L$) of the anti-hMUC1 monoclonal antibody generated from hMUC1-1H7, the resulting cDNA was amplified using Vent polymerase (NEB) having the following set of primers:

```
Primer for heavy chain:
IGG1(5'-GGA AGA TCT ATA GAC AGA TGG GGG TGT CGT TTT

GGC-3'; SEQ ID NO: 14)
and

5'MH2(5'-CTT CCG GAA TTC SAR GTN MAG CTG SAG SAG

TCW GG-3'; SEQ ID NO: 15)

Primer for light chain (kappa chain):
3'Kc(5'-GGT GCA TGC GGA TAC AGT TGG TGC AGC ATC-3';

SEQ ID NO: 16)
and

5'Mk(5'-GG GAG CTC GAY ATT GTG GTS ACM CAR WCT

MCA-3'; SEQ ID NO: 17).
```

A standard PCR reaction was performed for 25 cycles. The resulting PCR product was directly ligated to pGEM-T Easy Vector (Promega). Cloned mouse Ig inserts were analyzed by DNA sequencing.

Figure 8A:
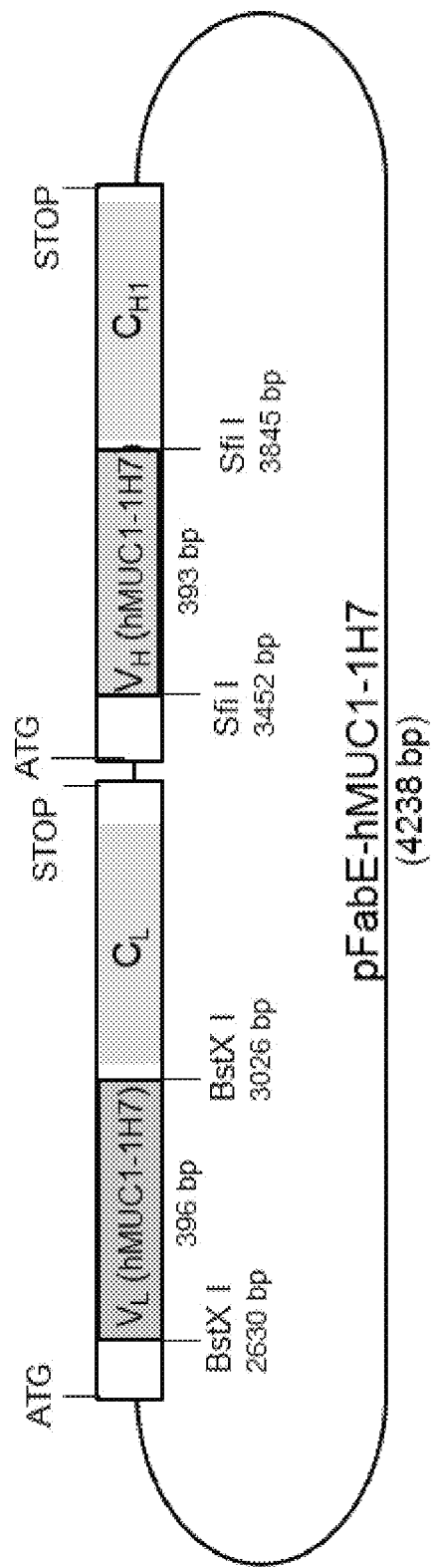
FIG. 8a is a cleavage map schematically showing the recombinant expression plasmid pFabE-hMUC1-1H7.

Example 11: Expression of Antigen-Binding Fragment (Fab) of Anti-hMUC1 Monoclonal Antibody The sequences encoding the light-chain variable region and the heavy-chain variable region (VH and VL) of the anti-hMUC1 monoclonal antibody (hMUC1-1H7; Example 7) were amplified and sub-cloned into the bacterial expression vector FabE using SfiI and BstXI, respectively (Jeon et al., Mol. Immunol. 44: 827-836 (2007), Kwon et al., Oncol. Rep. 18: 513-517 (2007)), and the recombinant expression plasmid thus obtained was designated as "pFabE-hMUC1-1H7" (FIG. 8a).

The primers used herein were as follows.

```
Primer for amplification of heavy-chain variable
region encoding sequence (393 bp):
Forward primer:
                                          (SEQ ID NO: 18)
5'-ggc cca gcc ggc cat ggc cSA RGT NMA GCT GSA GSA

GTC WGG-3';

Reverse primer:
                                          (SEQ ID NO: 19)
5'-GGC CGT GCT GGC CCC GAC AGA TGG GGG TGT CGT TTT

GGC-3'.

Primer amplification of light-chain variable
region encoding sequence (396 bp):
Forward primer:
                                          (SEQ ID NO: 20)
5'-CCA TTG CAG TGG CAC TGG CTG GTT TCG CTA CCG TAG

CAC AGG CAG CCG AYA TTG TGM TSA CMC ARW CTM CA-3';

Reverse primer:
                                          (SEQ ID NO: 21)
5'-CCA CCG TAC TGG CGG ATA CAG TTG GTG CAG CAT C-3'
```

The recombinant expression plasmid pFabE-hMUC1-1H7 was identified by restriction analysis and DNA sequencing. The pFabE-hMUC1-1H7 was transformed into TG1 *E. coli* cells, the expression of the recombinant protein was optimized, and the pFabE-hMUC1-1H7 was identified by Western blotting using an anti-His antibody.

For the mass-production and purification of the recombinant Fab (pFabE-hMUC1-1H7), 500 ml of the hybridoma hMUC1-1H7 clone culture was treated with 0.5 mM IPTG and cultured at 18° C. for 16 hours. The culture solution was centrifuged, the culture supernatant was harvested, placed in a Ni-NTA affinity column (Clontech), and appropriately folded and assembled Fab proteins were separated using a His tag in the VH-CH fusion protein.

The recombinant Fab bound to the column was eluted with 10 mM imidazole (pH 8.0) and the protein solution was centrifuged (3,500×g) at 4° C., dialyzed using Centricon®, and concentrated.

Example 12: MTT Assay

The growth of cancer cells treated with the anti-hMUC1 monoclonal antibody (10 µg/ml) for 5 days was measured using a 3-(4,5-dimethylthiazol-2-yl)-2,5-diphenyltetrazolium bromide (MTT, Sigma-Aldrich) solution. At the indicated time, the MTT solution was added to each well and the plate was cultured at 37° C. for an additional 4 hours. After removal of the medium, formazan crystals were dissolved in DMSO. The color development was monitored using a 595 nm spectrophotometer with a reference wavelength of 650 nm.

Example 13: Biodistribution Imaging In Vivo $5\times10^6$ Capan-2 cells in 50% (w/v) Matrigel were subcutaneously inoculated into the dorsal right flank of 4-week-old male BALB/cAnCrj-nu/nu mice. For breast cancer cell line injection, 17 beta-estradiol pellets (USA, Fla., Sarasota, Innovative Research of America, pellet, 60-day release) was subcutaneously transplanted into mice. The following day, $5\times10^6$ cells (T47D, ZR75-1) in 50% (w/v) Matrigel were subcutaneously inoculated into the dorsal right flanks of the mice.

When the tumor volume reached an average of about 100 mm³, the mice were intravenously injected with normal mouse IgG-DyLight 755 (5 mg/kg) or anti-hMUC1 antibody-DyLight 755 (5 mg/kg). Then, antibody target images were monitored using an in-vivo imaging system (IVIS 200, Xenogen Corporation, MA) at 0, 24, 48 hours. In order to detect intracellular localization of anti-hMUC1 monoclonal antibody in vivo, DyLight 488-labeled anti-hMUC1 antibody (5 mg/kg) was intravenously injected. Two days later, tumor tissues were collected, and frozen sectioning was performed. Internalization of antibodies was detected in tumor sections with CLSM (LSM 710, Carl Zeiss).

Example 14: Production of Pancreatic Cancer Mouse Model

For xenograft analysis, $5\times10^6$ Capan-2 cells in 50% Matrigel were subcutaneously inoculated into the dorsal right flanks of 16 BALB/cAnCrj-nu/nu mice (n=8). When the tumor volume reached 75 mm³, the mice were randomly divided into two treatment groups (eight mice/group), that is, a PBS-treated group and an anti-hMUC1 monoclonal antibody-treated group. The antibody was administered intravenously twice a week in an amount of 10 mg/kg.

Tumor diameters were measured at 7-day intervals using a caliper, and the tumor volume was calculated using the following equation: (width$^2$×length)/2. After 11 weeks of treatment with the anti-hMUC1 monoclonal antibody, mice were sacrificed and the tumors were then weighed.

Example 15: Tissue Array and Immunohistochemistry

Paraffin-embedded human breast cancer tissue sections were purchased from ISU ABXIS (Seoul, Korea). The tissue sections were treated with xylene for 30 minutes to remove paraffin, rehydrated with ethanol, and incubated with 3% hydrogen peroxide solution for 10 minutes. Antigen retrieval was performed in a citric acid solution (pH 6.0). The sections were blocked with normal horse serum for 30 minutes and incubated with anti-hMUC1 antibody (1 µg/slide) at room temperature for 2 hours. The sections were washed and incubated with a biotinylated anti-mouse IgG antibody (Vector Laboratories, Burlingame, Calif.) for 1 hour. Then, the tissue sections were washed and incubated with HRP-streptavidin for 30 minutes. Immunoreactivity was detected using 3,3-diaminobenzidine (DAB, Thermo Fisher Scientific) and the tissue sections were counterstained with hematoxylin (Muto Pure Chemicals, Tokyo, Japan). All images were examined using a microscope (Eclipse E-200, Nikon, Tokyo, Japan).

Example 16: Characterization of Anti-hMUC1 Monoclonal Antibody

Mice were immunized with PBS (control) or rhMUC1-C and Lipoplex (O) complex (n=4) (see Example 5), the third immunization was conducted, the mouse serum was collected, and the total amount of rhMUC1-C-specific IgG was measured using ELISA (see Example 6) to identify the formation of antibodies against rhMUC1-C. The results are shown in FIG. 1a. In FIG. 1a, the control represents a PBS-inoculated group, and rhMUC1-C-1, -2, -3, and -4 represent individual mice. As can be seen from FIG. 1a, the rhMUC1-C-specific IgG was significantly induced.

Figure 1B:
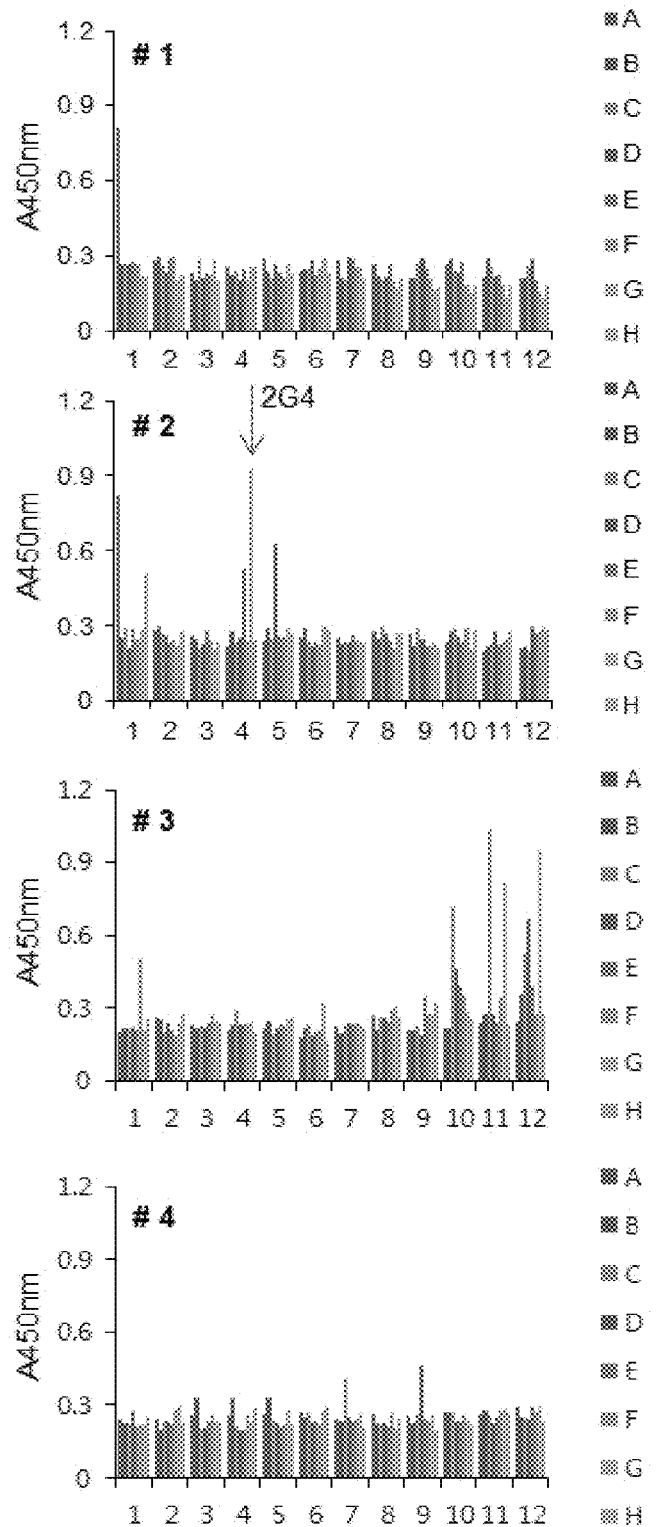
FIGS. 1b and 1c show the results of screening hybridoma cells isolated from immunized mice, more specifically.
Figure 1C:
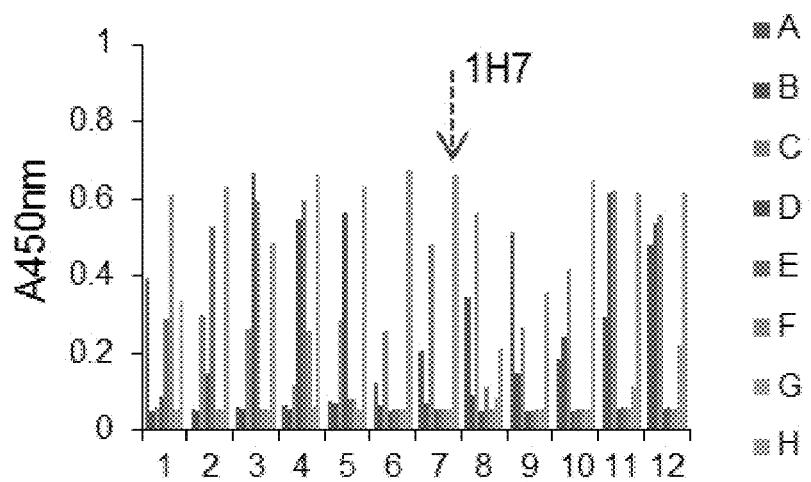
Figure 1C:
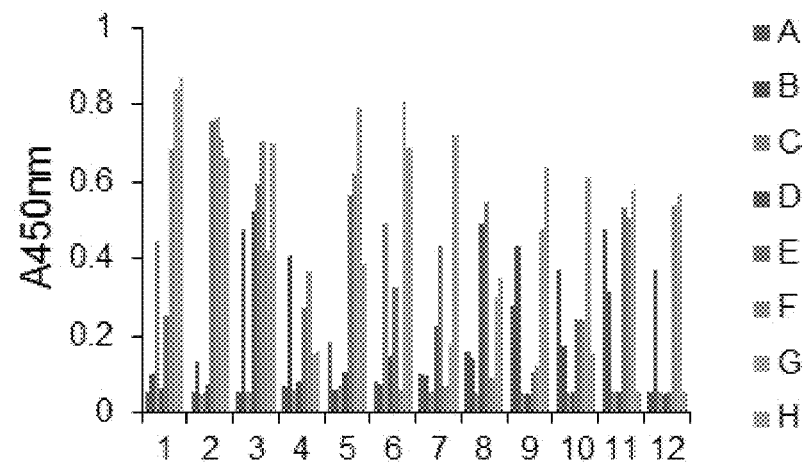

Next, hybridoma cells isolated from the immunized mice were screened according to Example 7, and the results are shown in FIGS. 1b and 1c. FIG. 1b shows the result of screening using HAT medium, and FIG. 1c shows the result of screening using HT medium. In FIGS. 1b and 1c, #represents the number of 96-well plates, and A-H represents the names of the horizontal sections of the plate. From the results of FIGS. 1b and 1c, hMUC1-1H7 clones were selected as hybridomas producing rhMUC1-C-specific monoclonal antibodies.

The selected hybridoma hMUC1-1H7 cells were deposited under the accession number KCLRF-BP-00395 with the Korean Cell Line Research Foundation (KCLRF) located in Yeongeon-dong, Jongno-gu, Seoul, Korea on Mar. 8, 2017.

Figure 2A:
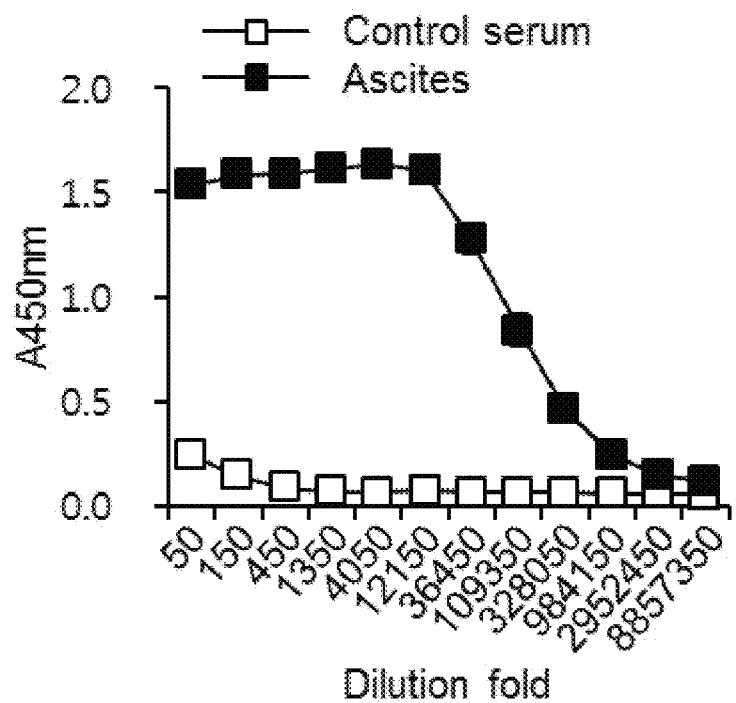
FIG. 2a is a graph showing the results of ELISA performed on a plurality of mice immunized with hybridoma cells (hMUC1-1H7 clones), which shows the presence of rhMUC1-C-specific antibody.
Figure 2B:
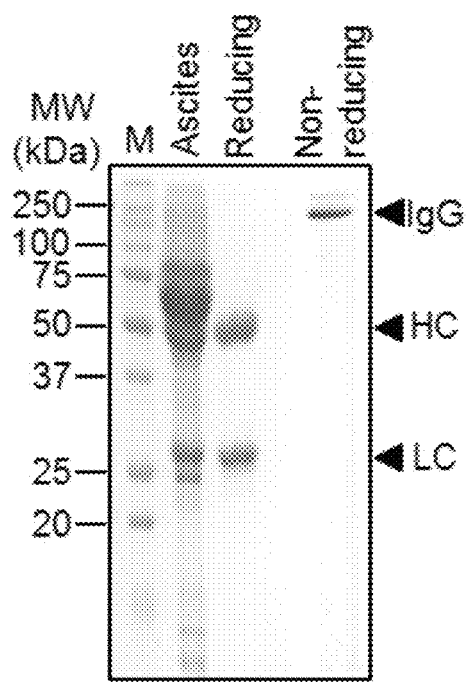
FIG. 2b shows the result of analysis of the purified anti-hMUC1 monoclonal antibody by SDS-PAGE and Coomassie staining.

Next, the anti-hMUC1 monoclonal antibody was purified from the separated hybridoma hMUC1-1H7 clone, and the purified antibody was analyzed using SDS-PAGE and Coomassie staining. FIG. 2A shows the results of ELISA analysis to determine the presence of rhMUC1-C-specific antibody in ascites collected after injecting the hybridoma hMUC1-1H7 clone into the peritoneal cavity of mice, wherein the control serum is the result of the PBS-inoculated group. The result showed that the rhMUC1-C-specific antibody was present in the ascites of mice injected with the hMUC1-1H7 clone, and the rhMUC1-C-specific antibody was separated and purified. The separated and purified anti-hMUC1 monoclonal antibody was analyzed by SDS-PAGE and Coomassie staining, and the results are shown in FIG. 2B. In FIG. 2B, HC represents a heavy chain and LC represents a light chain.

Figure 2C:
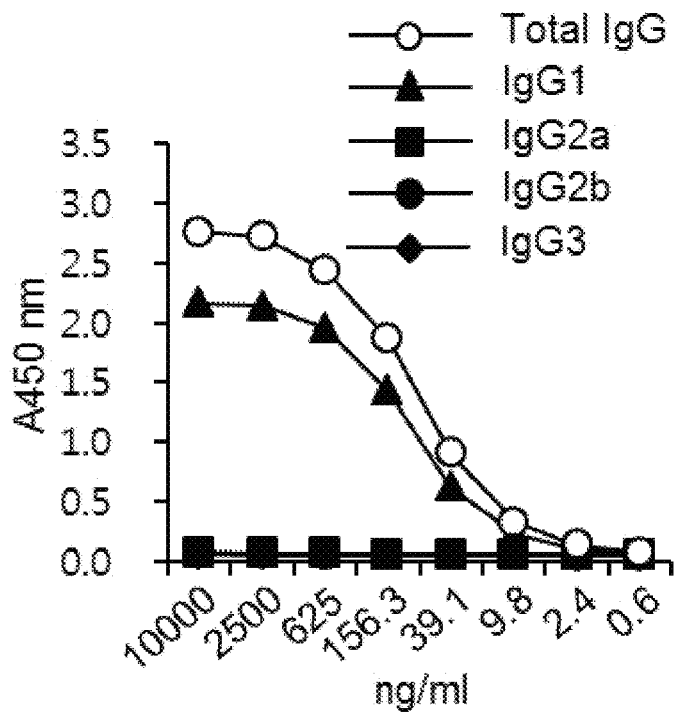
FIG. 2c is a graph showing the results of determination of the isotype of the anti-MUC1 antibody through ELISA.

ELISA was performed on several IgG isotypes to identify the isotype of the obtained anti-MUC1 antibody (see Example 8), and the result is shown in FIG. 2C. As can be seen in FIG. 2C, the purified anti-MUC1 antibody was an IgG1 type.

Figure 3A:
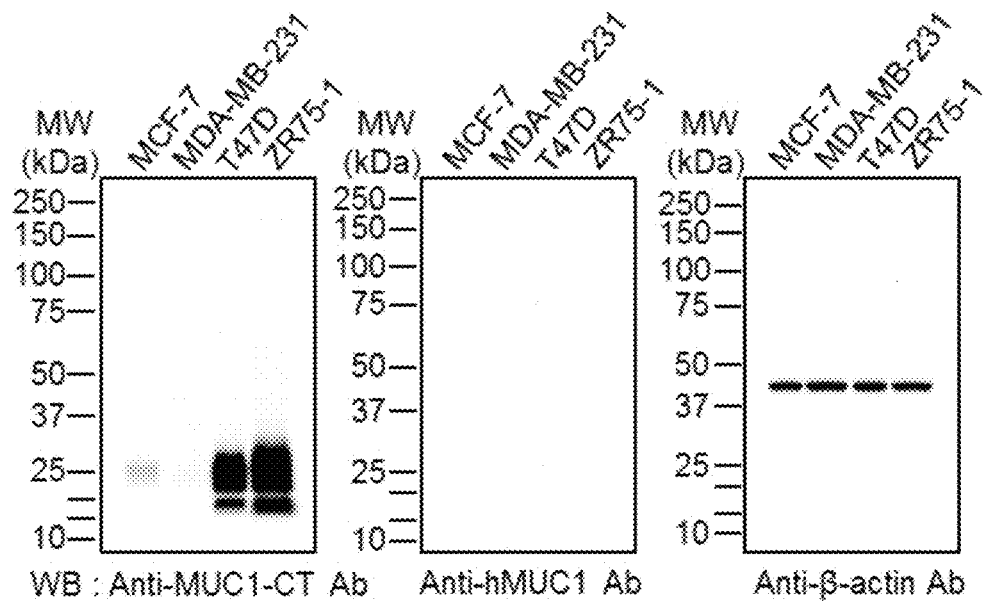
FIG. 3a shows the results of Western blotting using an anti-hMUC1 monoclonal antibody and an anti-MUC1-CT antibody purified from hMUC1-1H7 clones in a breast cancer cell lysate.

Example 17: Anti-MUC1 Antibody Specificity Test in Breast Cancer Cells and Pancreatic Cancer Cells In order to identify whether or not the obtained anti-hMUC1 monoclonal antibody recognizes MUC1 protein (in normal cells, MUC1 protein includes a dimer composed of a MUC1-N subunit domain and a MUC1-C subunit domain and is hyperglycosylated, but in cancer cell lines, the MUC1 protein is predominantly composed of a MUC1-C subunit domain and is hypoglycosylated), cell lysates of breast cancer cells (MCF-7, MDA-MB-231, T47D and ZR75-1) were separated through SDS-PAGE, and Western blotting was conducted using an anti-hMUC1 monoclonal antibody and an anti-MUC1-CT antibody (see Example 9.4). The obtained results are shown in FIG. 3A. The results showed that the anti-MUC1-CT antibody detected MUC1 protein in MCF-7, T47D and ZR75-1, but did not detect MDA-MB-231. On the other hand, the anti-hMUC1 monoclonal antibody did not recognize MUC1 protein in all cell samples. Since the MUC-1 protein was not detected in MDA-MB-231 cells, this cell line was used as a negative control group in all tests.

Figure 3B:
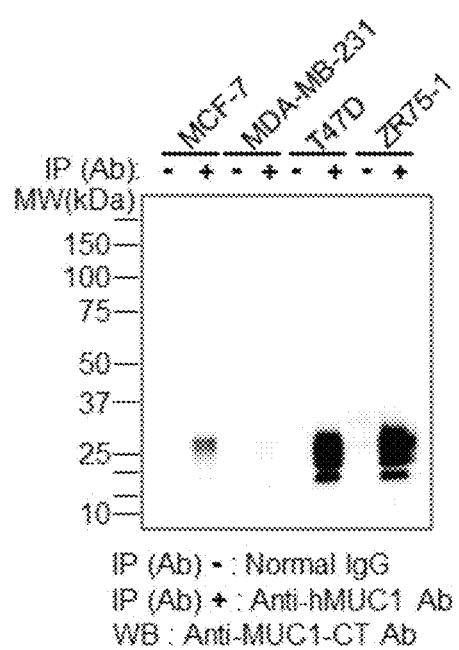
FIG. 3b shows the results of immunoblotting using an anti-MUC1-CT antibody after immunoprecipitation of cell lysates of MCF-7, MDA-MB-231, T47D and ZR75-1 cells with anti-hMUC1 monoclonal antibodies purified from normal mouse IgG or hMUC1-1H7 clones.

In order to determine whether or not the anti-hMUC1 monoclonal antibody can recognize the endogenous MUC1 protein in an intact (native) state, cell lysates of MCF-7, MDA-MB-231, T47D and ZR75-1 cells were immunoprecipitated with normal mouse IgG or anti-hMUC1 monoclonal antibody and immunoblotted using an anti-MUC1-CT antibody (see Example 9.5), and the results are shown in FIG. 3B. As can be seen from FIG. 3b, the anti-hMUC1 monoclonal antibody can efficiently immunoprecipitate MUC1 protein in an intact state in MCF-7, T47D and ZR75-1 cells.

The results of FIG. 3a show that the anti-hMUC1 monoclonal antibody does not recognize the denatured MUC1 protein used in Western blotting, whereas the result of FIG. 3b shows that the anti-hMUC1 monoclonal antibody recognizes intact MUC1 protein in cancer, which indicates that the anti-hMUC1 monoclonal antibody recognizes the intact (inherent) tertiary structure of the MUC1 protein.

Figure 3C:
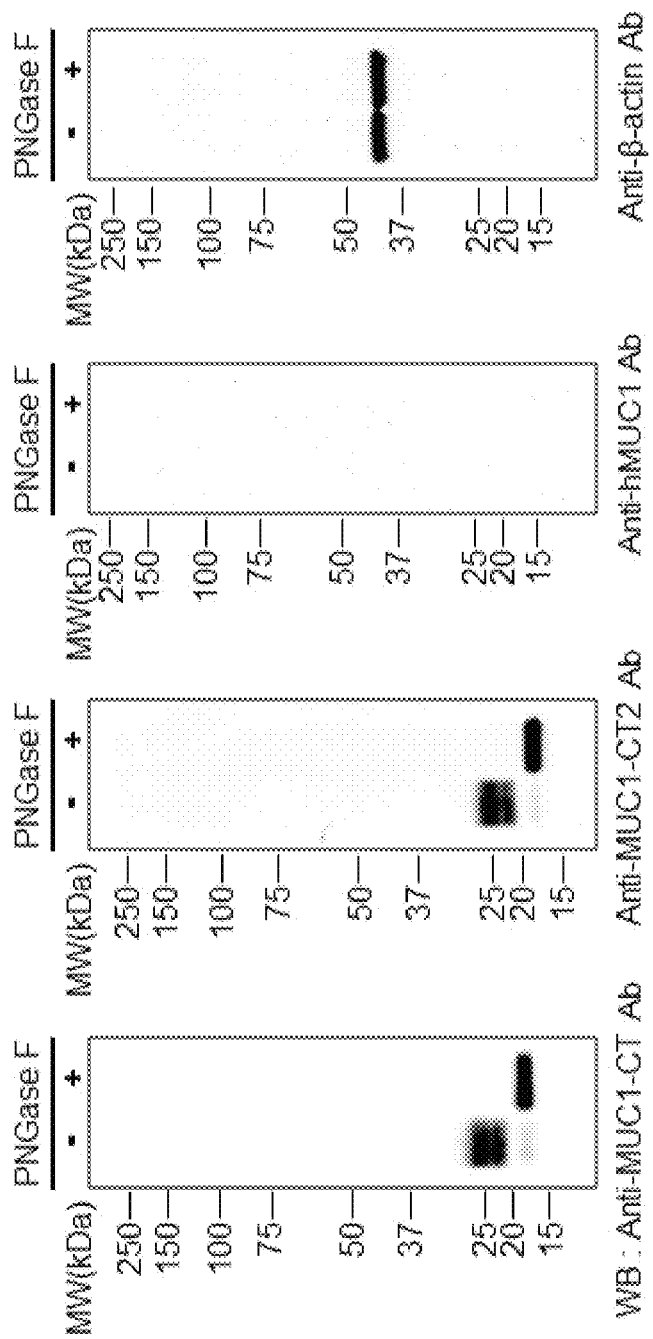
FIG. 3c shows the results of treating a T47D cell lysate with PNGase F and then Western blotting using an anti-hMUC1 monoclonal antibody purified from hMUC1-1H7 clones for comparison with the case of using other antibodies.
Figure 3D:
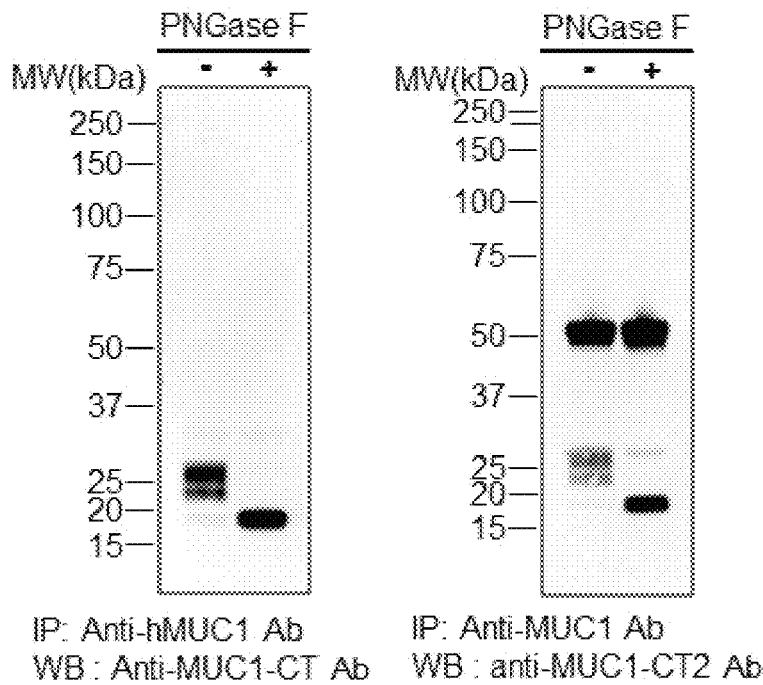
FIG. 3d shows the results of immunoprecipitation of T47D cell lysate treated with PNGase F using an anti-hMUC1 monoclonal antibody purified from an hMUC1-1H7 clone and then immunoblotting with an anti-MUC1-CT or anti-MUC1-CT2 antibody.

The extracellular domain of MUC1 is densely glycosylated to 200 to 500 nm from the cell surface. Thus, whether or not the anti-hMUC1 monoclonal antibody was able to recognize the deglycosylated protein core was determined (see Example 9.6). T47D cell lysates were treated with PNGase F and subjected to western blotting using an anti-MUC1-CT antibody, anti-MUC1-CT2 antibody, anti-hMUC1 monoclonal antibody (Example 7), or anti-beta-actin antibody. The results are shown in FIG. 3c. As can be seen from FIG. 3c, the anti-hMUC1 monoclonal antibody does not detect the MUC1 protein. Meanwhile, FIG. 3D shows the result of immunoprecipitation of a PNGase F-treated T47D cell lysate with an anti-hMUC1 monoclonal antibody and then immunoblotting thereof with an anti-MUC1-CT or anti-MUC1-CT2 antibody. As can be seen from FIG. 3d, the anti-hMUC1 monoclonal antibody is capable of immunoprecipitating the deglycosylated MUC1 protein in T47D cells. These results demonstrate that the anti-hMUC1 monoclonal antibody can successfully recognize the MUC1 protein in an intact (natural) state, regardless of the glycosylation status.

Figure 4A:
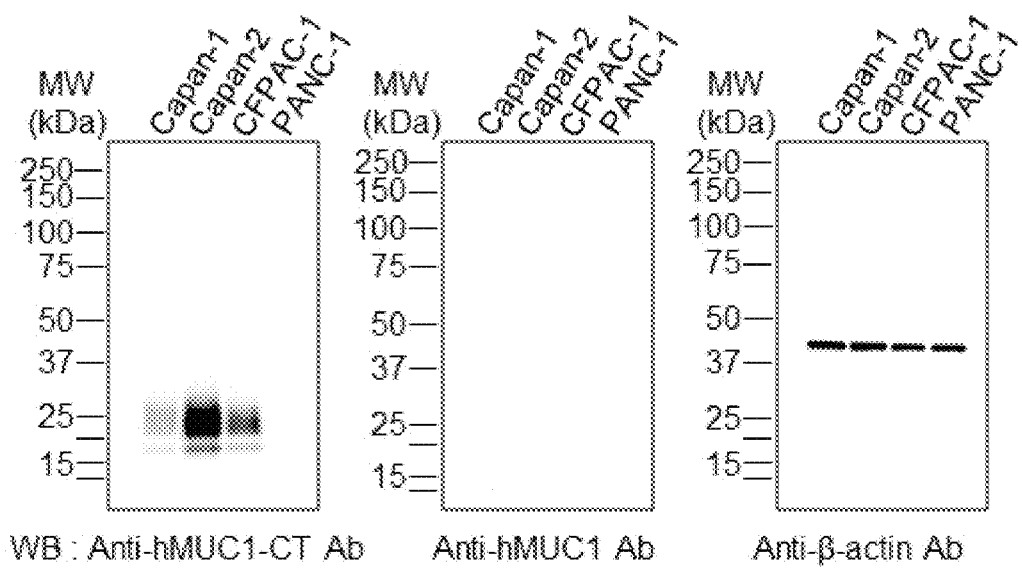
FIG. 4a shows the result of Western blotting of a pancreatic cancer cell lysate using an anti-MUC1-CT antibody, an anti-hMUC1 antibody purified from an hMUC1-1H7 clone, or an anti-beta-actin antibody.

In order to test whether or not the anti-hMUC1 monoclonal antibody can recognize the intact MUC1 protein in pancreatic cancer cells, cell lysates of pancreatic cancer cells (Capan-1, Capan-2, CFPAC-1, and PANC-1) were separated by SDS-PAGE, Western blotting was performed using anti-MUC1-CT antibody, anti-hMUC1 antibody, or anti-beta-actin antibody, and the results are shown in FIG. 4a. As can be seen in FIG. 4a, the anti-hMUC1 monoclonal antibody is incapable of recognizing MUC1 protein in all cell samples tested.

Figure 4B:
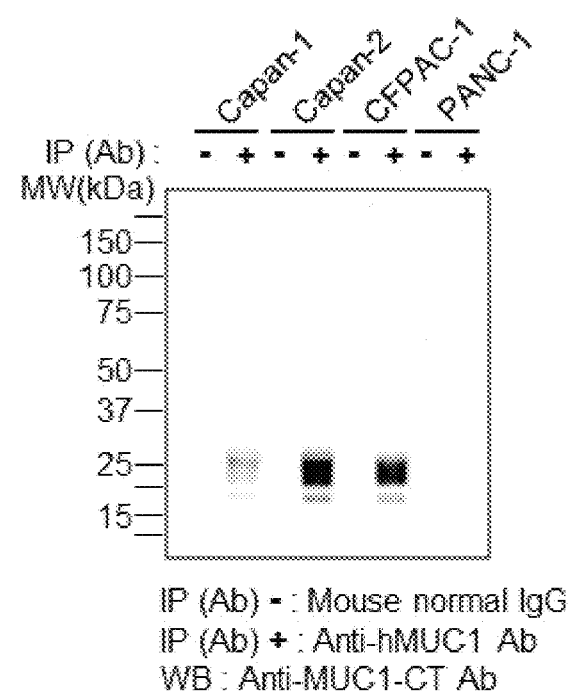
FIG. 4b shows the results of immunoprecipitation of a pancreatic cancer cell lysate with an anti-hMUC1 monoclonal antibody purified from normal mouse IgG or hMUC1-1H7 clone and then immunoblotting using an anti-MUC1-CT antibody and an anti-hMUC1 monoclonal antibody.

Meanwhile, in order to determine whether or not the anti-hMUC1 monoclonal antibody can recognize the intrinsic MUC1 protein as an intact state, cell lysates of various pancreatic cancer cells (Capan-1, Capan-2, CFPAC-1, and PANC-1) were immunoprecipitated and immunoblocked using an anti-MUC1-CT antibody and an anti-hMUC1 monoclonal antibody. The results obtained are shown in FIG. 4b. As can be seen from FIG. 4b, the anti-hMUC1 monoclonal antibody can efficiently immunoprecipitate the intact MUC1 protein in pancreatic cancer cells (Capan-2 and CFPAC-1).

Example 18 Identification of Recognition and Internalization of MUC1 Protein on Cell Surface and in Cell by Anti-hMUC1 Monoclonal Antibody In order to identify whether or not the anti-hMUC1 monoclonal antibody can recognize and bind to MUC1 protein in intact (uninjured) cells, breast cancer cells (MCF-7, MDA-MB-231, T47D and ZR75-1) and pancreatic cancer cells (Capan-1, Capan-2, CFPAC-1 and PANC-1) were immunofluorescently stained and the results were analyzed through confocal microscopy (see Example 9-7).

Figure 5A:
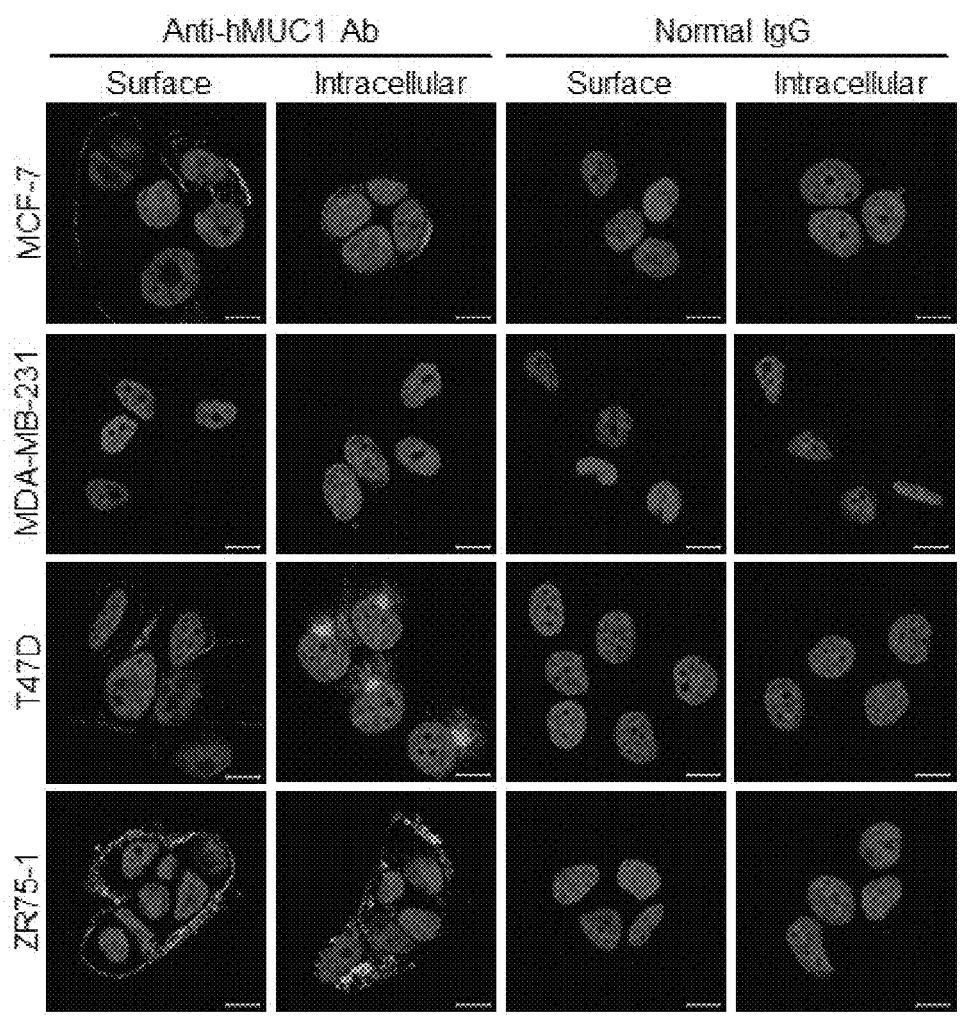
FIG. 5A is a fluorescence image obtained by treatment of breast cancer cells at 4° C. (surface) with an anti-hMUC1 antibody purified from a hMUC1-1H7 clone, or by lysis of cells with 0.1% Triton X-100 and then treatment with the antibody (intracellular).
Figure 5B:
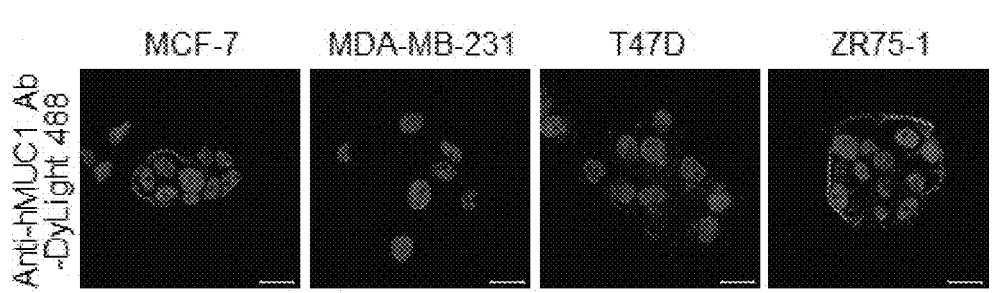
FIG. 5B shows a fluorescence image obtained by treating breast cancer cells with an anti-hMUC1 antibody purified from a fluorescence-probed hMUC1-1H7 clone and then culturing the same at 37° C. for 6 hours.

More specifically, the MCF-7, MDA-MB-231, T47D and ZR75-1 cells were incubated with anti-hMUC1 monoclonal antibody or normal mouse IgG at 4° C. (for cell-surface MUC1 protein) or at room temperature (for intracellular MUC1 protein) and then incubated with Alexa 488 (green)-conjugated secondary antibody for 1 hour, and cell nuclei were stained with Hoechst 33258 (blue). The fluorescence images obtained were observed with a confocal microscope (CLSM, LSM 710, Carl Zeiss, Jena, Germany), and are shown in FIG. 5A (scale bar: 10 μm). In addition, in order to identify the internalization of the anti-hMUC1 monoclonal antibody, MCF-7, MDA-MB-231, T47D, and ZR75-1 cells were also stained with DyLight 488 (green)-labeled anti-hMUC1 monoclonal antibody and cultured at 37° C. for 6 hours. The nuclei were stained with Hoechst 33258, and the obtained fluorescence images were observed with a confocal microscope (CLSM, LSM 710, Carl Zeiss, Jena, Germany) and are shown in FIG. 5B (Scale bar: 10 μm).

In addition, the binding of the anti-hMUC1 monoclonal antibody to the MUC1 proteins located on the cell surface and in the intracellular region of pancreatic cancer cells was tested. Pancreatic cancer cell lines, Capan-1, Capan-2, CFPAC-1 and PANC-1 cells, were cultured with anti-hMUC1 monoclonal antibody or normal mouse IgG at 4° C. (on cell surface) or room temperature (in cells) and cultured with conjugated secondary antibody for 1 hour, and the nuclei were stained with Hoechst 33258. The obtained fluorescence image was observed with a confocal microscope (CLSM, LSM 710, Carl Zeiss, Jena, Germany) and is shown in FIG. 6 (scale bar: 10 μm).

Figure 6:
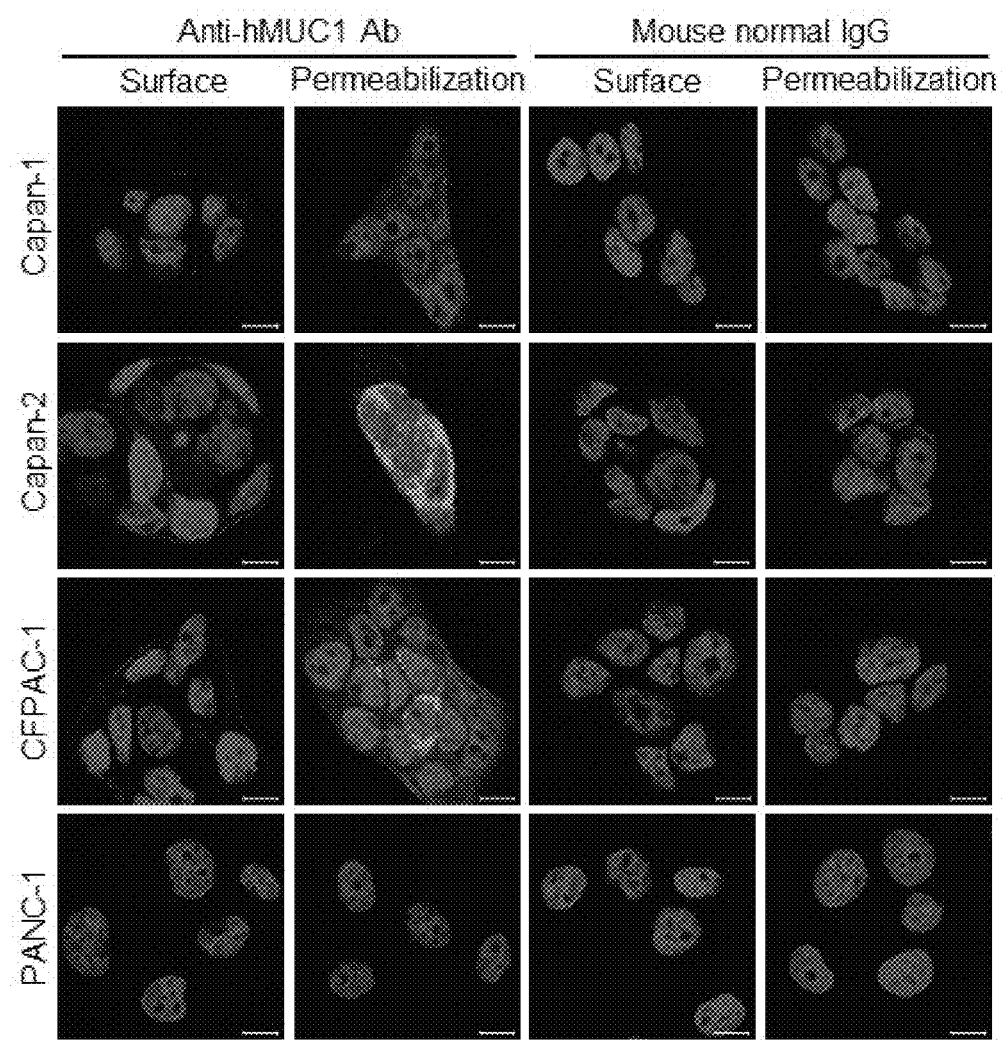
FIG. 6 is a fluorescence image obtained by treatment of pancreatic cancer cells with anti-hMUC1 antibodies purified from hMUC1-1H7 clone at 4° C. (surface), or by lysis of cells with 0.1% Triton X-100 and then treatment with the antibody (intracellular).

As can be seen from the results shown in FIGS. 5 and 6, the anti-hMUC1 antibody markedly stained MUC1 in breast cancer cells (MCF-7, T47D and ZR75-1) and pancreatic cancer cells (Capan-2 and CFPAC-1) and the MUC1 is located on the cell surface and within the cells.

Figure 7:
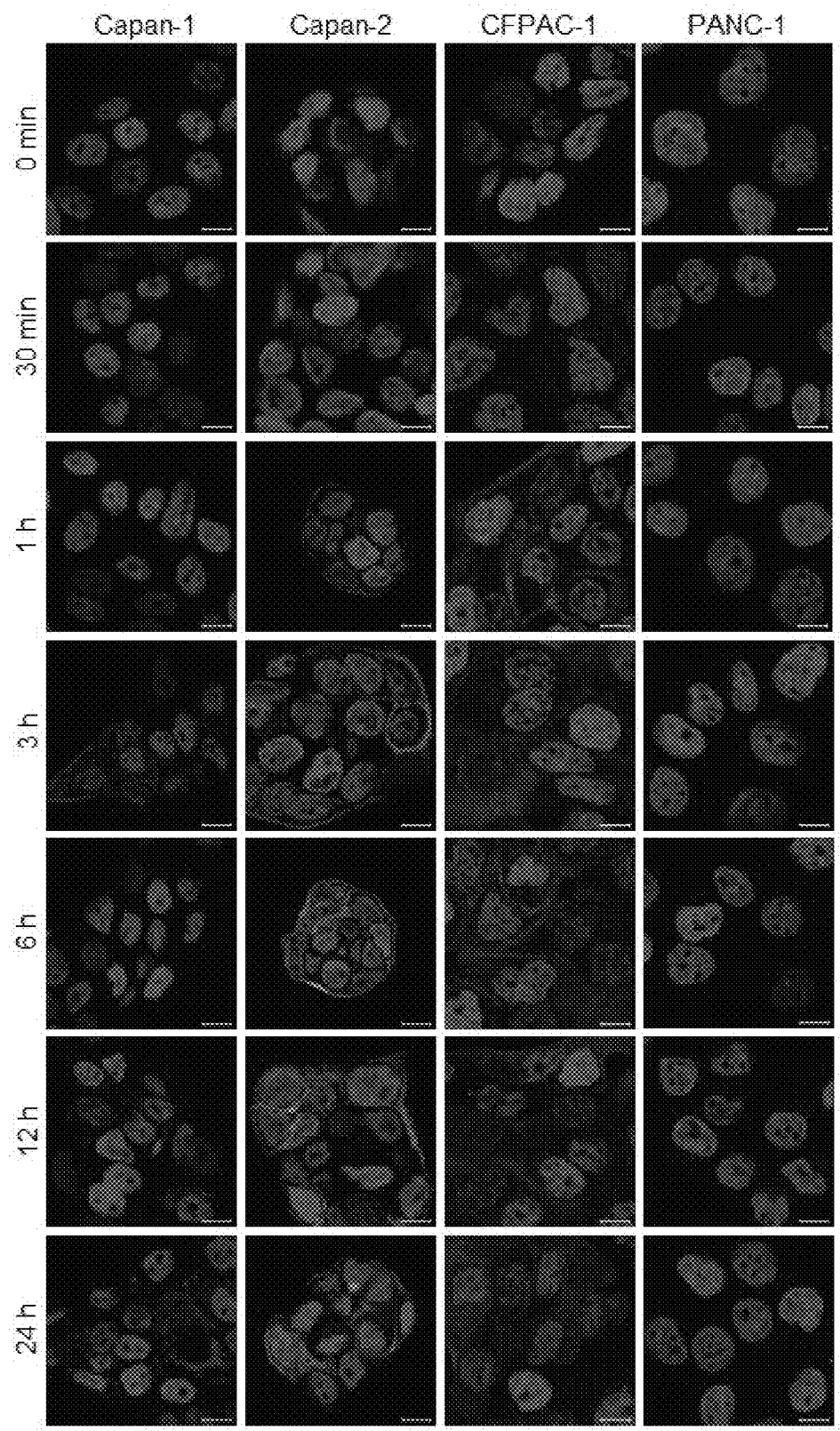
FIG. 7 is a fluorescence image obtained by treatment of pancreatic cancer cells with an anti-hMUC1 antibody purified from hMUC1-1H7 clone probed with fluorescence and then culture at 37° C. for 24 hours.

These results suggest that the antibody recognizes the extracellular region of the MUC1 C-terminal subunit. The efficacy of the antibody as a therapeutic agent can be considered to be more dependent upon cell internalization. Therefore, the anti-hMUC1 antibody was bound to DyLight 488 and breast cancer cells and pancreatic cancer cells were treated with the antibody for 6 hours, and the cell internalization of the antibody was identified by fluorescence imaging. The pancreatic cancer cells (Capan-1, Capan-2, CFPAC-1 and PANC-1) were treated with DyLight 488-labeled anti-hMUC1 monoclonal antibody and cultured at 37° C. for 0, 30 minutes, 1 hour, 3 hours, 6 hours, 12 hours and 24 hours. The nuclei were stained with Hoechst 33258. The obtained fluorescence image was observed with a confocal microscope (CLSM, LSM 710, Carl Zeiss, Jena, Germany) and is shown in FIG. 7 (scale bar: 10 μm). The cell internalization in breast cancer can be seen from FIG. 5B.

That is, the results showed that the anti-hMUC1 monoclonal antibody can target and internalize MUC1 protein in living cells.

Example 19: Results of Cloning of Variable Regions of Anti-hMUC1 Monoclonal Antibody The variable regions of the heavy and light chains of the anti-hMUC1 monoclonal antibody were cloned from the hybridoma cells (hMUC1-1H7) producing the anti-hMUC1 monoclonal antibody and DNA sequencing was performed (Example 10). The sequences identified by DNA sequencing were analyzed using the BLAST program (www.ncbi.nlm.nih.gov) to determine homology with known sequences. The cDNA (heavy-chain variable region coding cDNA: 393 bp; light-chain variable region coding cDNA: 396 bp) encoding the variable region of the heavy chain and the light chain of the hMUC1-1H7 antibody had sequence homology of 80 to 95% and 93 to 98% with the encoding sequence of the variable regions of the heavy chain and the light chain, respectively, of known mouse immunoglobulin (IgG1).

Based on the obtained DNA sequences, the CDRs of the heavy and light chains were identified by a known method (Kabat CDR definition) (Table 2). The variable region sequences of the heavy chain and the light chain are shown in Table 3 below.

TABLE 2

| Heavy-chain variable regino CDR | | SEQ ID NO | Light-chain variable region CDR | | SEQ ID NO |
| --- | --- | --- | --- | --- | --- |
| CDR1 | GYTFTSYWMH | 1 | CDR1 | KASQDIKSYLS | 4 |
| CDR2 | YINPGTGYIEYNQKFKD | 2 | CDR2 | YATRLAD | 5 |
| CDR3 | STAPFDY | 3 | CDR3 | LQYDESPYT | 6 |

TABLE 3

| | Amino acid sequence | SEQ ID NO |
|---|---|---|
| Heavy-chain hMUC1-1H7 variable region | EVQLQQSGAELAKPGASVKMSCKVSGYTFTSYWMH WVKQRPGQGLEWIGYINPGTGYIEYNQKFKDKATL TADKSSSTAYMQLSSLTSEDSAVYYCASSTAPFDY WGQGTTLTVSS | 22 |
| Light-chain hMUC1-1H7 variable region | DIVITQSPSSMYASLGERVTITCKASQDIKSYLSW YQQKPWKSPKTLIYYATRLADGVPSRFSGSGSGQD YSLTISSLESDDTATYYCLQYDESPYTFGGGTKLE IKR | 23 |

Example 20: Testing on Identification of Expression of Recombinant Fab Fragment Derived from Anti-hMUC1 Monoclonal Antibody and Recognition of MUC1 Protein of Cancer Cells by Recombinant Fab Fragment Recombinant Fab was expressed in *E. coli* using the expression vector pFabE (Example 11).

Figure 8B:
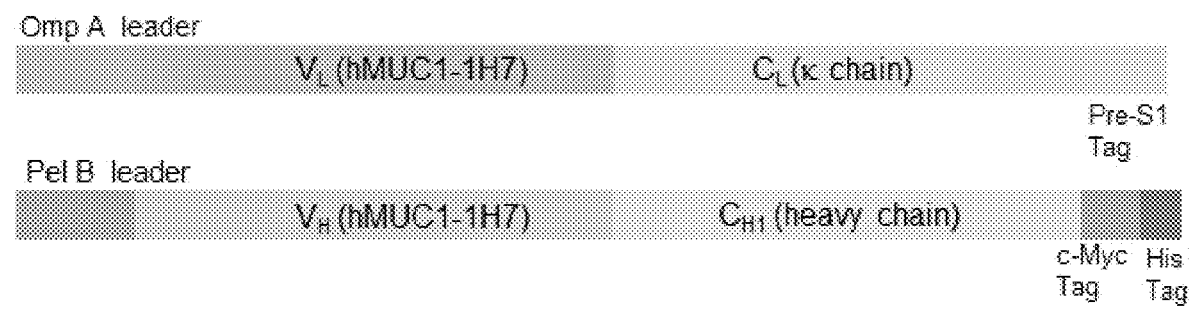
FIG. 8b schematically shows recombinant proteins expressed by the recombinant expression plasmid pFabE-hMUC1-1H7.

The vector pFabE includes two cloning sites, BstX I and Sfi I, into which a light-chain constant region (CL), a heavy-chain constant region (C$_{H1}$), a light-chain variable region (V$_L$) and a heavy-chain variable region (V$_H$) are inserted. The recombinant expression plasmid pFabE-hMUC1-1H7 was constructed by sequentially subcloning the V$_L$ and V$_H$ sequences of hMUC1-1H7 (FIG. 8a). The recombinant plasmid induces bicistronic expression of a VL-CL fusion protein and a VH-CH1 fusion protein under the control of the LacZ promoter in *E. coli*. The VL-CL fusion protein includes an N-terminal OmpA tag and a C-terminal Pre-S1 tag, while the VH-CH1 fusion protein includes an N-terminal pelB tag and a C-terminal His tag (FIG. 8b). Since the recombinant VH-CH1 fusion protein includes His tag, the mass-culture of *E. coli* and the purification of recombinant Fab of hMUC1-1H7 from the culture supernatant were performed using Ni-NTA affinity column chromatography.

In order to determine whether or not the purified recombinant Fab (hereinafter referred to as "recombinant Fab-hMUC1-1H7") can recognize MUC1 of cancer cells, breast cancer cells (MCF-7, MDA-MB-231, T47D and ZR75-7) were subjected to immunofluorescence staining. The breast cancer cells MCF-7, MDA-MB-231, T47D and ZR75-1 were each cultured together with the recombinant Fab-hMUC1-1H7 and were then cultured with the Alexa 488-conjugated secondary antibody, and the nuclei were stained with Hoechst 33258. The obtained fluorescence image was observed with a confocal microscope (CLSM, LSM 710, Carl Zeiss, Jena, Germany) and is shown in FIG. 8c (scale bar: 10 µm).

Figure 8C:
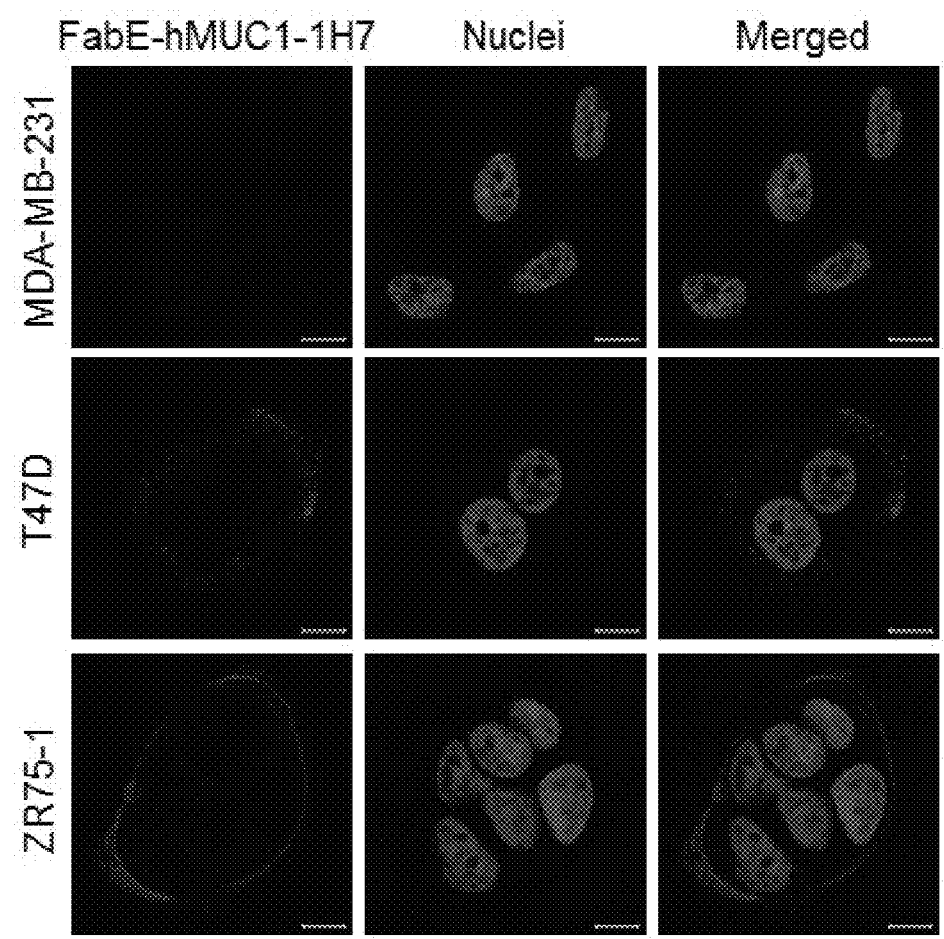
FIG. 8c is a fluorescence image obtained by treating MCF-7, MDA-MB-231, T47D and ZR75-1 cells with a Fab fragment of an anti-hMUC1 antibody derived from a hMUC1-1H7 clone.

As can be seen from the confocal image of FIG. 8c, the recombinant Fab-hMUC1-1H7 clearly stained MUC1 in the breast cancer cells (MCF-7, T47D and ZR75-1), indicating that the recombinant Fab-hMUC1-1H7 recognizes MUC1 of breast cancer cells.

Example 21: Inhibitory Effect of Anti-hMUC1 Monoclonal Antibody on Proliferation of Breast Cancer Cells MUC1 is overexpressed in various types of cancer tissues to promote the proliferation of cells. In order to determine the effectiveness of the anti-hMUC1 monoclonal antibody as a cancer therapeutic agent, the effect of the anti-hMUC1 monoclonal antibody on the proliferation of breast cancer cells was examined.

MDA-MB-231, T47D and ZR75-1 cells were treated with the anti-hMUC1 antibody (10 µg/ml; Example 7) or normal mouse IgG1 (10 µg/ml) and the effect of the antibody on cell proliferation was examined by MTT assay (Example 12).

Figure 9:
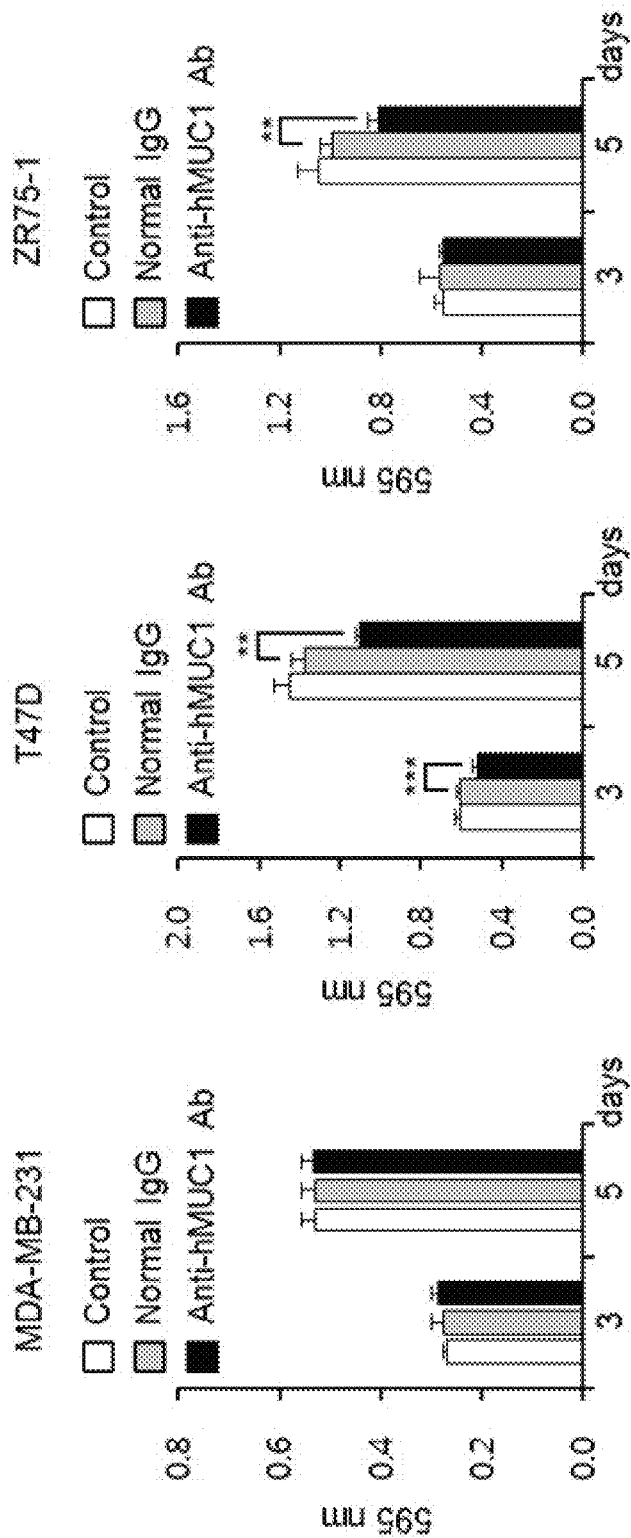
FIG. 9 is a graph showing cell proliferation changes when MDA-MB-231, T47D and ZR75-1 cells are treated with an anti-hMUC1 antibody derived from a hMUC1-1H7 clone.

The results obtained are shown in FIG. 9. In FIG. 9, the control is the group not treated with an antibody. As shown in FIG. 9, the treatment of anti-hMUC1 antibody was found to result in significant delay of the proliferation of T47D and ZR75-1cells compared to the control group treated with IgG. On the other hand, the anti-hMUC1 antibody did not change the proliferation of MDA-MB-231 cells. These results demonstrate that the anti-hMUC1 monoclonal antibody has a selective anticancer effect against cancer cells expressing MUC1.

Example 22: Identification of In-Vivo Localization of Anti-hMUC1 Monoclonal Antibody Injected into Breast and Pancreatic Cancer In order to demonstrate the in vivo efficacy of the anti-hMUC1 monoclonal antibody, DyLight 755-labeled normal IgG (5 mg/kg) or DyLight 755-labeled anti-hMUC1 monoclonal antibody (5 mg/kg) was intravenously administered to BALB/C nu/nu mice having T47D, ZR75-1 or Capan-2 tumors, and systemic fluorescence imaging was performed (Example 13). The distribution of the labeled antibody was quantified by measuring the total flux (photon/sec) of fluorescence at 0, 24 and 48 hours.

Figure 10A:
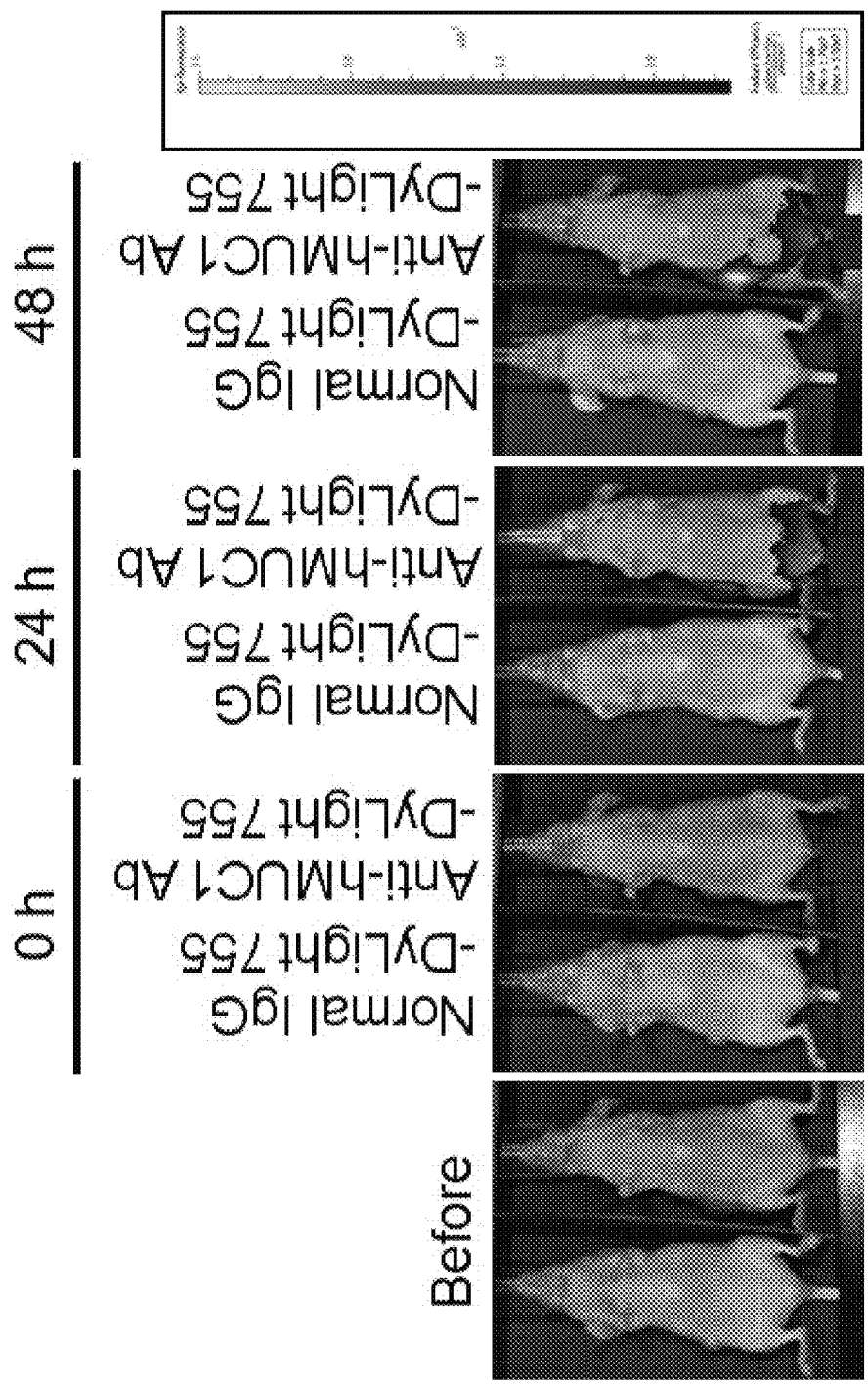
FIGS. 10a to 10h are fluorescence images obtained by intravenously administering an anti-hMUC1 monoclonal antibody derived from a fluorescence-labeled hMUC1-1H7 clone to a mouse having breast cancer.
Figure 10B:
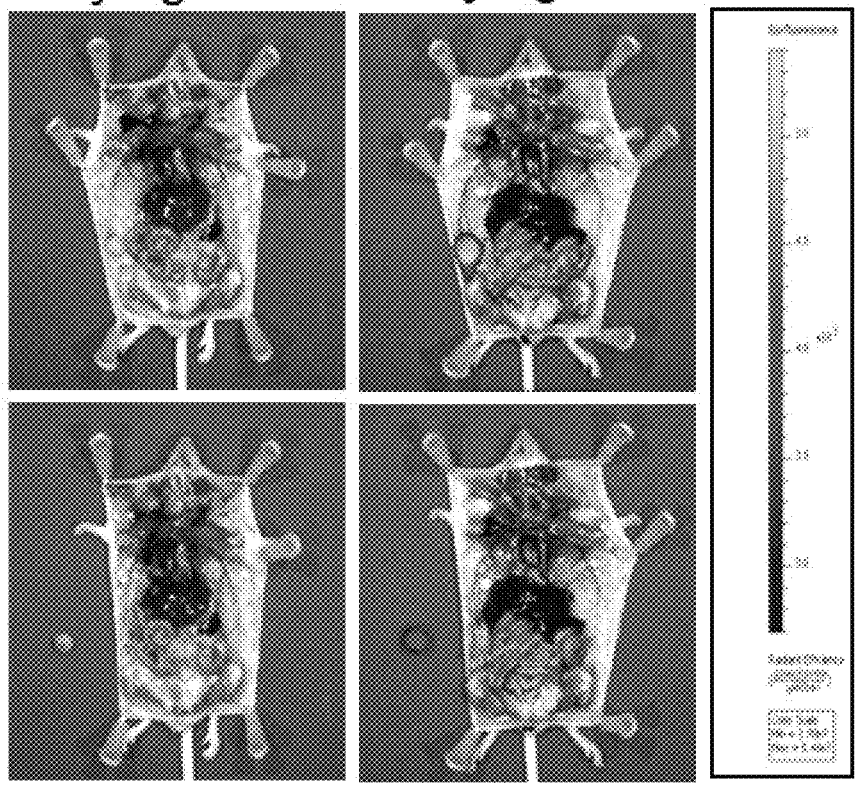
Figure 10C:
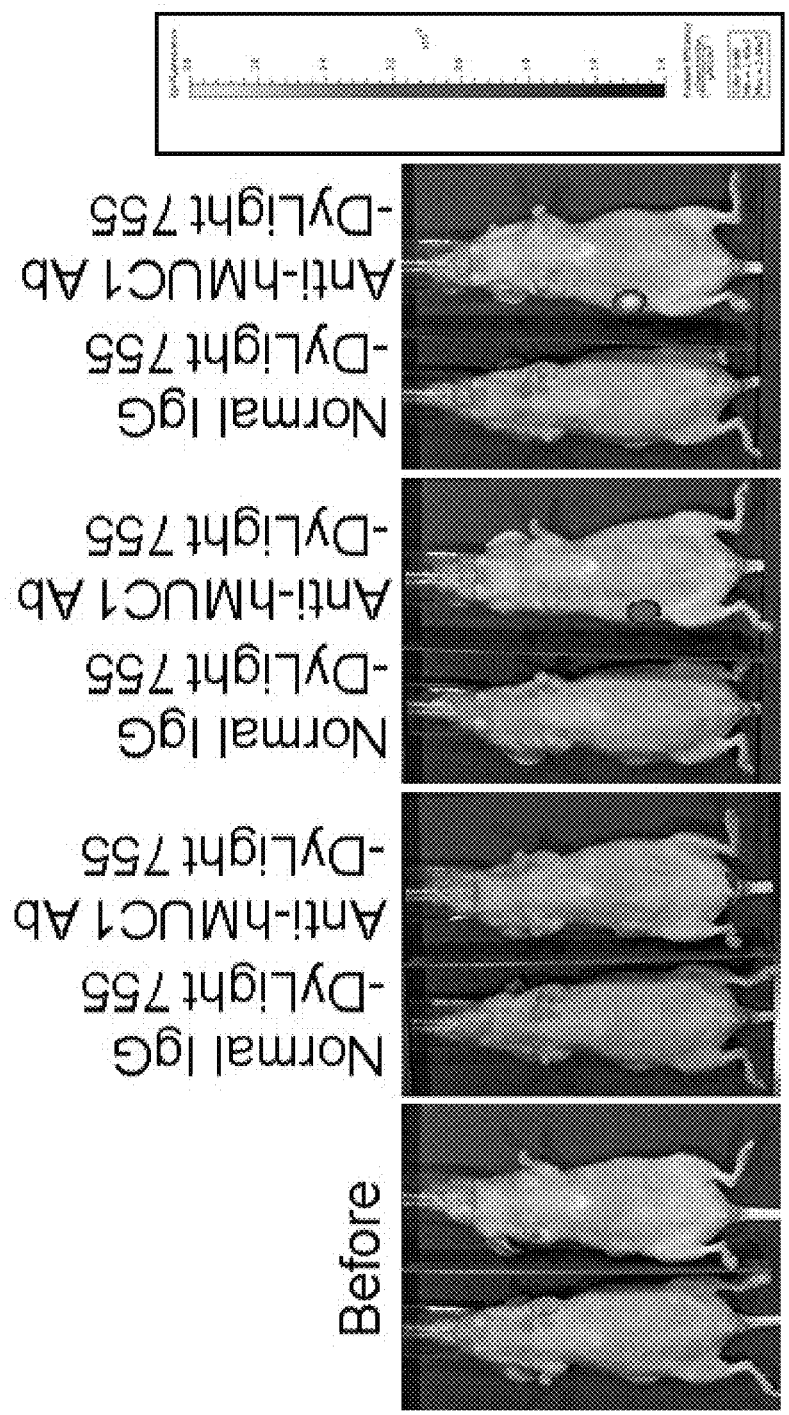
Figure 10D:
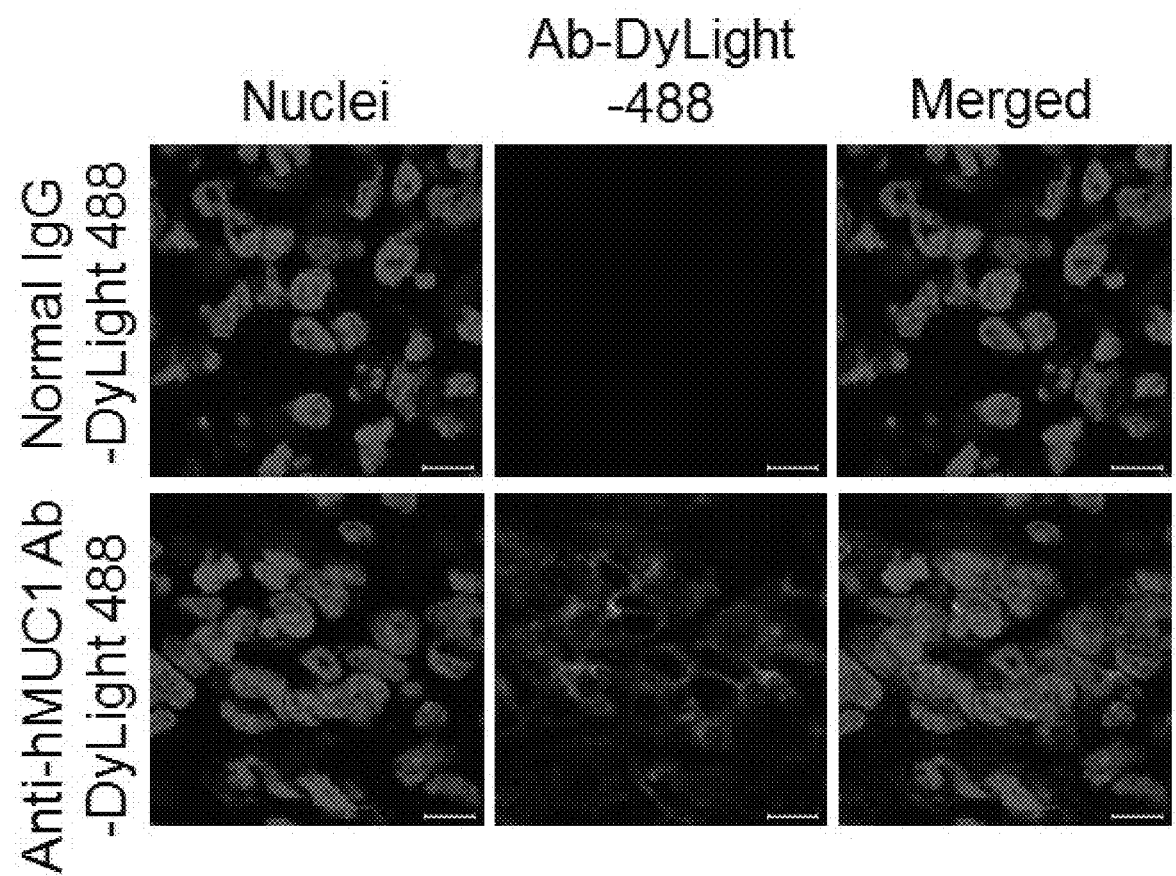
Figure 10E:
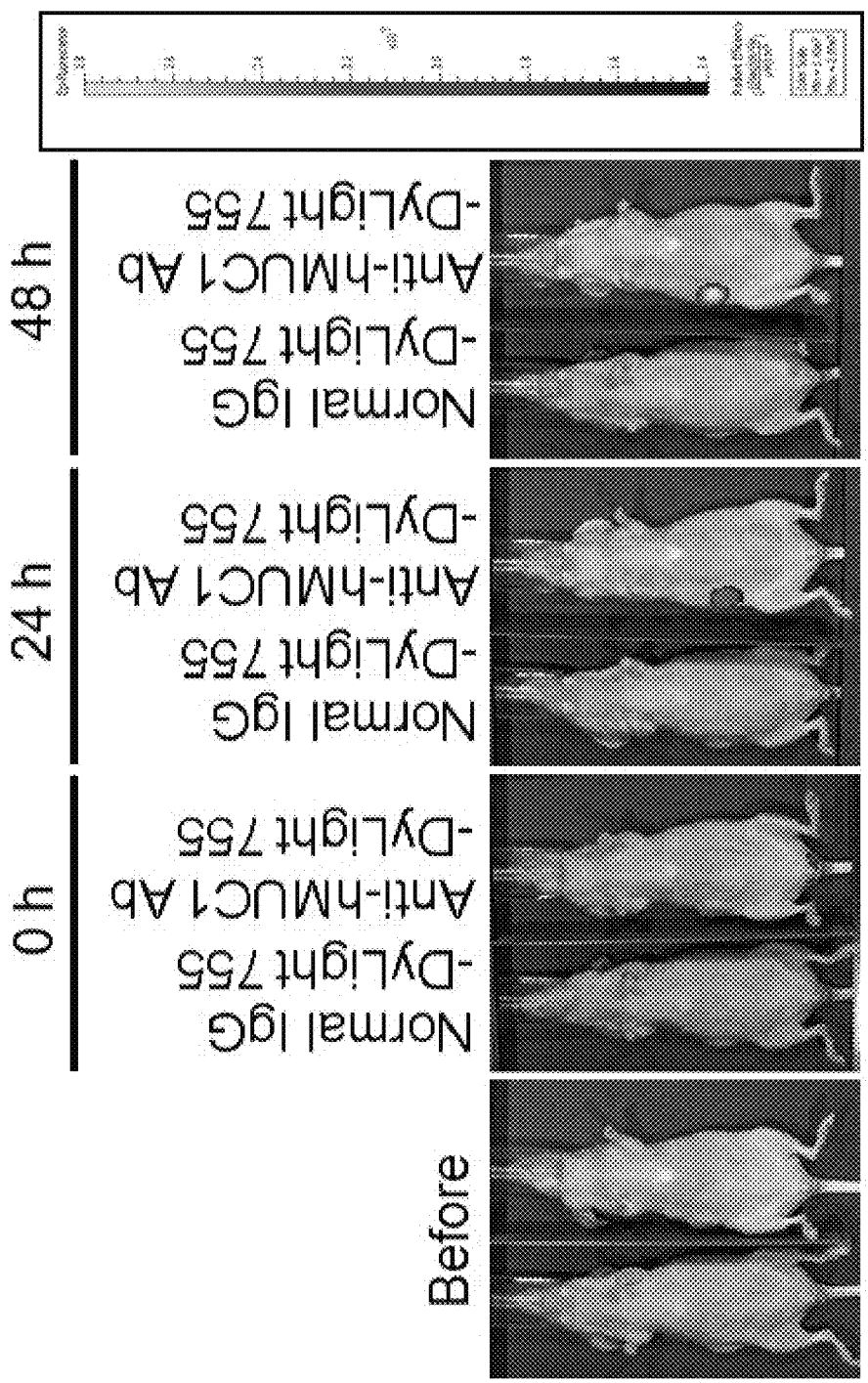
Figure 10F:
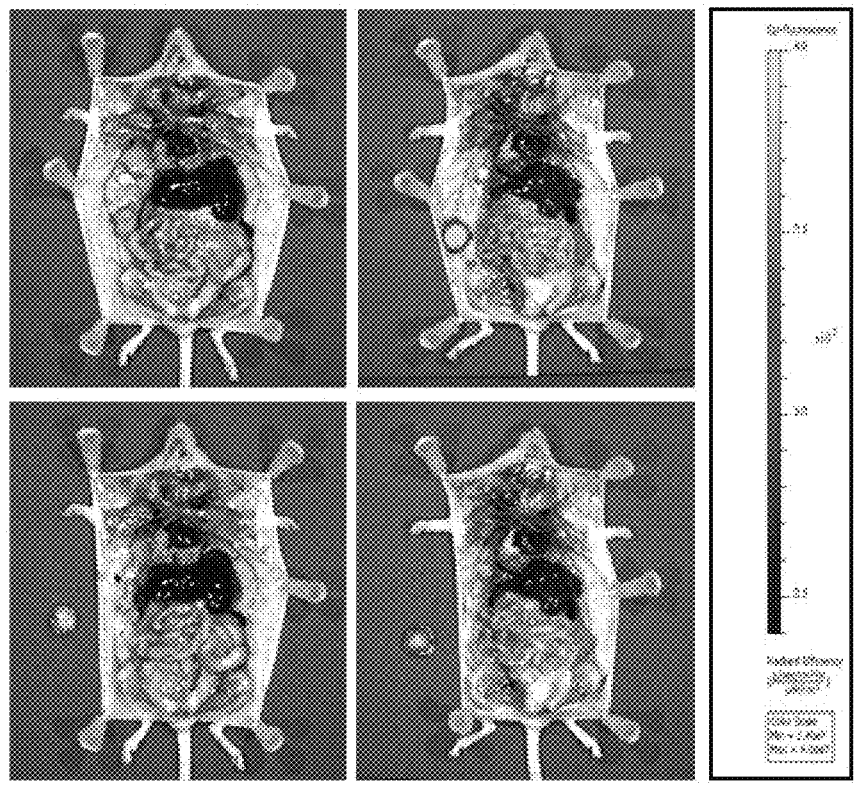
Figure 10G:
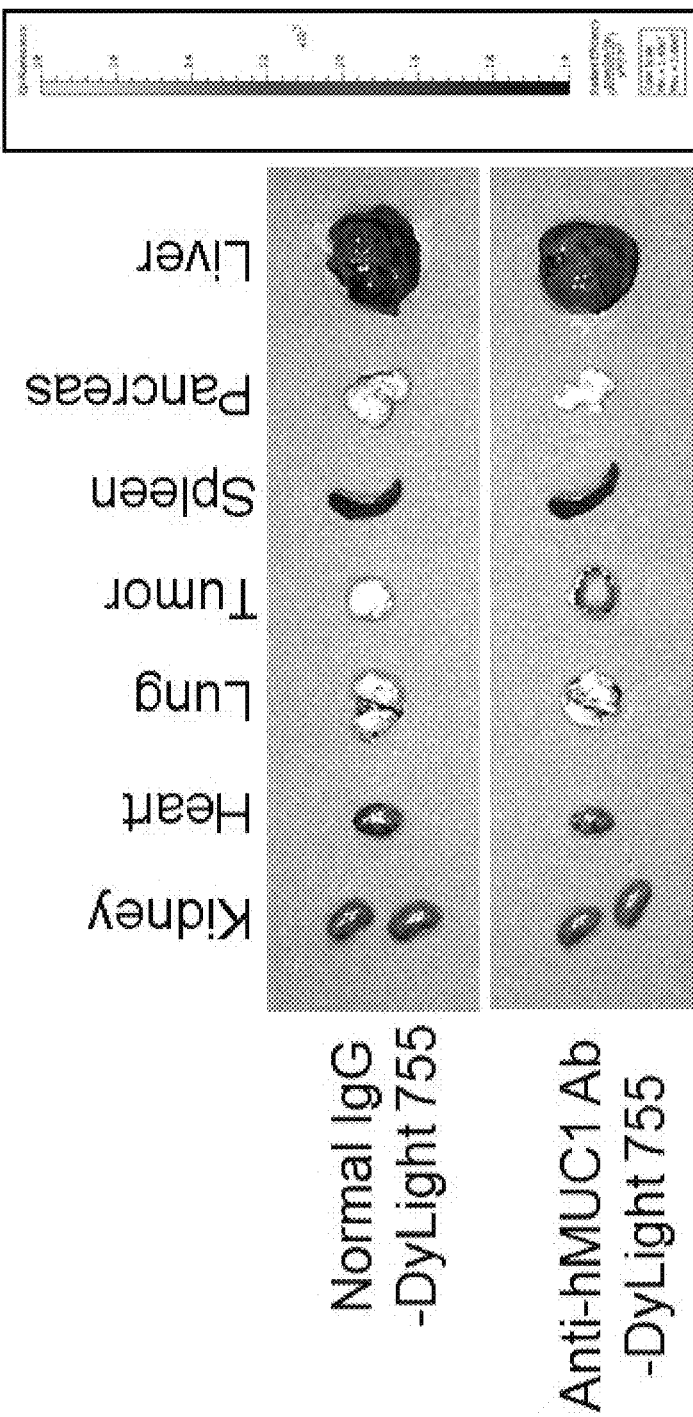
Figure 10H:
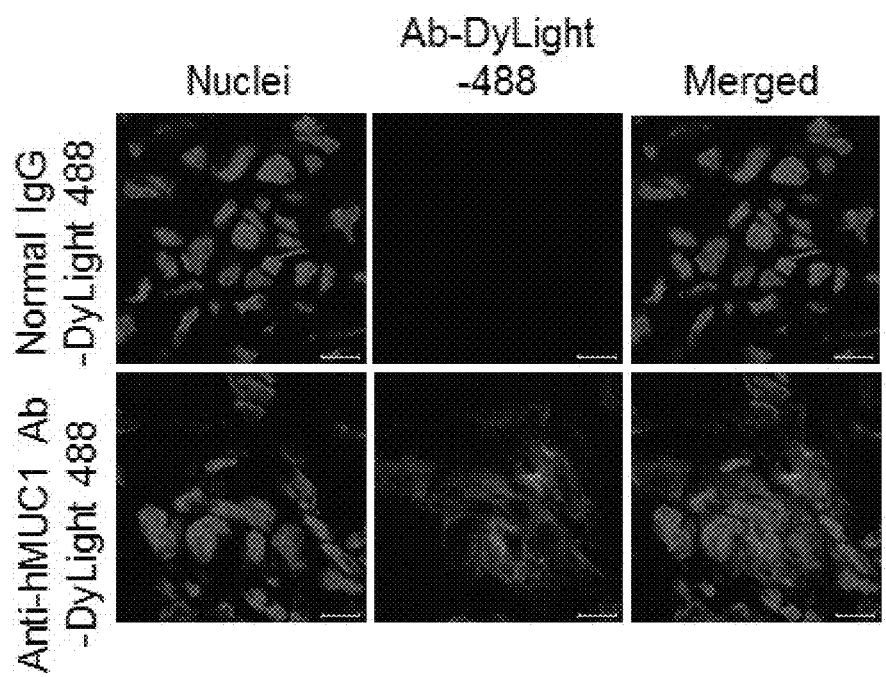
Figure 11A:
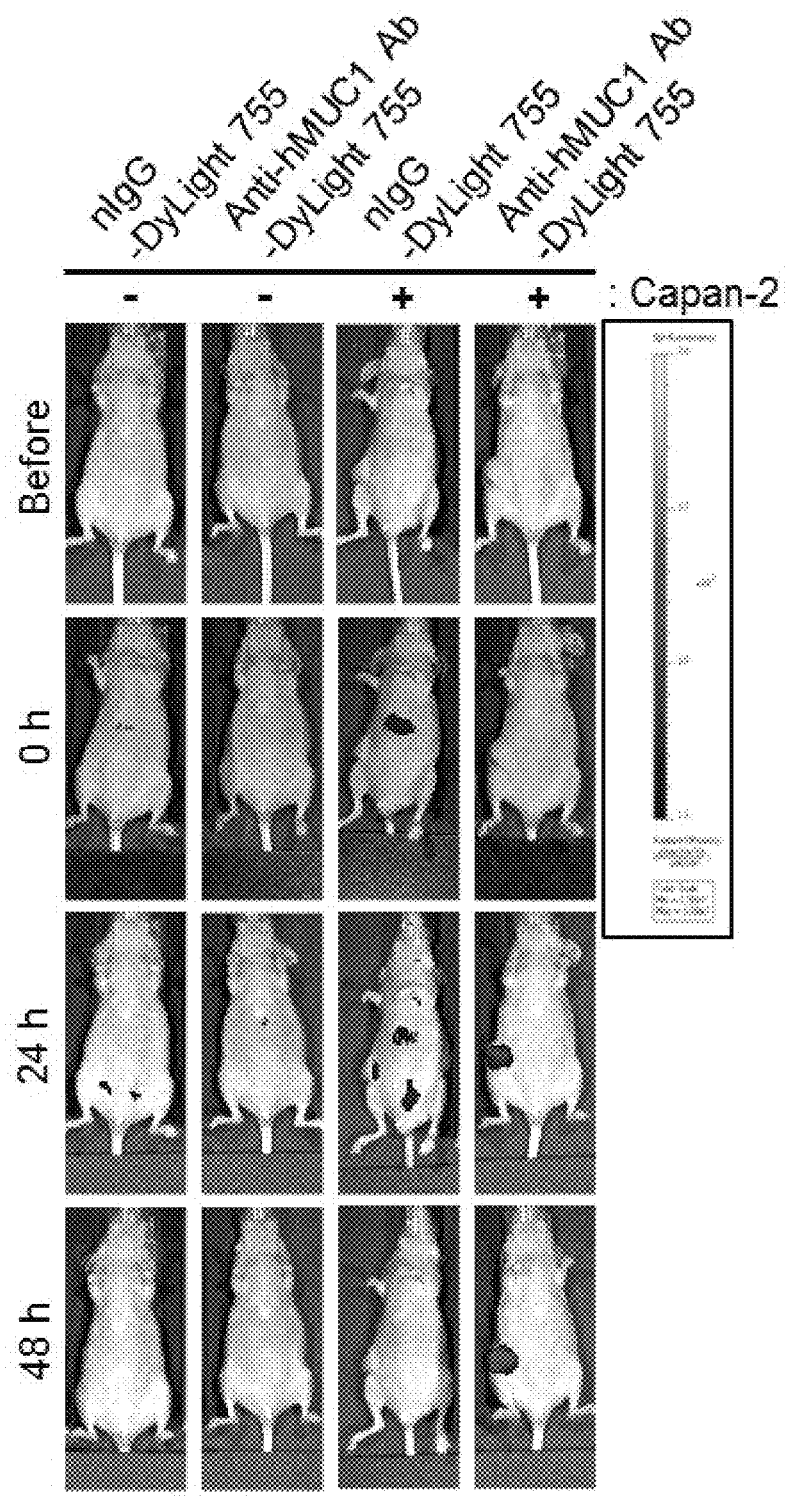
FIGS. 11a to 11c are fluorescence images obtained by intravenously administering an anti-hMUC1 monoclonal antibody derived from a fluorescence-labeled hMUC1-1H7 clone to a mouse having pancreatic cancer.
Figure 11B:
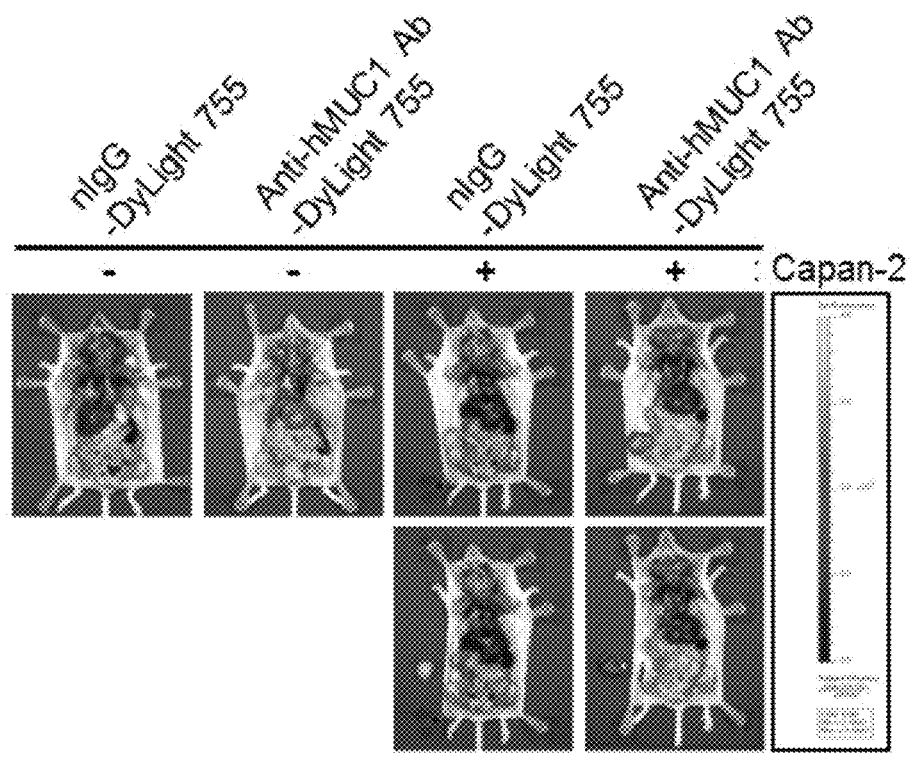
Figure 11C:
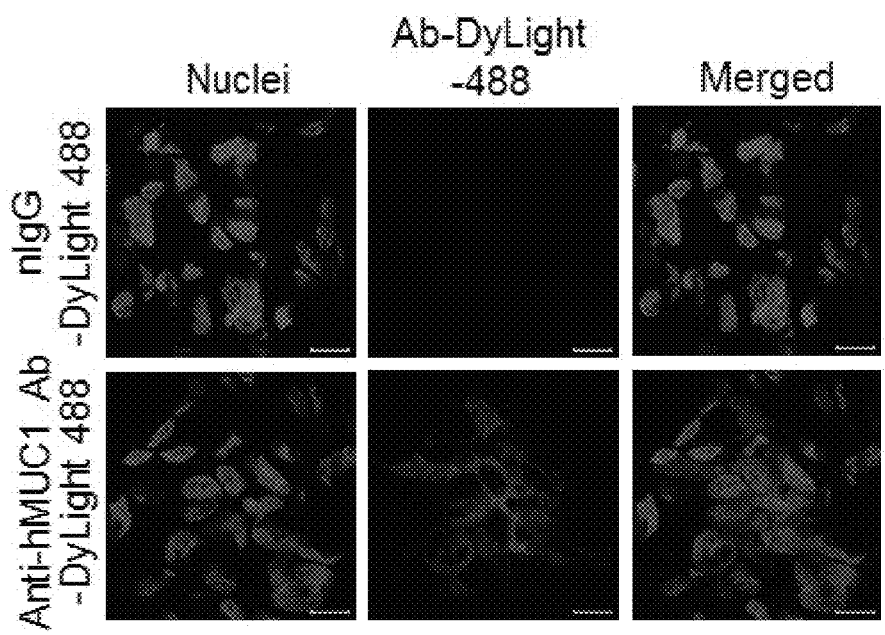

The obtained results are shown in FIGS. 10a to 10h (breast cancer) and FIGS. 11a to 11c (pancreatic cancer).

FIGS. 10a to 10d show the result of induction of tumors in mice by subcutaneous injection with T47D cells, as breast cancer cells, and FIGS. 10e to 10h show the result of induction of tumors in mice by subcutaneous injection with ZR75-1 cells, as breast cancer cells. In FIGS. 10b and 10f, imaging of dissected mice was performed using a real-time IVIS imaging system 200. FIGS. 10c and 10g show the results of distribution of antibodies in various separated organs and tumors. FIGS. 10d and 10h show the result of confocal microscopy (scale bar: 10 µm) of tumor sections having nuclei stained with DAPI.

The results of FIGS. 10a, 10b, 10e, 10f, 11a, and 11b showed that the anti-hMUC1 antibody is specifically localized in the tumor region. Furthermore, the results of FIGS. 10c and 10g showed that, when tumors and other organs were separated, the anti-hMUC1 antibody was located only in tumor tissues, without affecting other important organs.

Also, the results showed that the DyLight-labeled anti-hMUC1 monoclonal antibody shows the result of clear staining in the tumor section, whereas the DyLight-labeled normal IgG did not have this effect. Further, the confocal images of FIGS. 10d, 10h and 11c further showed the anti-hMUC1 monoclonal antibody is located in tumor-specific cells.

These results suggest that the anti-hMUC1 monoclonal antibody can be used to specifically target breast cancer and pancreatic cancer in animal models.

Example 23: Testing of Anti-Cancer Effect of Anti-hMUC1 Monoclonal Antibody in Xenograft Mouse Model The effect of MUC1-targeted monoclonal antibodies on the growth of pancreatic cancer cells was tested in vivo using a xenograft mouse model. First, Capan-2 cells were subcutaneously injected into the dorsal right flank of NORs mice (n=8) to allow tumor growth. When the tumor size reached 75 mm$^3$, the anti-hMUC1 monoclonal antibody was administered intravenously twice a week and the tumor size was monitored for 11 weeks. The preparation of the xenograft mouse model and the tumor size testing were carried out according to Example 14.

During the xenograft mouse model testing, two of the eight mice in the PBS administration group died and one of the eight mice in the anti-hMUC1 monoclonal antibody administration group died.

Figure 12A:
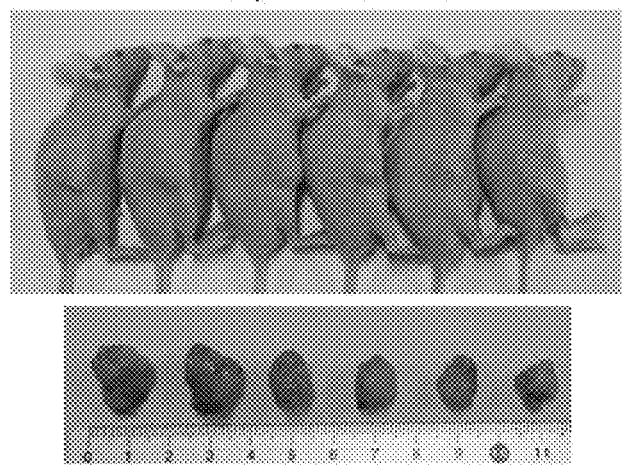
FIG. 12a shows a tumor tissue extracted from a xenograft mouse model.
Figure 12A:
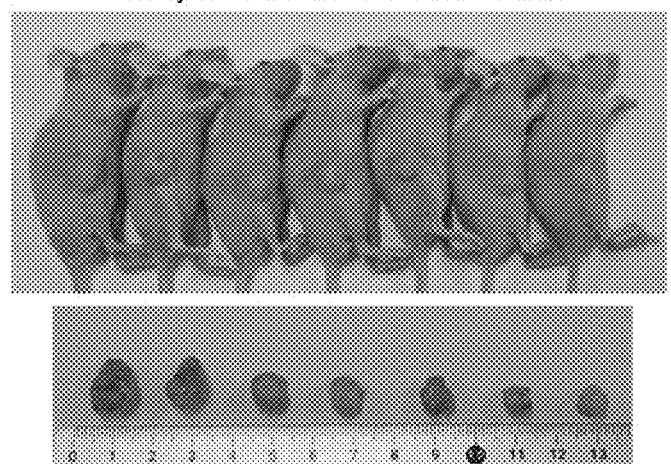
Figure 12B:
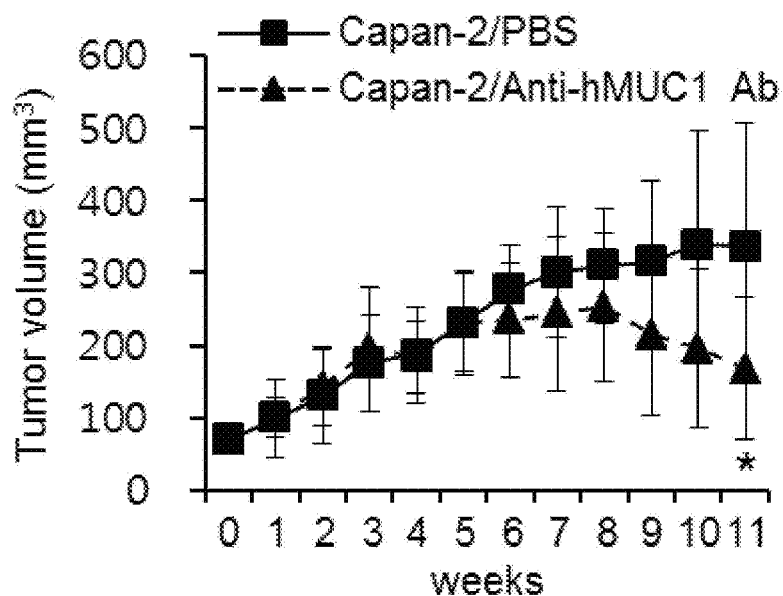
FIG. 12b is a graph showing the size ((width$^2$×length)/2) of a tumor extracted from the xenograft mouse model administered with the anti-hMUC1 monoclonal antibody derived from hMUC1-1H7 clone.
Figure 12C:
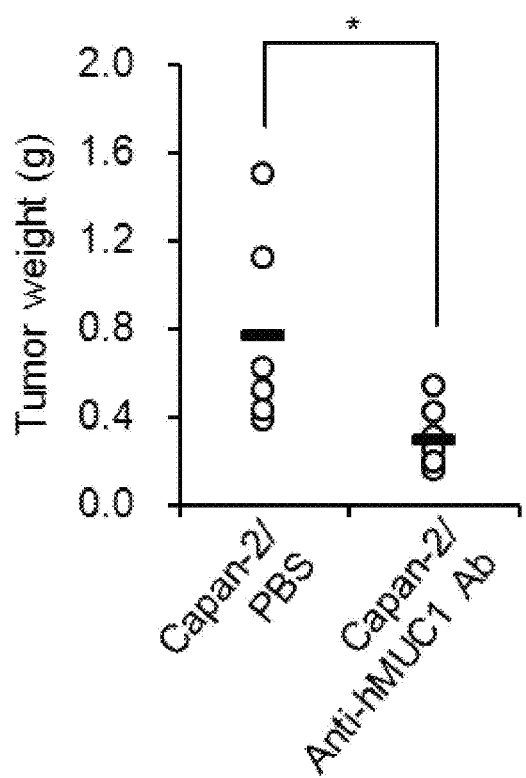
FIG. 12c is a graph showing the weight of tumor extracted from the xenograft mouse model administered with the anti-hMUC1 monoclonal antibody.
Figure 12D:
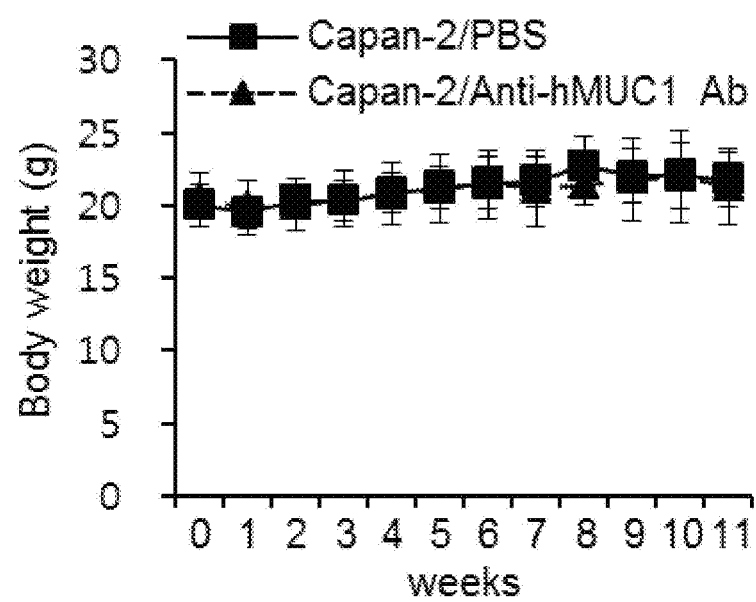
FIG. 12d is a graph showing the body weight of the xenograft mouse model administered with the anti-hMUC1 monoclonal antibody.

The tumor tissue extracted from the xenograft mouse model is shown in FIG. 12a and the size ((width$^2$×length)/2) of the tumors, the weight thereof and the body weight of the mice are shown in FIGS. 12b, 12c and 12d, respectively. As can be seen from FIGS. 12a to 12d, administration of the anti-hMUC1 monoclonal antibody inhibited the progression of the pancreatic tumor and the antibody treatment did not adversely affect the body weight of the subject.

Figure 13:
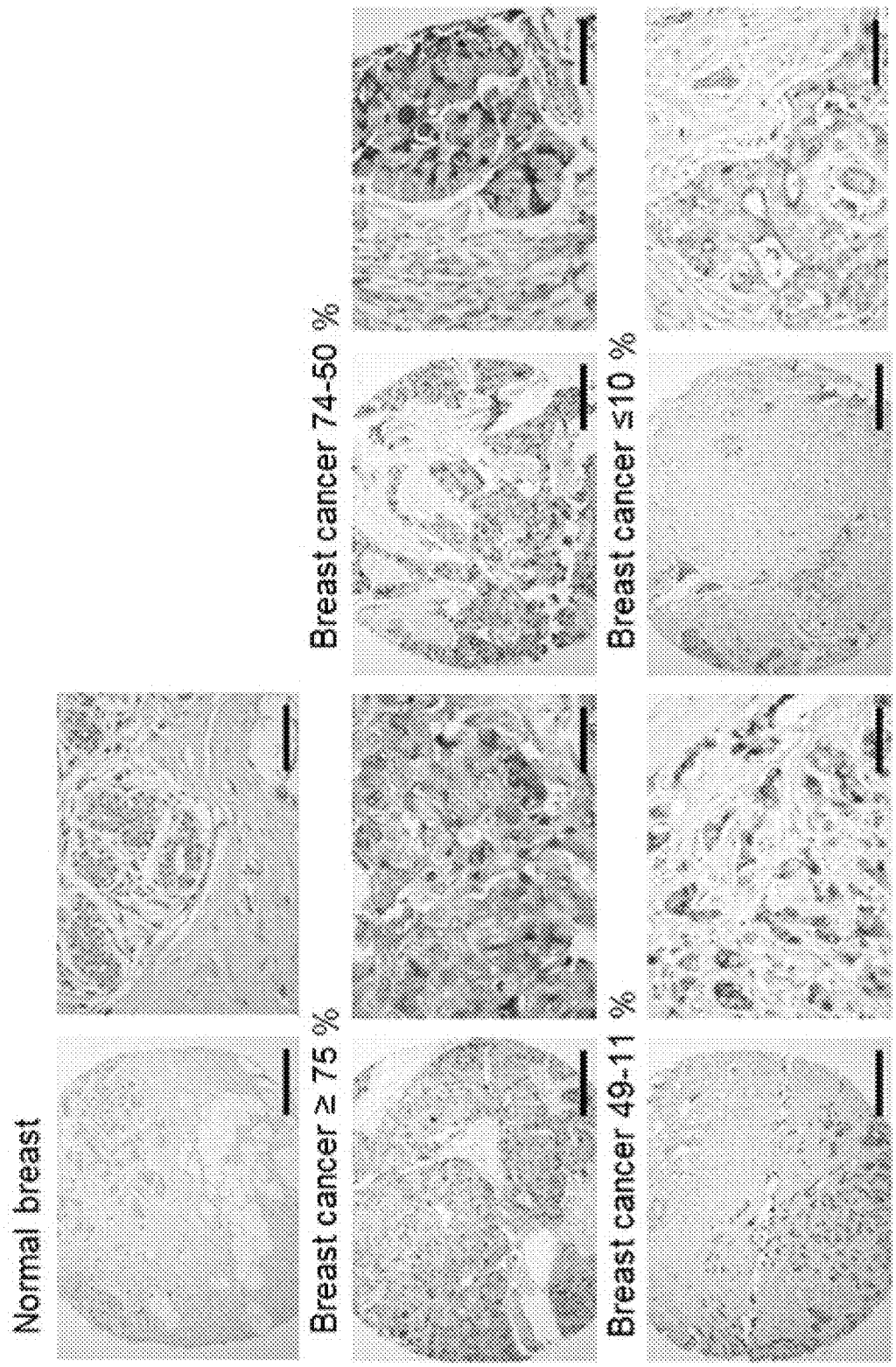
FIG. 13 shows the result of identification of whether or not MUC1 protein is expressed in breast cancer tissues.
Figure 14:
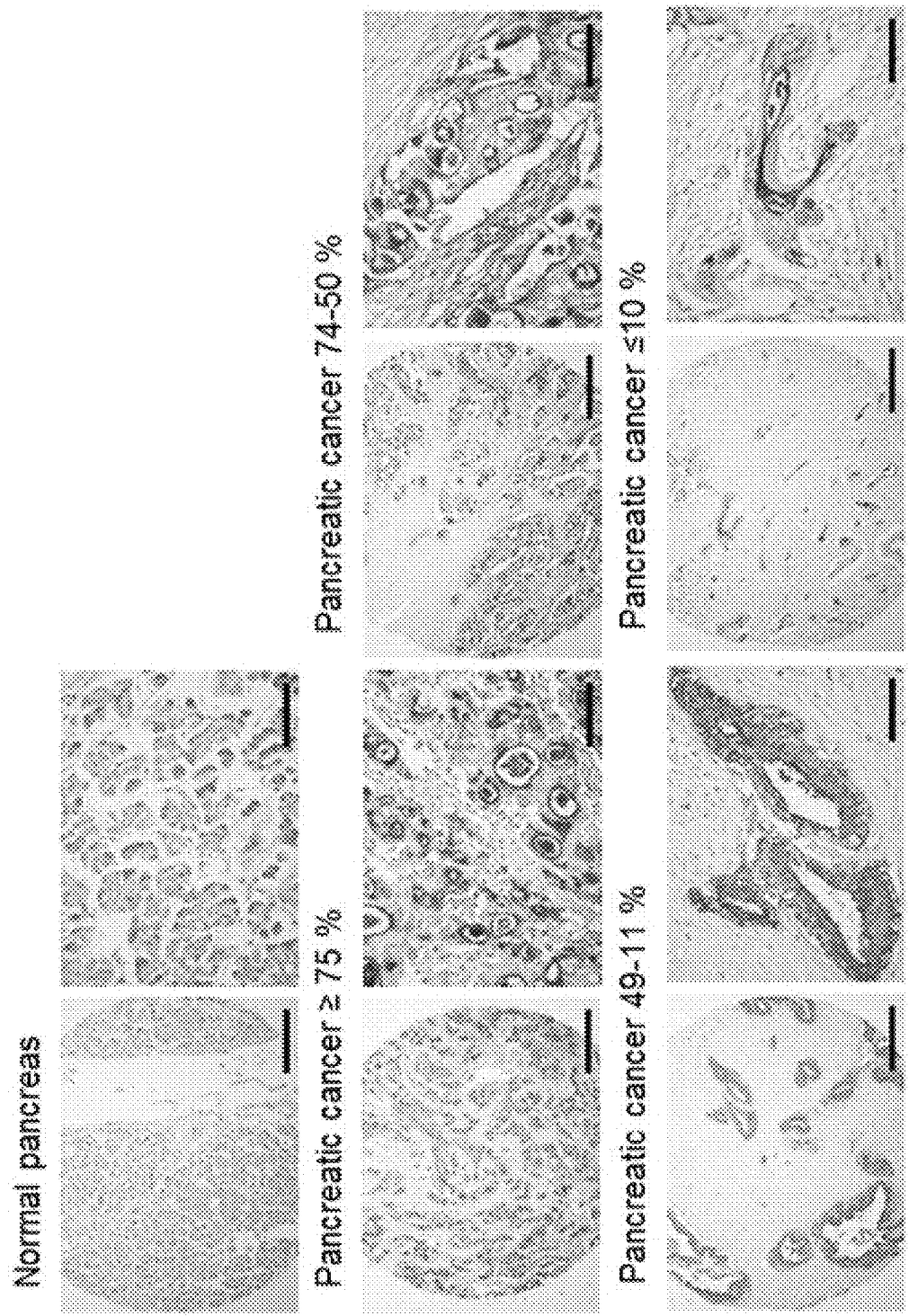
FIG. 14 shows the result of identification of whether or not MUC1 protein is expressed in pancreatic cancer tissues.

Example 24: Testing of Expression of MUC1 Protein in Human Breast Cancer and Pancreatic Cancer Tissues Whether or not MUC1 protein is expressed in breast cancer and pancreatic cancer tissues was investigated through immunohistochemistry. Breast cancer tissue and pancreatic cancer tissues were tested compared to normal tissue as a control group. The results are shown in FIG. 13 (breast cancer) and FIG. 14 (pancreatic cancer). As can be seen from FIGS. 13 and 14, MUC1 is expressed in most breast cancer tissues and pancreatic cancer tissues, while MUC1 is not expressed in normal breast tissues.

The results of immunohistochemical analysis of MUC1 expression in breast cancer tissue and pancreatic cancer tissue are shown in Table 4 (breast tumor tissue) and Table 5 (pancreatic cancer tissue), respectively.

TABLE 4

| Breast cancer tissue sections | | MUC1 positive | Number (%) of cases expressing MUC1 | | | | Negative |
|---|---|---|---|---|---|---|---|
| (AccuMax Array) | n | (%) | >75% | 50-74% | 11-49% | <10% | (%) |
| A312 (II) | 21 | 16 (76.2%) | 5 (23.8%) | 5 (23.8%) | 6 (28.6%) | 4 (19%) | 1 (4.8%) |
| A202 (VIII) | 30 | 13 (43.3%) | 4 (13.3%) | 2 (6.7%) | 7 (23.3%) | 12 (40%) | 5 (16.7%) |
| total | 51 | 29 (56.9%) | 9 (17.6%) | 7 (13.7%) | 13 (25.5%) | 16 (31.4) | 6 (11.8%) |

TABLE 5

| Pancreas cancer tissue sections | | MUC1 positive | Number (%) of cases expressing MUC1 | | | | Negative |
|---|---|---|---|---|---|---|---|
| (AccuMax Array) | n | (%) | >75% | 74-50% | 49-11% | <10% | (%) |
| A207 (IV) | 33 | 60.6 | 1 (3.0) | 3 (9.1) | 16 (48.5) | 10 (30.3) | 3 (9.1) |

As shown in Table 4, the results of analysis of 51 breast cancer samples showed that 18% of all samples were positive for MUC1 in over 75% of tumor cells. 14% and 25% of cancer cell samples were positive for MUC1 expression in 50-74% and 11-49% of tumor cells, respectively. However, 12% of the breast cancer samples did not express MUC1.

In addition, as shown in Table 5, in the case of 33 pancreatic cancer samples, 3% of the samples were positive for MUC1 in 75% or more of the tumor cells. 9.1% and 48.5% of cancer samples were positive for MUC1 expression in 50-74% and 11-49% of tumor cells, respectively.

These results suggest that MUC1 expression can be useful in the diagnosis and treatment of breast cancer.

Figure 15:
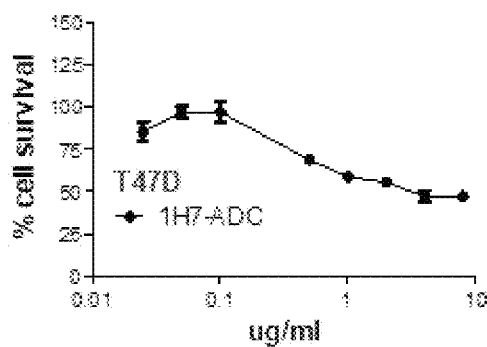
FIG. 15 shows the cytotoxicity of the hMUC1-1H7 antibody-drug conjugate in breast cancer cell lines.

Example 25: Identification of Cytotoxicity of Anti-hMUC1 Mouse Antibody (1H7) ADC ADC was produced by binding MMAE to a 1H7 antibody in Levene Biopharma (USA). The ratio of the MMAE to the antibody of the prepared ADC (drug-to-antibody ratio, DAR) was 5.80. Three cell lines of MDA-MB-231, T47D and ZR75-1 were used for cytotoxicity of 1H7-ADC. Each cell line was cultured in a 96-well plate, and 24 hours after the beginning of the culture, the 1H7-ADC was treated at a predetermined concentration, as shown in FIG. 15. Cell survival was compared using CCK-8 kit (Dojindo, USA) 72 hours after 1H7-ADC treatment. The treatment with CCK-8 was performed according to the provided manual, and the absorbance was measured using an I3X microplate reader (Molecular Devices, USA). The survival of T47D and ZR75-1 cells treated with 1H7-ADC was significantly lower than that of the control group not treated with 1H7-ADC. In contrast, the survival of MDA-MB-231 cells treated with 1H7-ADC was not significantly different from that of the control group. These results mean that 1H7-ADC has a selective anticancer effect on cancer cells expressing MUC1.

Figure 16:
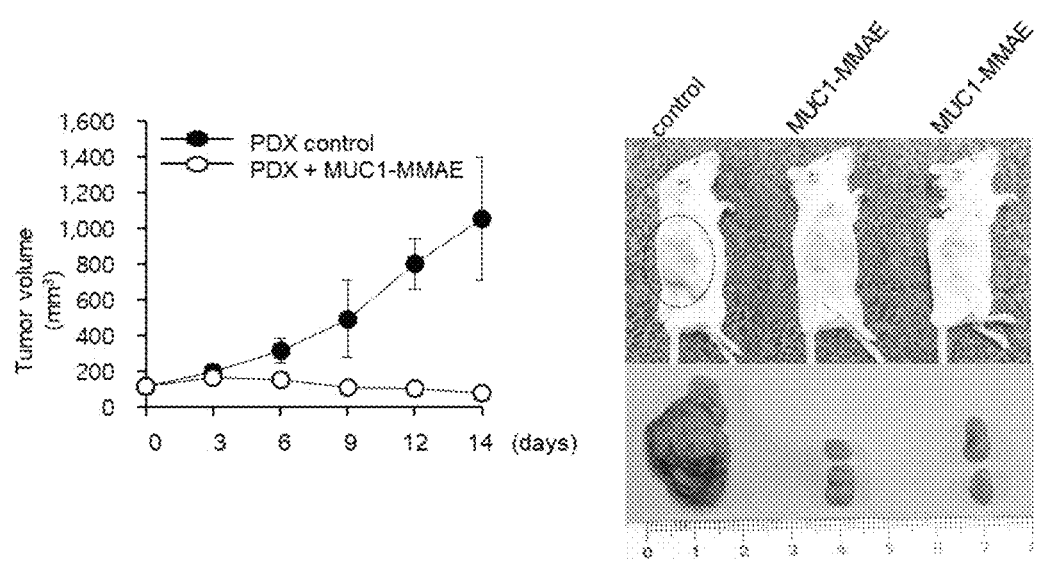
FIG. 16 shows the inhibitory effect of the hMUC1-1H7 antibody-drug conjugate on cancer cell proliferation in breast cancer tissues.

Example 26: Inhibitory Effect of Anti-hMUC1 Monoclonal Antibody (1H7)-ADC on Cancer Proliferation in Patient-Derived Breast Cancer Tissues The inhibitory effect of the 1H7-ADC mentioned in Example 25 on cancer proliferation was identified in animal models. MUC1 over-expressed patient-derived breast cancer tissue (TNBC) purchased from Jung-ah Biotech (Seoul, Korea) was transplanted into NRGA mice, and 1H7-ADC was administered thereto through vascular injection when the breast cancer tissues transplanted into mice were grown over a certain size (100-200 mm$^3$). As shown in FIG. 16, the size of cancer tissues in the mice, to which 1H7-ADC was administered, decreased over time, while the size of cancer tissues of the control mice, to which no 1H7-ADC was administered, increased in proportion with time. The results indicate that 1H7-ADC has an effect of inhibiting the growth of cancer cells at the tissue level in cancer tissues derived from patients expressing MUC1.

Example 27: Production of 1H7-Based Humanized Antibody

Humanized antibodies were produced based on the 1H7 antibody, which was used to identify cytotoxicity and the anti-cancer effect in animal models through ADC production. The humanized antibody was produced by the new drug development support center in Osong High-Tech Medical Industry Promotion Foundation (Osong, Korea) and Fusion Antibodies (UK). Six heavy-chain sequences and six light-chain sequences were produced by using the same antigen recognition site of the 1H7 antibody and changing the variable region sequence, other than the antigen recognition site. Each amino acid sequence is shown in Table 6.

TABLE 6

| Antibody | | Amino acid sequence | SEQ ID NO |
|---|---|---|---|
| G3 | Heavy-chain variable region | EVQLVQSGAEVKKPGATVKISCKVSGYTFTSYWM HWVQQAPGKGLEWIGYINPGTGYIEYNQKFKDRV TITADKSTDTAYMELSSLRSEDTAVYYCASSTAP FDYWGQGTLVTVSS | 24 |
| | Light-chain variable region | EIVLTQSPGTLSLSPGERATLSCKASQDIKSYLS WYQQKPGQAPRLLIYYATRLADGIPDRFSGSGSG TDFTLTISRLEPEDFAVYYCLQYDESPYTFGQGT KLEIKR | 25 |

Figure 17:
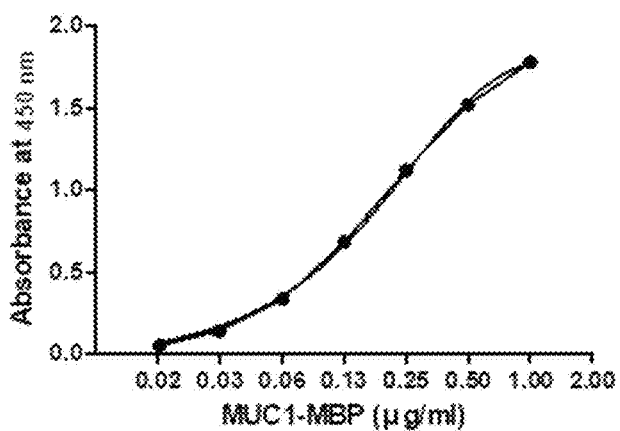
FIG. 17 shows the result of identification of the binding affinity of humanized antibody (hMUC1-G3) and hMUC1-C through ELISA.

Example 28: Measurement of Binding Affinity of Humanized Antibody to hMUC1-C The affinity for binding of anti-hMUC1-C humanized antibody prepared in Example 27 to hMUC1-C protein was measured through an ELISA method. Affinity analysis by ELISA was performed by coating a 96-well immunoplate with the prepared anti-hMUC1-C humanized antibody at the same concentration and blocking the same with a super block solution. Then, the MBP-hMUC1-C protein was diluted and added to the immunoplate coated with anti-hMUC1-C humanized antibody, and allowed to stand at 37° C. in an incubator to induce binding. The plate was washed three times with wash solution and reacted with HRP-conjugated anti-MBP antibody. The reaction was progressed using a TMB substrate solution and the reaction was terminated using 2N HCl. Then, the absorbance value obtained by the antigen-antibody binding reaction was measured through an I3X microplate reader (Molecular Devices, USA), and a colorimetric assay was performed. FIG. 17 shows the difference in binding affinity of the coated humanized antibody to MBP-hMUC1-C.

Example 29: Identification of Epitope Homology Between Anti-hMUC1-C Humanized Antibody and Anti-hMUC1-C Mouse Antibody (1H7)

Figure 18:
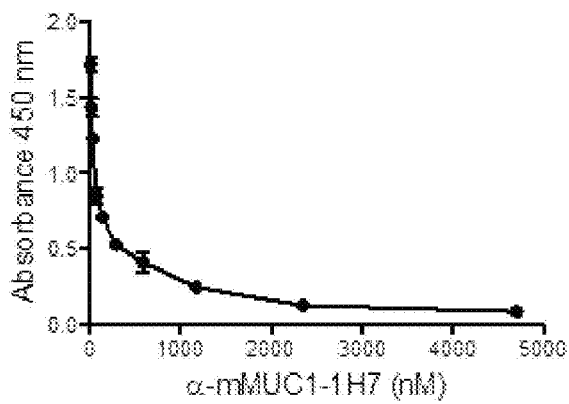
FIG. 18 shows the result of ELISA identifying the epitope homology of hMUC1-C recognized by the hMUC1-G3 antibody and hMUC1-1H7 antibody.

The epitope homology of the produced anti-hMUC1-C humanized antibody and the anti-hMUC1-C mouse antibody was identified by competitive ELISA. MBP-hMUC1-C protein was diluted and coated at various concentrations on 96-well immunoplates. Then, biotin-labeled 50 nM anti-hMUC1-C humanized antibody and anti-hMUC1-C mouse antibody were serially diluted from 5 μm, simultaneously added to a plate coated with MBP-hMUC1-C protein, and allowed to stand to induce reaction. HRP-labeled streptavidin was treated at a constant concentration to detect anti-hMUC1-C humanized antibody-labeled biotin. The TMB substrate solution used to identify affinity was used for colorimetric analysis. Absorbance by the reaction was measured and analyzed using an I3X microplate reader (Molecular Devices, USA). The result is shown in FIG. 18, and the absorbance decreases as the concentration of the anti-hMUC1-C mouse antibody with no biotin labeling increases, which indicates that the anti-hMUC1-C humanized antibody and the anti-hMUC1-C mouse antibody recognize the same epitope.

Example 30: Analysis of Cell Binding Pattern of Anti-hMUC1-C Humanized Antibody to hMUC1-C (FACS Analysis)

Figure 19:
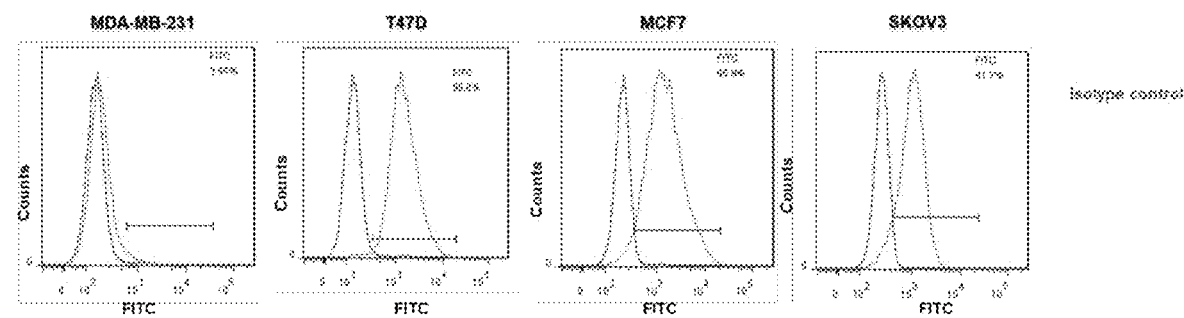
FIG. 19 shows the result of flow cytometry identifying that hMUC1-G3 antibody specifically recognizes hMUC1 expressed in cells.

FACS analysis was performed to analyze the cell-binding pattern of anti-hMUC1 humanized antibody to hMUC1-C in cell lines known to express hMUC1. Each cell line was cultured in a culture medium, and a predetermined number of cells were divided into respective tubes. Then, the cells were fixed with 4% paraformaldehyde, centrifuged and washed once with an FACS analysis solution. The prepared cell line was treated with an anti-hMUC1 humanized antibody and cultured at 4° C. to allow the corresponding humanized antibody to bind to the cells. Then, the cells were treated with FITC-labeled anti-human IgG antibody and FACS analysis was performed using BD FACS Canto (BD, USA). The results of the analysis are shown in FIG. 19, and were compared with those of human IgG as a control substance. Fluorescence values were increased due to binding between the anti-hMUC1 humanized antibody and hMUC1-C in the three cell lines known to express hMUC1, and the fluorescence value was not changed in the MDA-MB-231 cell line that did not express hMUC1. This indicates that the produced anti-hMUC1 humanized antibody specifically recognizes hMUC1 expressed in the cells.

Figure 20:
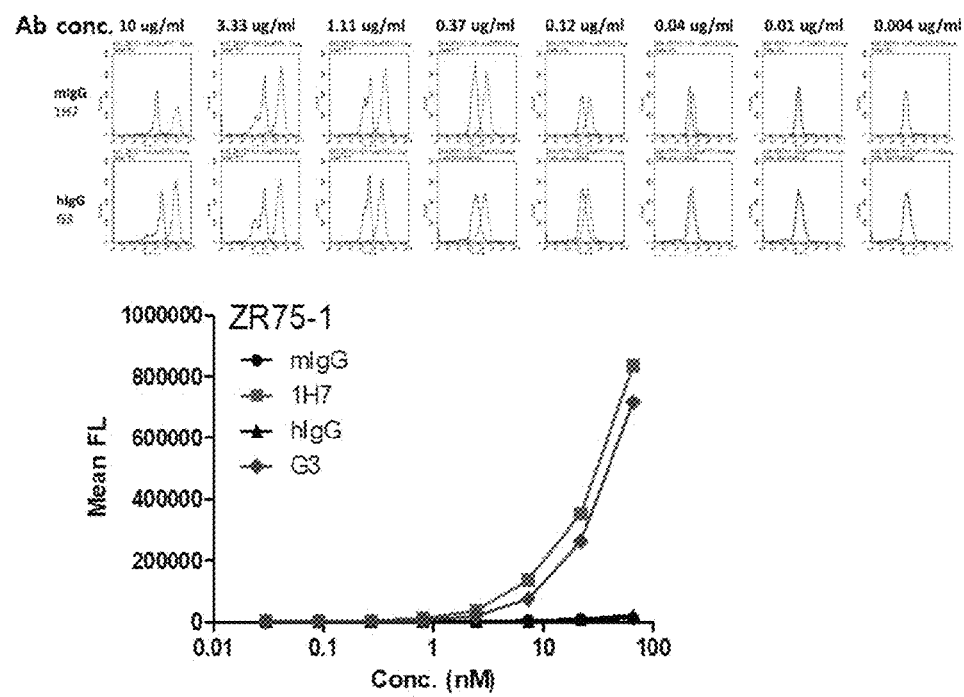
FIG. 20 shows the result of flow cytometry identifying that hMUC1-G3 antibody and hMUC1-1H7 antibody recognize hMUC1 expressed in ZR75-1 breast cancer cells in a concentration-dependent manner.

FACS analysis showed that, when treating the ZR75-1 cell line found to express hMUC1 with various concentrations of anti-hMUC1-C humanized antibody (G3) and anti-hMUC1-C mouse antibody (1H7), the fluorescence value increased depending on the concentration of the antibody. The results of the analysis are shown in FIG. 20.

Example 31: Identification of Cytotoxicity of Anti-hMUC1 Humanized Antibody ADC (G3-ADC)

Example 31-1: Identification of Cytotoxicity in Breast Cancer Cell Line

Figure 21:
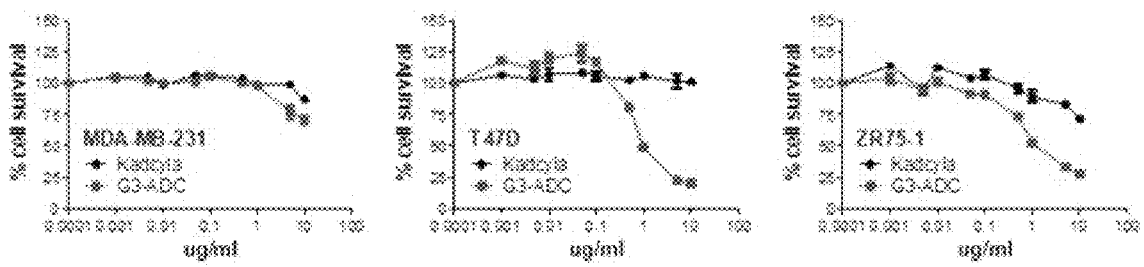
FIG. 21 shows that the hMUC1-G3 antibody-drug conjugate selectively kills breast cancer cells depending on the expression of MUC1 in MUC1-expressing cell lines (ZR75-1, T47D) and a non-MUC1-expressing cell line (MDA-MB-231) among breast cancer cell lines.
Figure 21:
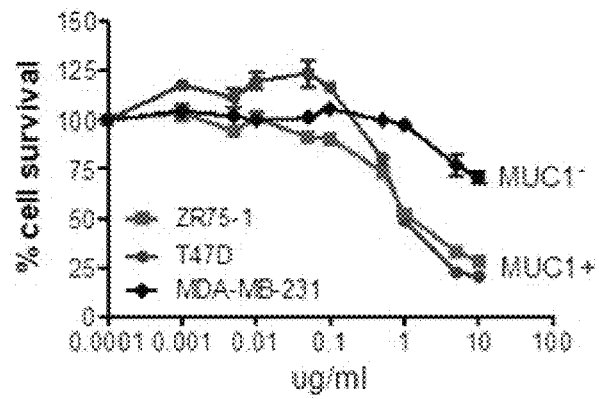

ADC was produced by binding MMAE to anti-hMUC1 humanized antibody in Alteoxen (Daejeon, Korea). The ratio of the MMAE to the antibody of the produced ADC (DAR) was 4.8. Three cell lines of MDA-MB-231 (MUC1−, HER2−), T47D (MUC1+, HER2+) and ZR75-1 (MUC1+, HER2+) were used to determine the cytotoxicity of the produced ADC. Each cell line was cultured in a 96-well plate. 24 hours after the beginning of culture, the cells were treated at the corresponding concentrations with the MUC1-ADC (G3-ADC) and Kadcyla (HER2-ADC) used as a control group. 72 hours after ADC treatment, cell survival was compared using a CellTiterGlo kit (Promega, USA). The CellTiterGlo treatment method was performed according to the manual, and the absorbance was measured using an I3X microplate reader (Molecular Devices, USA). The growth proportions of T47D and ZR75-1 cells treated with G3-ADC were significantly lower than those of the control group not treated with G3-ADC (FIG. 21). On the other hand, the survival of MDA-MB-231 cells treated with ADC was not significantly different from that of the control group. These results indicate that G3-ADC has a selective inhibitory effect on cancer cells expressing MUC1. Kadcyla used as a control group had low cytotoxicity compared to G3-ADC, which is considered to be due to the low expression level of Her2 in the tested cells.

Example 31-2: Identification of Cytotoxicity in Myeloid Leukemia Cell Lines

Figure 22:
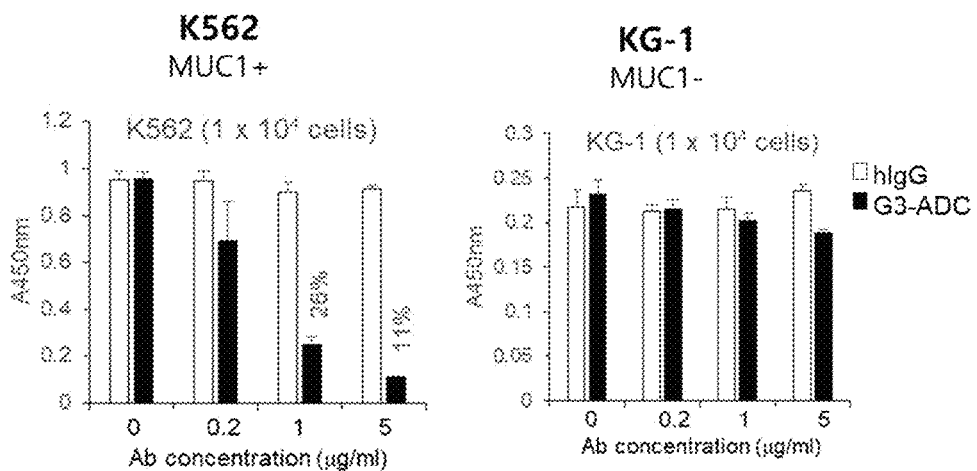
FIG. 22 shows the cytotoxicity of the hMUC1-G3 antibody-drug conjugate in a myeloid leukemia cell line.

Cytotoxicity in myeloid leukemia cell lines was identified using the same anti-hMUC1 humanized antibody ADC as in Example 31-1. The myeloid leukemia cell lines used herein were two types of K562 (MUC1+) and KG-1 (MUC1−) strains. Each cell line was cultured in a 96-well plate, and 24 hours after the beginning of the culture, the cells were treated at the corresponding concentration with anti-hMUC1 humanized antibody ADC. Cell survival (viability, %) was compared through MTT assay 72 hours after treatment with anti-hMUC1 humanized antibody ADC. The survival of cells treated with the anti-hMUC1 humanized antibody ADC was significantly lower than that of the non-treated control group. This result is shown in FIG. 22, and cytotoxicity was found only in the K562 cell line that was found to express MUC1, among the two cell lines.

Figure 23:
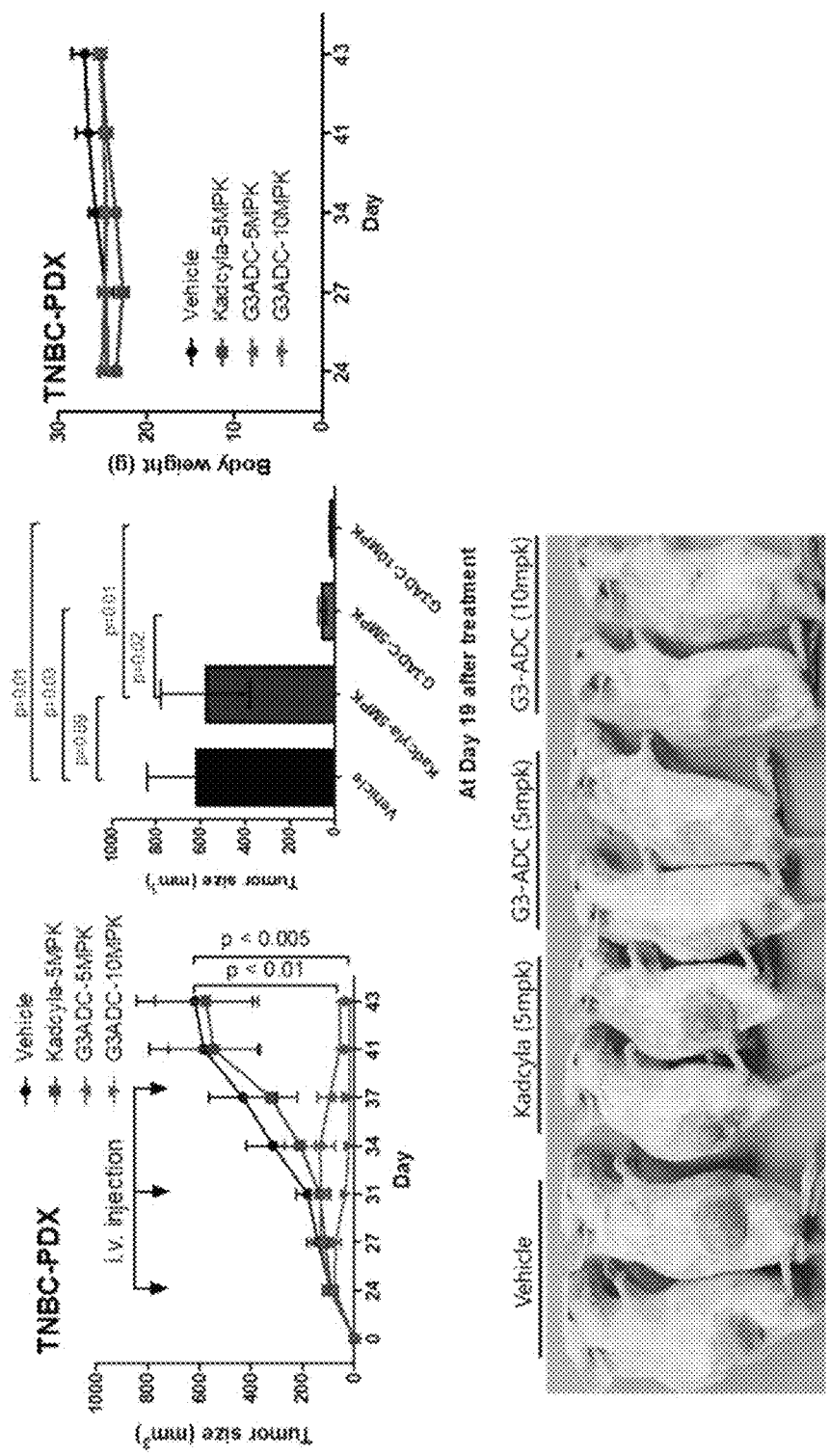
FIG. 23 shows the effect of selectively inhibiting cancer cells by the hMUC1-G3 antibody-drug conjugate in a xenograft mouse model produced by transplantation of TNBC tissue derived from a breast cancer patient.

Example 32: Inhibitory Effect of Anti-hMUC1-C Humanized Antibody-ADC on Cancer Proliferation in Patient-Derived Breast Cancer Tissues The inhibitory effect of the anti-hMUC1-C humanized antibody-drug conjugate mentioned in Example 31 on cancer proliferation was identified in animal models. Breast cancer tissues (TNBC) derived from MUC1-overexpressing patients purchased from Jung-ah Biotech (Seoul, Korea) were transplanted into a total of 24 NRGA mice. When the breast cancer tissues transplanted into mice were grown over a certain size (100-200 mm$^3$), they were randomly selected and divided into 4 groups (n=5). The respective groups were a negative control group, a Kadcyla (5 mg/kg)-administered group, and anti-hMUC1-G3-ADC (5 mg/kg and 10 mg/kg)-administered groups, which were administered by vascular injection once a week three times in total. As can be seen from FIG. 23, the size of the cancer tissues of the mice administered with the anti-hMUC1-C humanized antibody-drug conjugate decreased, while the size of the cancer tissue of the control group mice not administered with the anti-hMUC1-C humanized antibody-drug conjugate showed no statistically significant difference. These results indicate that the anti-hMUC1-C humanized antibody-drug conjugate has an effect of inhibiting the growth of MUC1-expressing cancer tissues, particularly, TNBC breast cancer tissues. No statistically significant weight change was observed in any of the animals that were tested, and the cancer cell growth was found to be effectively inhibited in a concentration-dependent manner. Statistical analysis was performed through two-way ANOVA.

Accession Number
Depositary authority: Korean Cell Line Research Foundation
Accession number: KCLRFBP00395
Accession date: 20170308

INDUSTRIAL AVAILABILITY

According to the present invention, an antibody specifically binding to MUC1 or an antigen-binding fragment thereof exhibits excellent affinity and binding ability to MUC1, and an antibody-drug conjugate in which a drug conjugated with the antibody or an antigen-binding fragment thereof effectively and specifically or selectively delivers the drug by specifically binding to MUC1-expressing cells.

Accordingly, the anti-MUC1 antibody and antibody-drug conjugate according to the present invention can be usefully applied for the treatment of MUC1-associated diseases such as cancer.

Although the specific configurations of the present invention have been described in detail, those skilled in the art will appreciate that this description is provided as preferred embodiments and should not be construed as limiting the scope of the present invention. Therefore, the substantial scope of the present invention is defined by the accompanying filed claims and equivalents thereto.

SEQUENCE LISTING FREE TEXT

An electronic file is attached.

The invention claimed is:

1. An anti-MUC1 antibody or an antigen-binding fragment thereof recognizing a polypeptide comprising at least five consecutive amino acids in a C-terminal extracellular domain of MUC1, comprising:
   a heavy-chain CDR1 of SEQ ID NO: 1; heavy-chain CDR2 of SEQ ID NO: 2; and heavy-chain CDR3 of SEQ ID NO: 3; and
   a light-chain CDR1 of SEQ ID NO: 4; light-chain CDR2 of SEQ ID NO: 5; and light-chain CDR3 of SEQ ID NO: 6.

2. The anti-MUC1 antibody or the antigen-binding fragment thereof according to claim 1, comprising:
   a heavy-chain variable region of SEQ ID NO: 22 or 24; and
   a light-chain variable region of SEQ ID NO: 23 or 25.

3. A bispecific antibody comprising the anti-MUC1 antibody or an antigen-binding fragment thereof according to claim 1.

4. The bispecific antibody according to claim 3, wherein the bispecific antibody comprises an anti-MUC1 antibody or an antigen-binding fragment thereof, and an antibody having an ability to bind to a cancer-associated antigen or an immune checkpoint protein antigen, or an immune-effector cell-specific target molecule.

5. A pharmaceutical composition for treating cancer comprising (i) the anti-MUC1 antibody or the antigen-binding fragment thereof according to claim 1, or (ii) a bispecific antibody comprising the anti-MUC1 antibody or the antigen-binding fragment thereof.

6. A composition for diagnosing cancer comprising the anti-MUC1 antibody or the antigen-binding fragment thereof according to claim 1.

* * * * *

```
SEQUENCE LISTING

<160> NUMBER OF SEQ ID NOS: 26

<210> SEQ ID NO 1
<211> LENGTH: 10
<212> TYPE: PRT
<213> ORGANISM: Artificial Sequence
<220> FEATURE:
<223> OTHER INFORMATION: Heavy chain variable region CDR1

<400> SEQUENCE: 1

Gly Tyr Thr Phe Thr Ser Tyr Trp Met His
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Heavy chain variable region CDR2

<400> SEQUENCE: 2

Tyr Ile Asn Pro Gly Thr Gly Tyr Ile Glu Tyr Asn Gln Lys Phe Lys
1               5                   10                  15

<210> SEQ ID NO 3
<211> LENGTH: 7
<212> TYPE: PRT
<213> ORGANISM: Artificial Sequence
<220> FEATURE:
<223> OTHER INFORMATION: Heavy chain variable region CDR3

<400> SEQUENCE: 3

Ser Thr Ala Pro Phe Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Light chain variable region CDR1

<400> SEQUENCE: 4

Lys Ala Ser Gln Asp Ile Lys Ser Tyr Leu Ser
1               5                   10

<210> SEQ ID NO 5
<211> LENGTH: 7
<212> TYPE: PRT
<213> ORGANISM: Artificial Sequence
```

```
<220> FEATURE:
<223> OTHER INFORMATION: Light chain variable region CDR2

<400> SEQUENCE: 5

Tyr Ala Thr Arg Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Light chain variable region CDR3

<400> SEQUENCE: 6

Leu Gln Tyr Asp Glu Ser Pro Tyr Thr
1               5

<210> SEQ ID NO 7
<211> LENGTH: 1255
<212> TYPE: PRT
<213> ORGANISM: Artificial Sequence
<220> FEATURE:
<223> OTHER INFORMATION: MUC1

<400> SEQUENCE: 7

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
                100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
        130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
                180                 185                 190

Pro Pro Ala His Gly Val Thr Ser Ala Pro Asp Thr Arg Pro Ala Pro
            195                 200                 205

Gly Ser Thr Ala Pro Pro Ala His Gly Val Thr Ser Ala Pro Asp Thr
        210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255
```

```
Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
    370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
        435                 440                 445

Gly Ser Thr Ala Pro Pro Ala His Gly Val Thr Ser Ala Pro Asp Thr
    450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
    530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
```

|     |     |     | 675 |     |     |     | 680 |     |     |     | 685 |     |     |
| --- | --- | --- | --- | --- | --- | --- | --- | --- | --- | --- | --- | --- | --- |
| Gly | Ser | Thr | Ala | Pro | Pro | Ala | His | Gly | Val | Thr | Ser | Ala | Pro | Asp | Thr |
|     |     |     | 690 |     |     |     | 695 |     |     |     | 700 |     |     |
| Arg | Pro | Ala | Pro | Gly | Ser | Thr | Ala | Pro | Pro | Ala | His | Gly | Val | Thr | Ser |
| 705 |     |     |     | 710 |     |     |     | 715 |     |     |     | 720 |     |
| Ala | Pro | Asp | Thr | Arg | Pro | Ala | Pro | Gly | Ser | Thr | Ala | Pro | Pro | Ala | His |
|     |     |     |     | 725 |     |     |     | 730 |     |     |     |     | 735 |
| Gly | Val | Thr | Ser | Ala | Pro | Asp | Thr | Arg | Pro | Ala | Pro | Gly | Ser | Thr | Ala |
|     |     |     |     | 740 |     |     |     | 745 |     |     |     | 750 |     |
| Pro | Pro | Ala | His | Gly | Val | Thr | Ser | Ala | Pro | Asp | Thr | Arg | Pro | Ala | Pro |
|     |     |     | 755 |     |     |     | 760 |     |     |     | 765 |     |     |
| Gly | Ser | Thr | Ala | Pro | Pro | Ala | His | Gly | Val | Thr | Ser | Ala | Pro | Asp | Thr |
|     |     |     | 770 |     |     |     | 775 |     |     |     | 780 |     |     |
| Arg | Pro | Ala | Pro | Gly | Ser | Thr | Ala | Pro | Pro | Ala | His | Gly | Val | Thr | Ser |
| 785 |     |     |     | 790 |     |     |     | 795 |     |     |     | 800 |     |
| Ala | Pro | Asp | Thr | Arg | Pro | Ala | Pro | Gly | Ser | Thr | Ala | Pro | Pro | Ala | His |
|     |     |     |     | 805 |     |     |     | 810 |     |     |     |     | 815 |
| Gly | Val | Thr | Ser | Ala | Pro | Asp | Thr | Arg | Pro | Ala | Pro | Gly | Ser | Thr | Ala |
|     |     |     |     | 820 |     |     |     | 825 |     |     |     | 830 |     |
| Pro | Pro | Ala | His | Gly | Val | Thr | Ser | Ala | Pro | Asp | Thr | Arg | Pro | Ala | Pro |
|     |     |     | 835 |     |     |     | 840 |     |     |     | 845 |     |     |
| Gly | Ser | Thr | Ala | Pro | Pro | Ala | His | Gly | Val | Thr | Ser | Ala | Pro | Asp | Thr |
|     |     |     | 850 |     |     |     | 855 |     |     |     | 860 |     |     |
| Arg | Pro | Ala | Pro | Gly | Ser | Thr | Ala | Pro | Pro | Ala | His | Gly | Val | Thr | Ser |
| 865 |     |     |     | 870 |     |     |     | 875 |     |     |     | 880 |     |
| Ala | Pro | Asp | Thr | Arg | Pro | Ala | Pro | Gly | Ser | Thr | Ala | Pro | Pro | Ala | His |
|     |     |     |     | 885 |     |     |     | 890 |     |     |     |     | 895 |
| Gly | Val | Thr | Ser | Ala | Pro | Asp | Thr | Arg | Pro | Ala | Pro | Gly | Ser | Thr | Ala |
|     |     |     |     | 900 |     |     |     | 905 |     |     |     | 910 |     |
| Pro | Pro | Ala | His | Gly | Val | Thr | Ser | Ala | Pro | Asp | Thr | Arg | Pro | Ala | Pro |
|     |     |     | 915 |     |     |     | 920 |     |     |     | 925 |     |     |
| Gly | Ser | Thr | Ala | Pro | Pro | Ala | His | Gly | Val | Thr | Ser | Ala | Pro | Asp | Asn |
|     |     |     | 930 |     |     |     | 935 |     |     |     | 940 |     |     |
| Arg | Pro | Ala | Leu | Gly | Ser | Thr | Ala | Pro | Pro | Val | His | Asn | Val | Thr | Ser |
| 945 |     |     |     | 950 |     |     |     | 955 |     |     |     | 960 |     |
| Ala | Ser | Gly | Ser | Ala | Ser | Gly | Ser | Ala | Ser | Thr | Leu | Val | His | Asn | Gly |
|     |     |     |     | 965 |     |     |     | 970 |     |     |     | 975 |     |
| Thr | Ser | Ala | Arg | Ala | Thr | Thr | Thr | Pro | Ala | Ser | Lys | Ser | Thr | Pro | Phe |
|     |     |     | 980 |     |     |     | 985 |     |     |     | 990 |     |     |
| Ser | Ile | Pro | Ser | His | His | Ser | Asp | Thr | Pro | Thr | Thr | Leu | Ala | Ser | His |
|     |     |     | 995 |     |     |     | 1000 |     |     |     | 1005 |     |     |
| Ser | Thr | Lys | Thr | Asp | Ala | Ser | Ser | Thr | His | His | Ser | Ser | Val | Pro |
|     |     |     | 1010 |     |     |     | 1015 |     |     |     | 1020 |     |
| Pro | Leu | Thr | Ser | Ser | Asn | His | Ser | Thr | Ser | Pro | Gln | Leu | Ser | Thr |
|     |     |     | 1025 |     |     |     | 1030 |     |     |     | 1035 |     |
| Gly | Val | Ser | Phe | Phe | Phe | Leu | Ser | Phe | His | Ile | Ser | Asn | Leu | Gln |
|     |     |     | 1040 |     |     |     | 1045 |     |     |     | 1050 |     |
| Phe | Asn | Ser | Ser | Leu | Glu | Asp | Pro | Ser | Thr | Asp | Tyr | Tyr | Gln | Glu |
|     |     |     | 1055 |     |     |     | 1060 |     |     |     | 1065 |     |
| Leu | Gln | Arg | Asp | Ile | Ser | Glu | Met | Phe | Leu | Gln | Ile | Tyr | Lys | Gln |
|     |     |     | 1070 |     |     |     | 1075 |     |     |     | 1080 |     |
| Gly | Gly | Phe | Leu | Gly | Leu | Ser | Asn | Ile | Lys | Phe | Arg | Pro | Gly | Ser |
|     |     |     | 1085 |     |     |     | 1090 |     |     |     | 1095 |     |

```
Val Val Val Gln Leu Thr Leu Ala Phe Arg Glu Gly Thr Ile Asn
    1100            1105                1110

Val His Asp Val Glu Thr Gln Phe Asn Gln Tyr Lys Thr Glu Ala
    1115            1120                1125

Ala Ser Arg Tyr Asn Leu Thr Ile Ser Asp Val Ser Val Ser Asp
    1130            1135                1140

Val Pro Phe Pro Phe Ser Ala Gln Ser Gly Ala Gly Val Pro Gly
    1145            1150                1155

Trp Gly Ile Ala Leu Leu Val Leu Val Cys Val Leu Val Ala Leu
    1160            1165                1170

Ala Ile Val Tyr Leu Ile Ala Leu Ala Val Cys Gln Cys Arg Arg
    1175            1180                1185

Lys Asn Tyr Gly Gln Leu Asp Ile Phe Pro Ala Arg Asp Thr Tyr
    1190            1195                1200

His Pro Met Ser Glu Tyr Pro Thr Tyr His Thr His Gly Arg Tyr
    1205            1210                1215

Val Pro Pro Ser Ser Thr Asp Arg Ser Pro Tyr Glu Lys Val Ser
    1220            1225                1230

Ala Gly Asn Gly Gly Ser Ser Leu Ser Tyr Thr Asn Pro Ala Val
    1235            1240                1245

Ala Ala Thr Ser Ala Asn Leu
    1250            1255

<210> SEQ ID NO 8
<211> LENGTH: 192
<212> TYPE: PRT
<213> ORGANISM: Artificial Sequence
<220> FEATURE:
<223> OTHER INFORMATION: MUC1 Extracellular domain

<400> SEQUENCE: 8

Ala Ser Gly Ser Ala Ser Gly Ser Ala Ser Thr Leu Val His Asn Gly
1               5                   10                  15

Thr Ser Ala Arg Ala Thr Thr Thr Pro Ala Ser Lys Ser Thr Pro Phe
            20                  25                  30

Ser Ile Pro Ser His His Ser Asp Thr Pro Thr Thr Leu Ala Ser His
        35                  40                  45

Ser Thr Lys Thr Asp Ala Ser Ser Thr His His Ser Thr Val Pro Pro
    50                  55                  60

Leu Thr Ser Ser Asn His Ser Thr Ser Pro Gln Leu Ser Thr Gly Val
65                  70                  75                  80

Ser Phe Phe Phe Leu Ser Phe His Ile Ser Asn Leu Gln Phe Asn Ser
                85                  90                  95

Ser Leu Glu Asp Pro Ser Thr Asp Tyr Tyr Gln Glu Leu Gln Arg Asp
            100                 105                 110

Ile Ser Glu Met Phe Leu Gln Ile Tyr Lys Gln Gly Gly Phe Leu Gly
        115                 120                 125

Leu Ser Asn Ile Lys Phe Arg Pro Gly Ser Val Val Val Gln Leu Thr
    130                 135                 140

Leu Ala Phe Arg Glu Gly Thr Ile Asn Val His Asp Val Glu Thr Gln
145                 150                 155                 160

Phe Asn Gln Tyr Lys Thr Glu Ala Ala Ser Arg Tyr Asn Leu Thr Ile
                165                 170                 175

Ser Asp Val Ser Val Ser Asp Val Pro Phe Pro Phe Ser Ala Gln Ser
            180                 185                 190
```

<210> SEQ ID NO 9
<211> LENGTH: 119
<212> TYPE: PRT
<213> ORGANISM: Artificial Sequence
<220> FEATURE:
<223> OTHER INFORMATION: MUC1 SEA domain

<400> SEQUENCE: 9

```
Pro Gln Leu Ser Thr Gly Val Ser Phe Phe Leu Ser Phe His Ile
1               5                   10                  15

Ser Asn Leu Gln Phe Asn Ser Ser Leu Glu Asp Pro Ser Thr Asp Tyr
            20                  25                  30

Tyr Gln Glu Leu Gln Arg Asp Ile Ser Glu Met Phe Leu Gln Ile Tyr
        35                  40                  45

Lys Gln Gly Gly Phe Leu Gly Leu Ser Asn Ile Lys Phe Arg Pro Gly
    50                  55                  60

Ser Val Val Val Gln Leu Thr Leu Ala Phe Arg Glu Gly Thr Ile Asn
65                  70                  75                  80

Val His Asp Val Glu Thr Gln Phe Asn Gln Tyr Lys Thr Glu Ala Ala
                85                  90                  95

Ser Arg Tyr Asn Leu Thr Ile Ser Asp Val Ser Val Ser Asp Val Pro
            100                 105                 110

Phe Pro Phe Ser Ala Gln Ser
        115
```

<210> SEQ ID NO 10
<211> LENGTH: 55
<212> TYPE: PRT
<213> ORGANISM: Artificial Sequence
<220> FEATURE:
<223> OTHER INFORMATION: MUC1-C Extracellular domain

<400> SEQUENCE: 10

```
Ser Val Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
            20                  25                  30

Ser Arg Tyr Asn Leu Thr Ile Ser Asp Val Ser Val Ser Asp Val Pro
        35                  40                  45

Phe Pro Phe Ser Ala Gln Ser
    50                  55
```

<210> SEQ ID NO 11
<211> LENGTH: 20
<212> TYPE: DNA
<213> ORGANISM: Artificial Sequence
<220> FEATURE:
<223> OTHER INFORMATION: CpG-DNA

<400> SEQUENCE: 11
agcagcgttc gtgtcggcct                                              20

<210> SEQ ID NO 12
<211> LENGTH: 22
<212> TYPE: DNA
<213> ORGANISM: Artificial Sequence
<220> FEATURE:
<223> OTHER INFORMATION: sense primer

<400> SEQUENCE: 12
ccatggcctc aggctctgca tc                                            22

<210> SEQ ID NO 13
<211> LENGTH: 28
<212> TYPE: DNA
<213> ORGANISM: Artificial Sequence
<220> FEATURE:
<223> OTHER INFORMATION: antisense primer

<400> SEQUENCE: 13
ctcgagagac tgggcagaga aaggaaat                                      28

<210> SEQ ID NO 14
<211> LENGTH: 36
<212> TYPE: DNA
<213> ORGANISM: Artificial Sequence
<220> FEATURE:
<223> OTHER INFORMATION: primer

<400> SEQUENCE: 14
ggaagatcta tagacagatg ggggtgtcgt tttggc                             36

<210> SEQ ID NO 15
<211> LENGTH: 35
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t

<400> SEQUENCE: 15
cttccggaat tcsargtnma gctgsagsag tcwgg                              35

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
ggtgcatgcg gatacagttg gtgcagcatc                                    30

<210> SEQ ID NO 17
<211> LENGTH: 32
<212> TYPE: DNA
<213> ORGANISM: Artificial Sequence
<220> FEATURE:
<223> OTHER INFORMATION: primer

<400> SEQUENCE: 17
gggagctcga yattgtgmts acmcarwctm ca                                 32

<210> SEQ ID NO 18
<211> LENGTH: 42
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: (25)..(25)
<223> OTHER INFORMATION: n is a, c, g, or t

<400> SEQUENCE: 18

```
ggcccagccg gccatggccs argtnmagct gsagsagtcw gg                        42
```

```
<210> SEQ ID NO 19
<211> LENGTH: 39
<212> TYPE: DNA
<213> ORGANISM: Artificial Sequence
<220> FEATURE:
<223> OTHER INFORMATION: Reverse primer

<400> SEQUENCE: 19
ggccgtgctg gccccgacag atgggggtgt cgttttggc                            39
```

```
<210> SEQ ID NO 20
<211> LENGTH: 71
<212> TYPE: DNA
<213> ORGANISM: Artificial Sequence
<220> FEATURE:
<223> OTHER INFORMATION: Forward primer

<400> SEQUENCE: 20
ccattgcagt ggcactggct ggtttcgcta ccgtagcaca ggcagccgay attgtgmtsa     60
cmcarwctmc a                                                          71
```

```
<210> SEQ ID NO 21
<211> LENGTH: 34
<212> TYPE: DNA
<213> ORGANISM: Artificial Sequence
<220> FEATURE:
<223> OTHER INFORMATION: Reverse primer

<400> SEQUENCE: 21
ccaccgtact ggcggataca gttggtgcag catc                                 34
```

```
<210> SEQ ID NO 22
<211> LENGTH: 116
<212> TYPE: PRT
<213> ORGANISM: Artificial Sequence
<220> FEATURE:
<223> OTHER INFORMATION: hMUC1-1H7_Heavy chain variable region

<400> SEQUENCE: 22
```

Glu Val Gln Leu Gln Gln Ser Gly Ala Glu Leu Ala Lys Pro Gly Ala
1               5                   10                  15

Ser Val Lys Met Ser Cys Lys Val Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Gly Thr Gly Tyr Ile Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Ser Thr Ala Pro Phe Asp Tyr Trp Gly Gln Gly Thr Thr Leu
            100                 105                 110

Thr Val Ser Ser
        115

```
<210> SEQ ID NO 23
<211> LENGTH: 108
<212> TYPE: PRT
```

<213> ORGANISM: Artificial Sequence
<220> FEATURE:
<223> OTHER INFORMATION: hMUC1-1H7_Light chain variable region

<400> SEQUENCE: 23

Asp Ile Val Ile Thr Gln Ser Pro Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Ser Trp Tyr Gln Gln Lys Pro Trp Lys Ser Pro Lys Thr Leu Ile
        35                  40                  45

Tyr Tyr Ala Thr Arg Leu Ala Asp Gly Val Pro Ser Arg Phe Ser Gly
50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln Tyr Asp Glu Ser Pro Tyr
                85                  90                  95

Thr Phe Gly Gly Gly Thr Lys Leu Glu Ile Lys Arg
            100                 105

<210> SEQ ID NO 24
<211> LENGTH: 116
<212> TYPE: PRT
<213> ORGANISM: Artificial Sequence
<220> FEATURE:
<223> OTHER INFORMATION: G3_Heavy chain variable region

<400> SEQUENCE: 24

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met His Trp Val Gln Gln Ala Pro Gly Lys Gly Leu Glu Trp Ile
        35                  40                  45

Gly Tyr Ile Asn Pro Gly Thr Gly Tyr Ile Glu Tyr Asn Gln Lys Phe
50                  55                  60

Lys Asp Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Thr Ala Pro Phe Asp Tyr Trp Gly Gln Gly Thr Leu Val
            100                 105                 110

Thr Val Ser Ser
        115

<210> SEQ ID NO 25
<211> LENGTH: 108
<212> TYPE: PRT
<213> ORGANISM: Artificial Sequence
<220> FEATURE:
<223> OTHER INFORMATION: G3_Light chain variable region

<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Lys Ser Tyr
            20                  25                  30

Leu Ser Trp Tyr Gln Gln Lys Pro Gly Gln Ala Pro Arg Leu Leu Ile
        35                  40                  45

```
Tyr Tyr Ala Thr Arg Leu Ala Asp Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Leu Gln Tyr Asp Glu Ser Pro Tyr
                85                  90                  95

Thr Phe Gly Gln Gly Thr Lys Leu Glu Ile Lys Arg
            100                 105

<210> SEQ ID NO 26
<211> LENGTH: 576
<212> TYPE: DNA
<213> ORGANISM: Artificial Sequence
<220> FEATURE:
<223> OTHER INFORMATION: hMUC1-C

<400> SEQUENCE: 26
gcctcaggct ctgcatcagg ctcagcttct actctggtgc acaacggcac ctctgccagg      60
gctaccacaa ccccagccag caagagcact ccattctcaa ttcccagcca ccactctgat     120
actcctacca cccttgccag ccatagcacc aagactgatg ccagtagcac tcaccatagc     180
tcggtacctc ctctcacctc ctccaatcac agcacttctc cccagttgtc tactggggtc     240
tctttctttt tcctgtcttt tcacatttca aacctccagt ttaattcctc tctggaagat     300
cccagcaccg actactacca agagctgcag agagacattt ctgaaatgtt tttgcagatt     360
tataaacaag ggggtttttct gggcctctcc aatattaagt tcaggccagg atctgtggtg     420
gtacaattga ctctggcctt ccgagaaggt accatcaatg tccacgacgt ggagacacag     480
ttcaatcagt ataaaacgga agcagcctct cgatataacc tgacgatctc agacgtcagc     540
gtgagtgatg tgccatttcc tttctctgcc cagtct                                576
```

UNITED STATES PATENT AND TRADEMARK OFFICE
CERTIFICATE OF CORRECTION

| | |
|---|---|
| PATENT NO. | : 11,472,887 B2 |
| APPLICATION NO. | : 16/495373 |
| DATED | : October 18, 2022 |
| INVENTOR(S) | : Kyung Duk Moon et al. |

It is certified that error appears in the above-identified patent and that said Letters Patent is hereby corrected as shown below:

In the Specification

Column 14, Line 2, "131I" should be -- 131I --.

Column 15, Line 24, "amitotic" should be -- a mitotic --.

Column 21, Line 58, "(COST)" should be -- (COS7) --.

Column 22, Line 17, "2p" should be -- 2µ --.

Column 23, Line 17, "X 100" should be -- X100 --.

Signed and Sealed this
Twentieth Day of December, 2022

*Katherine Kelly Vidal*

Katherine Kelly Vidal
*Director of the United States Patent and Trademark Office*